United States Patent [19]

Liskowitz et al.

[11] Patent Number: 5,624,491

[45] Date of Patent: Apr. 29, 1997

[54] COMPRESSIVE STRENGTH OF CONCRETE AND MORTAR CONTAINING FLY ASH

[75] Inventors: John W. Liskowitz, Belle Mead; Methi Wecharatana, Parsippany, both of N.J.; Chai Jaturapitakkul, Bangkok, Thailand; Anthony E. Cerkanowicz, deceased, late of Livingston, N.J., by Elizabeth M. Cerkanowicz, executrix

[73] Assignee: New Jersey Institute of Technology, Newark, N.J.

[21] Appl. No.: 246,875

[22] Filed: May 20, 1994

[51] Int. Cl.$^6$ .............................. C04B 7/13; C04B 14/04
[52] U.S. Cl. .................... 106/705; 106/711; 106/737; 106/738; 106/816; 106/DIG. 1; 264/DIG. 49
[58] Field of Search ................... 106/705, 711, 106/738, 737, 816, 817, DIG. 1, 706; 264/DIG. 49

[56] References Cited

U.S. PATENT DOCUMENTS

| 2,250,107 | 7/1941 | Nelles | 106/DIG. 1 |
|---|---|---|---|
| 2,987,406 | 6/1961 | Minnick | 106/DIG. 1 |
| 3,669,703 | 6/1972 | Pennachetti et al. | 106/405 |
| 4,182,191 | 1/1980 | Ikeda | 73/803 |
| 4,210,457 | 7/1980 | Dodson et al. | 106/706 |
| 4,504,320 | 3/1985 | Rizer et al. | 106/DIG. 1 |
| 4,933,013 | 6/1990 | Sakai et al. | 106/DIG. 1 |
| 4,992,102 | 2/1991 | Barbour | 106/DIG. 1 |
| 5,041,987 | 8/1991 | Kuwahara et al. | 364/505 |

FOREIGN PATENT DOCUMENTS

| 2514509 | 4/1983 | France . |
|---|---|---|
| 4020254 | 1/1992 | Germany . |

OTHER PUBLICATIONS

Cabrera et al., "Evaluation of the properties of British Pulverized Fuel Ashes and their influence on the strength of concrete", pp. 116–144 (Date unknown).

Hemmings et al., "Speciation in size and density Fractionated Fly Ash", Mat. Res. Symp. Proc., vol. 65, Oct. 1985, pp. 91–104.

White et al. "Modeling of Fly Ash Concrete Mixtures", Mat. Res. Symp. Proc., vol. 65, Nov. 1985 pp. 243–254.

Jun-Yuan et al., "Hydration of Fly Ash–Portland Cements", Cement & Concrete research, vol. 14, pp. 505–512, 1984 (no month).

Berry et al., "Beneficiated Fly Ash: Hydration, Microstructure, and Strength Development in Portland Cement Systems", pp. 241–273, (Date unknown).

Ukita, et al., "Improvements in the properties of concrete utilizing Classified Fly Ash", SP 114–10 pp. 219–240 (Date unknown).

Ravindrarajah et al., "Properties of concrete containing low calcium Fly Ash under hot & humid climate", SP 114–6, pp. 139–155 (Date unknown).

Sheu et al., "Class F Fine Fly Ash" Mat. Res. Soc. Symp. Proc., vol. 178, pp. 159–166, 1990 (no month).

Fraay, "Fly Ash A Pozzolan in Concrete", (Date Unknown).

(List continued on next page.)

Primary Examiner—Mark L. Bell
Assistant Examiner—Michael Marcheschi
Attorney, Agent, or Firm—Klauber & Jackson

[57] ABSTRACT

The present invention relates to concrete, mortar and other hardenable mixtures comprising cement and fly ash for use in construction. The invention includes a method for predicting the compressive strength of such a hardenable mixture, which is very important for planning a project. The invention also relates to hardenable mixtures comprising cement and fly ash which can achieve greater compressive strength than hardenable mixtures containing only concrete over the time period relevant for construction. In a specific embodiment, a formula is provided that accurately predicts compressive strength of concrete containing fly ash out to 180 days. In other specific examples, concrete and mortar containing about 15% to 25% fly ash as a replacement for cement, which are capable of meeting design specifications required for building and highway construction, are provided. Such materials can thus significantly reduce construction costs.

12 Claims, 33 Drawing Sheets

OTHER PUBLICATIONS

Standard specification For Fly Ash & raw or calcined natural Pozzolan for use as a mineral admixture in Portland Cement Concrete, ASTM, vol. 04-02 Dec. 1989.

Swamy, "Fly Ash Utilization in Concrete Construction", University of Sheffield, pp. 359-367, (Date Unknown).

Carette et al., "Early Age Strength Development of Concrete Incorporating Fly Ash and Condensed Silica Fume", pp. 765-784 (Date Unknown).

Yamato et al., "Shrinkage and Creep of Mass Concrete Containing Fly Ash", pp. 87-102, (Date Unknown).

Lane et al., "Properties and use of Fly Ash in Portland Cement Concrete", pp. 81-92, (Date Unknown).

Giaccio et al., "Concrete incorporating high volumes of ASTM Class F Fly Ash", Amer. Soc. For Testing & Materials, pp. 88-95, 1988 (no month).

"Use of Fly Ash in Concrete", ACI Committee, Committee report, pp. 381-409, ACI Material Journal, Oct. 1987.

Autefage et al., "Comparative Study of the Cementitious Properties of Different Fly Ashes", SP 91-4, pp. 91-114 (Date Unknown).

Giergicnhy et al., "Influence of Fineness of Fly Ashes on their Hydraulic Activity", SP 114-4, pp. 97-115 (Date Unknown).

Ravina, "Optimized Determination of PFA (Fly Ash) Fineness with reference to Pozzolanic Activity", cement & concrete research vol. 10 pp. 573-580, 1980. (no month).

Popovics, "Strength relationship For Fly Ash Concrete", ACI Journal, pp. 43-49, Feb. 1982.

No. 163 (C-0826) Apr. 24, 1991 Patent Abstracts of Japan, vol. 15.

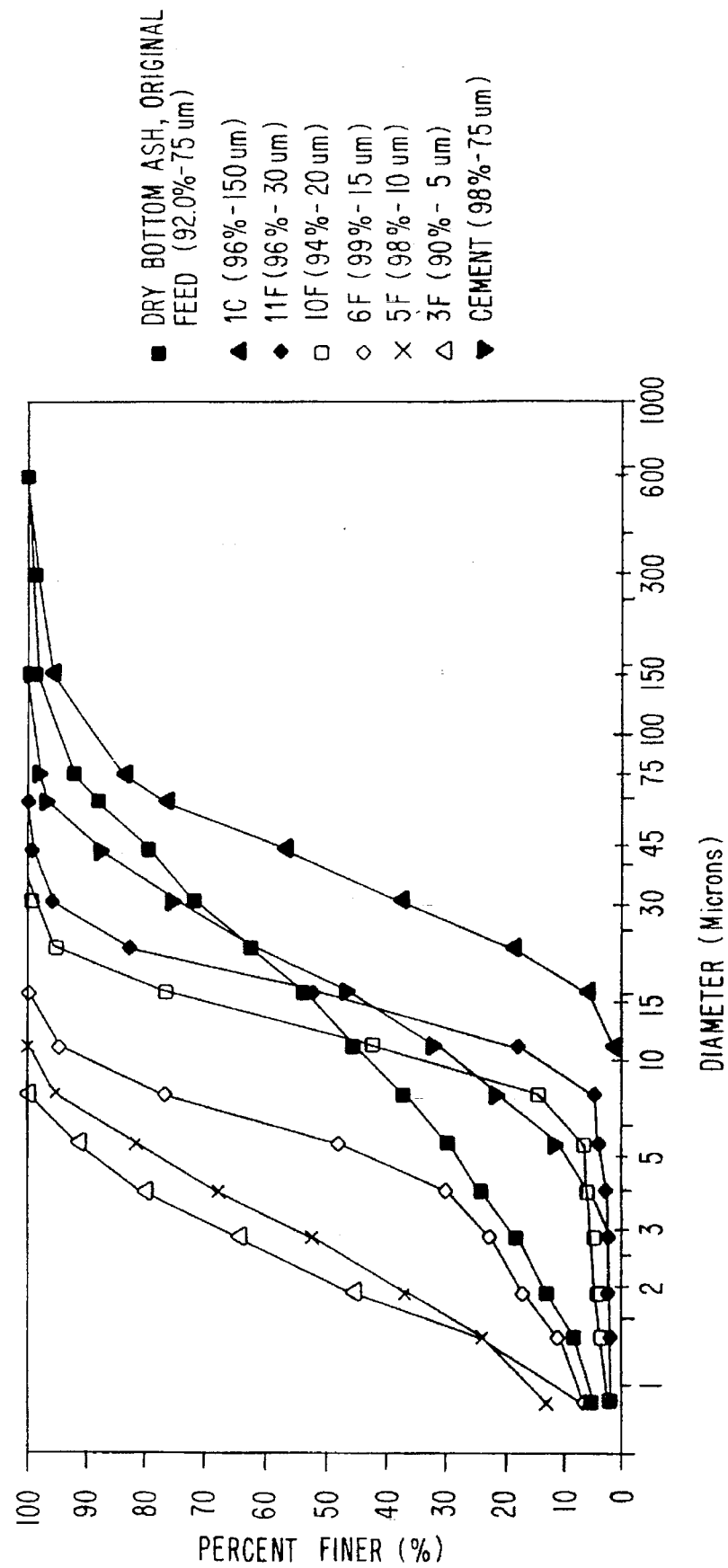

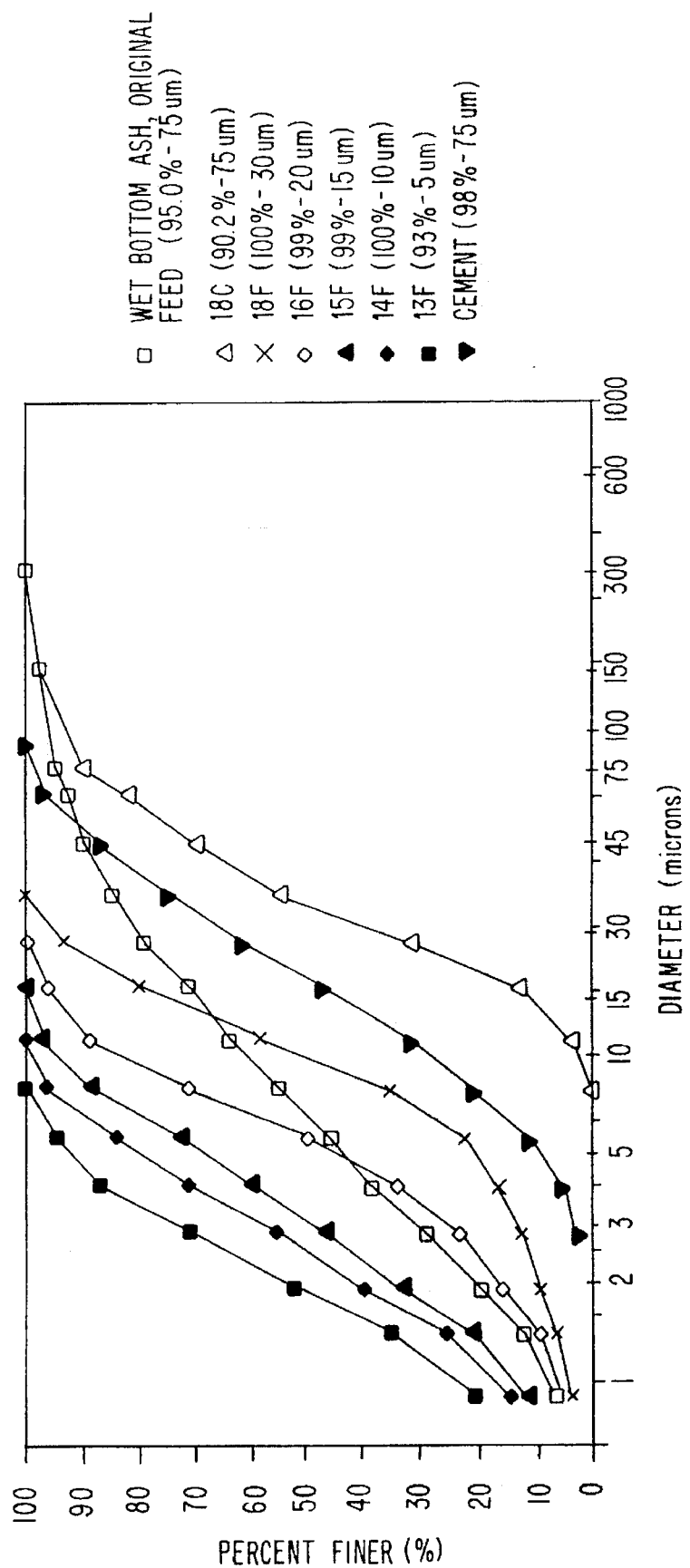
FIG. IB

□ CCCC (CONTROL, NO FLY ASH)
+ 3FC15 (3F FLY ASH, 15% REPLACEMENT)
◇ 6FC1F (5F FLY ASH, 15% REPLACEMENT)
△ 10FC15 (10F FLY ASH, 15% REPLACEMENT)
× 11FC15 (11F FLY ASH, 15% REPLACEMENT)
▽ 1CC15 (1C FLY ASH, 15% REPLACEMENT)
□ CDRY15 (ORIGINAL DRY BOTTOM ASH, 15% REPLACEMENT)

□ CCCC (CONTROL, NO FLY ASH)
+ 3FC35 (3F FLY ASH, 35% REPLACEMENT)
◇ 6FC35 (6F FLY ASH, 35% REPLACEMENT)
△ 10FC35 (10F FLY ASH, 35% REPLACEMENT)
× 11FC35 (11F FLY ASH, 35% REPLACEMENT)
▽ 1CC35 (1C FLY ASH, 35% REPLACEMENT)
□ CDRY35 (ORIGINAL DRY BOTTOM ASH, 35% REPLACEMENT)

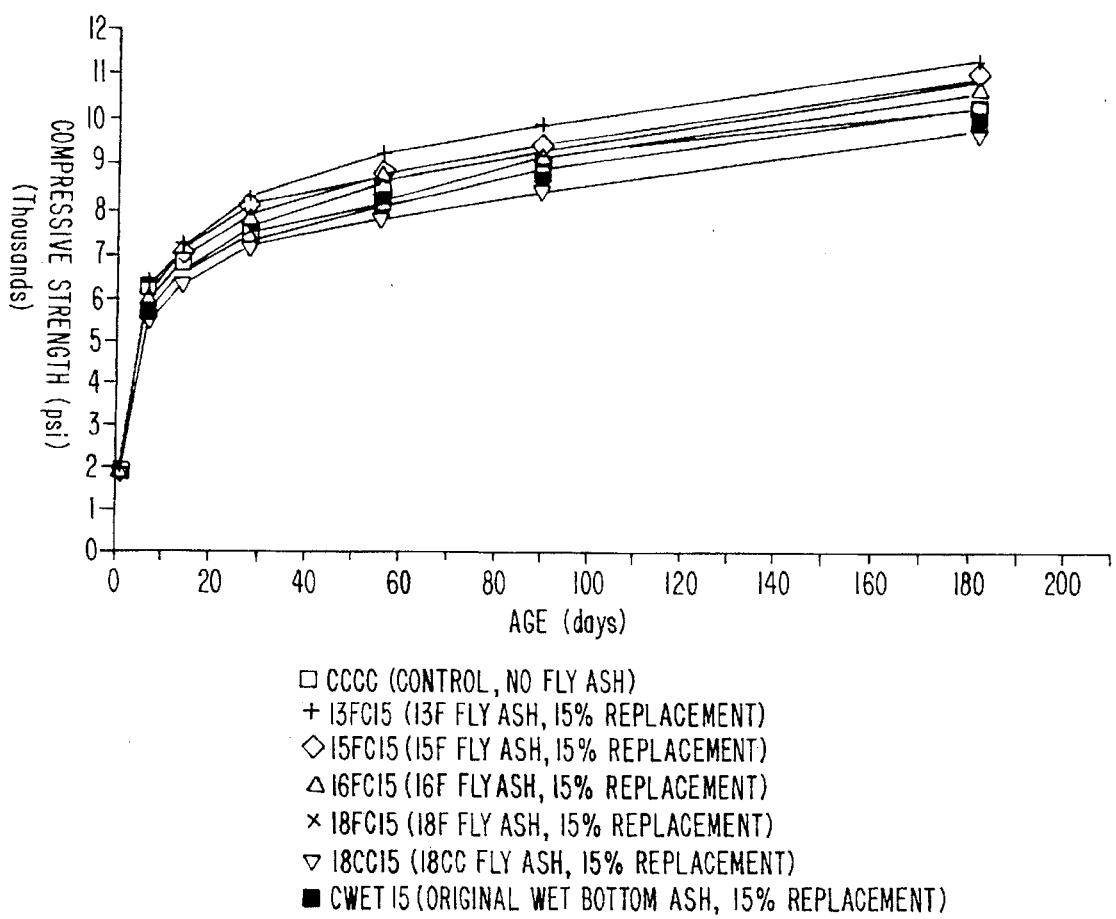

□ CCCC (CONTROL, NO FLY ASH)
+ 13FC35 (13F FLY ASH, 35% REPLACEMENT)
◇ 15FC35 (15F FLY ASH, 35% REPLACEMENT)
△ 16FC35 (16F FLY ASH, 35% REPLACEMENT)
× 18FC35 (18F FLY ASH, 35% REPLACEMENT)
▽ 18CC35 (18C FLY ASH, 35% REPLACEMENT)
■ CWET35 (ORIGINAL WET BOTTOM ASH, 35% REPLACEMENT)

+ CSF15 (15% REPLACEMENT OF SILICA FUME)
△ C3F15 (15% REPLACEMENT OF 3F FLY ASH)
▽ C13F15 (15% REPLACEMENT OF 13F FLY ASH)
□ CSF (CONTROL, NO FLY ASH OR SILICA FUME)

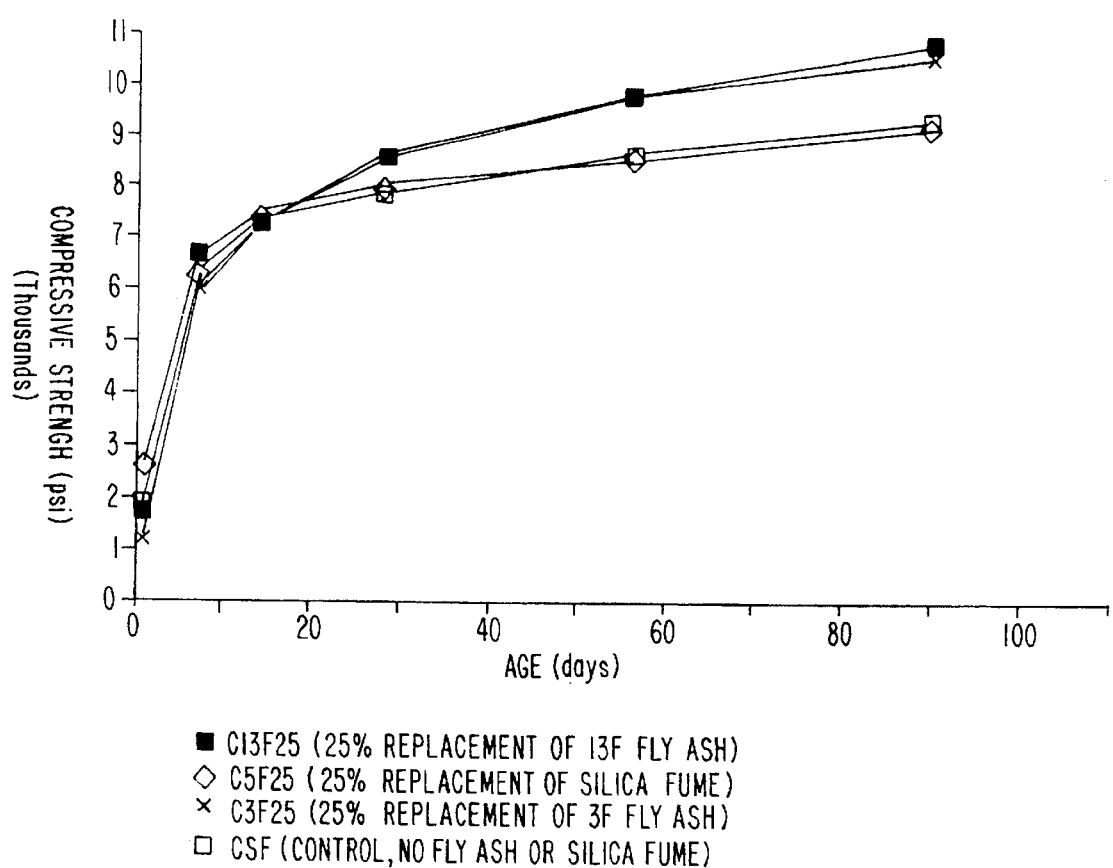

- CF (CONTROL, NO FLY ASH)
- △ 3F25 (25% REPLACEMENT OF 3F FLY ASH)
- ◇ 5F25 (25% REPLACEMENT OF 5F FLY ASH)
- × 10F25 (25% REPLACEMENT OF 10F FLY ASH)
- ▽ 11F25 (25% REPLACEMENT OF 11F FLY ASH)
- □ 1C25 (25% REPLACEMENT OF 1C FLY ASH)
- + DRY25 (25% REPLACENENT OF ORIGNAL FEED DRY BOTTOM ASH)

■ CF (CONTROL, NO FLY ASH)
△ 3F50 (50% REPLACEMENT OF 3F FLY ASH)
◇ 5F50 (50% REPLACEMENT OF 5F FLY ASH)
× 10F50 (50% REPLACEMENT OF 10F FLY ASH)
▽ 11F50 (50% REPLACEMENT OF 11F FLY ASH)
□ IC50 (50% REPLACEMENT OF IC FLY ASH)
+ DRY50 (50% REPLACEMENT OF ORIGINAL FEED DRY BOTTOM ASH)

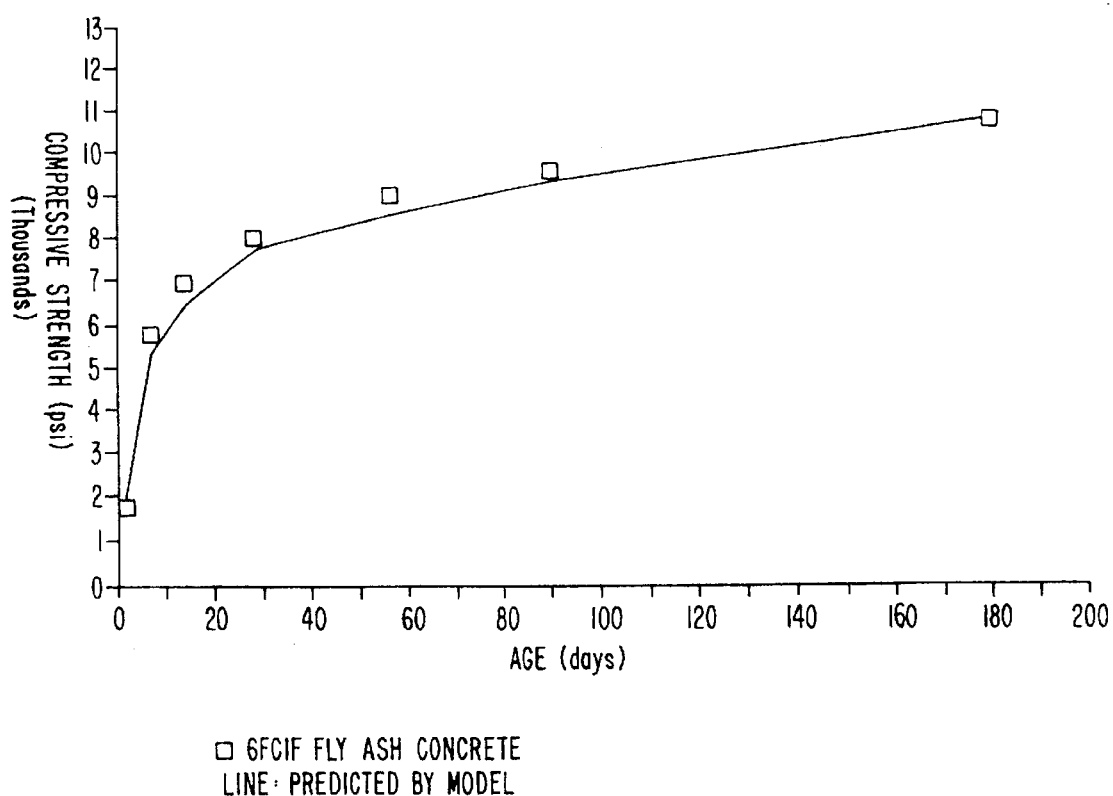
FIG. IIA

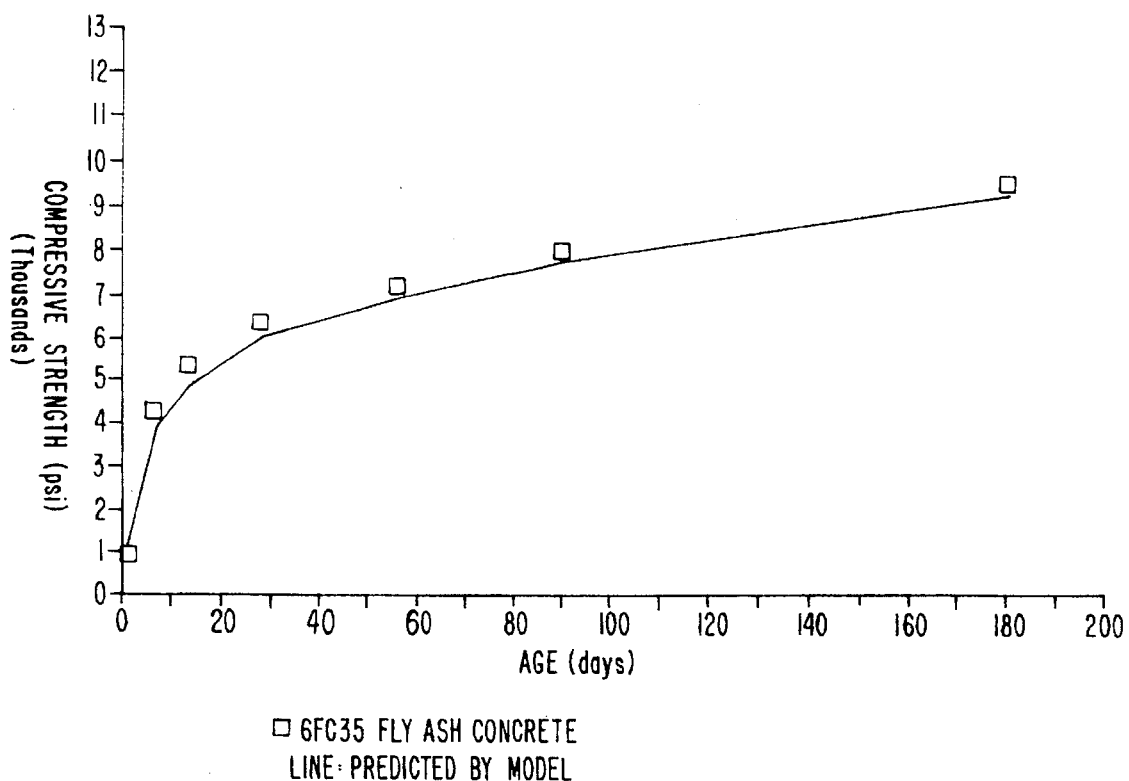
FIG. IIC

□ 6FC50 FLY ASH CONCRETE
LINE: PREDITED BY MODEL

□ 16FC25 FLY ASH CONCRETE
LINE: PREDICTED BY MODEL

□ 16FC35 FLY ASH CONCRETE
LINE: PREDICTED BY MODEL

□ 16FC50 FLY ASH CONCRETE
LINE: PREDICTED BY MODEL

COMPRESSIVE STRENGTH OF CONCRETE AND MORTAR CONTAINING FLY ASH

The research leading to the present invention was conducted with Government support under Contract No. DE-FG22-90PC90299 awarded by the Department of Energy. The Government has certain rights in this invention.

FIELD OF THE INVENTION

The present invention relates to concrete, mortar and other hardenable mixtures comprising cement and fly ash for use in construction. The invention includes a method for predicting the compressive strength of such a hardenable mixture, which is very important for planning a project. The invention also relates to hardenable mixtures comprising cement and fly ash which can achieve greater compressive strength than hardenable mixtures containing only concrete over the time period relevant for construction.

BACKGROUND OF THE INVENTION

Fly ash, a by-product of coal burning power plant, is produced worldwide in large quantities each year. In 1988, approximately 84 million tons of coal ash were produced in the U.S. in the form of fly ash (60.7%), bottom ash (16.7%), boiler slag (5.9%), and flue gas desulfurization (16.7%) (Tyson, 1990, Coal Combustion By-Product Utilization Seminar, Pittsburgh, 15 pp.). Out of the approximately 50 million tons of fly ash generated annually, only about 10 percent is used in concrete (ACI Committee 226, 1987, "Use of Fly Ash In Concrete," ACI 226.3R-87, ACI J. Proceedings 84:381–409) while the remaining portion is mostly disposed of as waste in landfills.

It is generally more beneficial for a utility to sell its ash, even at low or subsidized prices, rather than to dispose of it in a landfill, since this will avoid the disposal cost. In the 1960's and 70's the cost of ash disposal was typically less than $1.00 per ton. However, due to the more stringent environmental regulations starting in the late 1970's, the cost of ash disposal has rapidly increased to from $2.00 to $5.00 per ton and is still rising higher (Bahor and Golden, 1984, Proceedings, 2nd International Conference on Ash Technology and Marketing, London, pp. 133–136). The shortage of landfill due to environmental concerns has further escalated the disposal cost. The Environmental Protection Agency (EPA) estimated in 1987 that the total cost of waste disposal at coal fired power plants ranged from $11.00 to $20.00 per ton for fly ash and bottom ash (Courst, 1991, Proceedings: 9th Int'l 1.0 Ash Use Symposium, 1:21–1 to 21–10). This increasing trend of disposal cost has caused many concerns and researchers are urgently seeking means for better utilization of fly ash. One potential outlet for fly ash is incorporation in concrete or mortar mixtures.

Fly ash is used in concrete in two distinct ways, one as a replacement for cement and the other as a filler. The first use takes advantage of the pozzolan properties of fly ash, which, when it reacts with lime or calcium hydroxide, can enhance the strength of cementitious composites. However, fly ash is relatively inert and the increase in compressive strength can take up to 90 days to materialize. Also, since fly ash is just a by-product from the power industry, the quality of fly ash has always been a major concern to the end users in the concrete industry.

Incorporation of fly ash in concrete improves workability and thereby reduces the water requirement with respect to the conventional concrete. This is most beneficial where concrete is pumped into place. Among numerous other beneficial effects are reduced bleeding, reduced segregation, reduced permeability, increased plasticity, lowered heat of hydration, and increases setting times (ACI Committee 226, 1987, supra). The slump is higher when fly ash is used (Ukita et al., 1989, SP-114, American Concrete Institute, Detroit, pp.219–240).

However, the use of fly ash in concrete has many drawbacks. For example, addition of fly ash to concrete results in a product with low air entrainment and low early strength development.

As noted above, a critical drawback of the use of fly ash in concrete is that initially the fly ash significantly reduces the compressive strength of the concrete. Tests conducted by Ravindrarajah and Tam (1989, Fly Ash, Silica Fume, Slag, and Natural Pozzolans in Concrete, SP-114, American Concrete Institute, Detroit, pp. 139–155) showed that the compressive strength of fly ash concrete at early ages are lower than those for the control concrete, which is a general property of concrete or mortar when fly ash is added. Most of the reported studies tend to show a lower concrete strength due to the presence of fly ash; none has yet suggested a solution to actually enhance the property of concrete economically. Yet, for fly ash to be used as a replacement for cement, it must be comparable to cement in terms of strength contribution at a point useful in construction. As a practical matter, this means that the fly ash concrete must reach an acceptable compressive strength within about 2 weeks.

Swamy (1984, Proceedings, 2nd Int'l Conference on Ash Technology and Marketing, London, pp. 359–367) showed that 30% replacement by weight, and inclusion of a high dose of a superplasticizer, yielded concrete with material properties and structural behavior almost identical to those of concrete of similar strength without fly ash. However, due to the high cost of superplasticizer, mix proportions were not economical.

Fly ashes from different sources may have different effect to concrete. The same fly ash may behave differently with portland cements of different types (Popovics, 1982, ACI J. Proceedings 79:43–49), since different types of portland cement (type I to V) have different chemical composition. Other factors relating to the effects of fly ash on concrete that are not presently understood are lime availability, the rate of solubility and reactivity of the glassy phase in different fly ash, and the proper mix proportion to ensure early strength development of fly ash concrete.

Fly ash particles are typically spherical, ranging in diameter from 1 to 150 microns (Berry and Malhotra, 1980, ACI J. Proceedings 77:59–73). Aitcin et al. (1986, Fly Ash, Silica Fume, Slag, and Natural Pozzolans in Concrete, SP-91, American Concrete Institute, Detroit, pp. 91–113) showed that if the average diameters, $D_{50}$, of fly ash are smaller, the surface area of the fly ash will be larger than those with larger average diameters.

Many factors affect the size or average diameter of fly ash, including storage conditions, ash collection processes, and combustion conditions. Combustion conditions are perhaps most important, because these determine whether carbon remains in the ash or if combustion is complete.

There are two main forms of combustion: dry bottom boiler combustion and wet bottom boiler combustion. The main difference between the two types of boiler is that wet bottom boilers reach the fusion temperature of ash, thus resulting in fly ash with greater glass characteristics.

There are generally two methods known to measure the fineness of fly ash. The first is by measuring the residue on the 45 micron (No. 325 sieve), which is the method used in the United States. The second method is the surface area method by air permeability test. Lane and Best (1982, Concrete Int'l: Design & Construction 4:81–92) suggested that 45 microns sieve residue is a consistent indicator of pozzolanic activity. For use in concrete or mortar, ASTM C 618 (1990, ASTM C 618-89a, *Annual Book of ASTM Standards*, Vol. 04.02) specifies that not more than 34% by weight of a given fly ash be retained on a 45 microns sieve. However, Ravina (1980, Cement and Concrete Research 10:573–580) reported that specific surface area provides a more accurate indicator of pozzolanic activity.

Research carried out by Ukita et al. (1989, supra) purported that as the percentage of finer particles, i.e., those particles ranging from diameters of 1 to 20 microns, in concrete increases, the corresponding strength gain is notable. Similar observations have been reported by Giergiczny and Werynska (1989, Fly Ash, Silica Fume, Slag, and Natural Pozzolans in Concrete, SSP-114, American Concrete Institute, Detroit, pp. 97–115).

Both of the groups mentioned above describe results with fly ash of disparate characteristics and sources, but did not include controls for these variable. Thus, although the emphasis of these reports is on the performance of finer particle fly ashes, the variables introduced into the studies lead to reservations with respect to any conclusions that may be drawn. In particular, Ukita et al. (1989, supra) collected fly ash from different locations. However, an earlier report demonstrated that fly ashes collected from different locations have different chemical properties (Liskowitz et al., 1983, "Sorbate Characteristic of Fly Ash," Final Report. U.S. Dept. of Energy, Morgantown Energy Technology Center, p. 211 ). Giergiczny and Werynska (1989, supra) ground the original fly ash into different sizes. Grinding can add metal particles into the fly ash, and also tends to yield unnaturally shaped particles of fly ash. Thus, these reports fail to provide conclusive information about the effect of fine particle size on the properties imparted by fly ash.

Berry et al. (1989, Fly Ash, Silica Fume, Slag, and Natural Pozzolans in Concrete, SP-114, American concrete Institute, Detroit, pp. 241–273) studied the properties of fly ash with particle size smaller than 45 microns, so called "beneficiated" fly ash, in mortar. Fly ashes of this particle size showed improved pozzolanic activity, reduced water demand and enhanced ability to reduce alkaliaggregate reactivity.

Although beneficiated fly ash seem to show promising results in terms of improved performance of mortar, other researchers concluded otherwise when used in concrete. Giaccio and Malhotra (1988, Cement, Concrete, and Aggregates 10:88–95) also conducted the test using the beneficiated fly ashes. They showed that the concrete made with ASTM type I cement, the use of beneficiated fly ash and condensed silica fume did little to enhance the properties of concrete compared with the raw fly ash.

It is critically important in construction to have concrete or mortar that predictably achieves required performance characteristics, e.g., a minimum compressive strength within 14 days. A corollary is that a construction or civil engineer must be able to predict the compressive strength of a concrete or mortar mixture after a given period of time. However, the prior art concrete or mortar mixtures that contain fly ash lack predictability with respect to compressive strength, and generally have lower compressive strength than concrete or mortar mixtures that lack fly ash. Therefore, there has been a disincentive to use fly ash in such hardenable mixtures.

Thus, there is a need in the art for a method of quantitatively determining the rate of strength gain of a concrete or mortar containing fly ash.

There is a further need in the art for high strength concrete and mortar containing fly ash.

There is yet a further need in the art for the utilization of fly ash generated during coal combustion.

The citation or identification of any reference in this application shall not be construed as an admission that such reference is available as prior art to the present invention.

SUMMARY OF THE INVENTION

In a first aspect, the present invention provides a method for predicting the compressive strength of a hardenable mixture containing cement and fly ash of a defined fineness comprising determining the contribution to compressive strength of 1. the compressive strength contributed by the cement over a given period of time, which is a function of the concentration of cement; and
2. the compressive strength contributed by the fly ash of a defined fineness over a given period of time, wherein the fineness is either a distribution of fly ash particle sizes or a distribution of fly ash particle volumes.

According to the invention, the compressive strength contributed by the fly ash of a defined fineness is a function of the fineness of the fly ash, the concentration of fly ash in the mixture, and the age of the hardenable mixture in days.

One measure of fineness of the fly ash is referred to herein as the fineness modulus, which is a measure of the distribution of particle sizes (e.g., diameter) or the distribution of particle volumes. In a specific embodiment, the fineness modulus is the summation of the percentage of fly ash that retains on more than one sieves of different sizes ranging from about 1µ to about 300µ.

A particular advantage of the present invention is that in a preferred aspect it provides a highly quantitative measure of fineness of fly ash, which measure can be used to accurately predict the compressive strength of a hardenable mixture at a given time.

In a specific embodiment, the compressive strength of the hardenable mixture is determined as a percentage compressive strength of the hardenable mixture compared to a control hardenable mixture that does not contain fly ash. In a more particular aspect, the percentage compressive strength, σ(%), is calculated according to the following formula:

$$\sigma(\%) = 0.010 C^2 + A + (B/FM)\ln(T),$$

wherein C is the percentage of cement in cementitious materials present in the hardenable mixture, which cementitious materials include cement and fly ash; A is a constant for the contribution of fineness of fly ash to the strength of the hardenable mixture: B is the constant for pozzolanic activity rate between fly ash and cement, which is proportional to the content of fly ash in the mixture; FM is the fineness modulus of the fly ash, which is the summation of the percentage of fly ash that retains on more than one sieves of different sizes ranging from about 1µ to about 300µ; and T is the age of the hardenable mixture in days, wherein T ranges from 1 day to about 180 days. In a specific embodiment, infra, the formula was used to accurately predict compressive strength at various time points up to 180 days.

In specific embodiments, the fly ash is either wet bottom boiler fly ash or dry bottom boiler fly ash, and $A=6.74-0.00528FM$.

In other embodiments, the fly ash content of the hardenable mixture is between about 10% to about 50% by weight of cementitious materials in the mixture, and $B=(1685+126C-1.324C^2)$.

In a preferred aspect of the invention, the fly ash is wet bottom boiler fly ash or dry bottom boiler fly ash, the fly ash content of the hardenable mixture is between about 10% and about 50%, and $\sigma(\%)=0.010C^2+(6.74-0.00528FM)+\{(1685+126C-1.324C^2)/FM\}ln(T)$.

In a further aspect, the present invention provides hardenable mixtures containing cement and fly ash that has been fractionated into a defined fineness. The hardenable mixtures of the invention advantageously have predictable compressive strengths. Preferably, the hardenable mixtures of the invention have the same or greater performance characteristics, such as compressive strength after 7 to 14 days of hardening, as a comparable hardenable mixture that does not include fly ash. Hardenable mixtures of the invention with enhance performance characteristics comprise fly ash characterized by a distribution of particle sizes or particle volumes that is less than the median or average for non-fractionated fly ash. Hardenable mixtures according to the invention include, but are not limited to, concrete and mortar.

Accordingly, the present invention particularly relates to a concrete comprising about 1 part by weight cementitious materials, about 1 to about 3 parts by weight fine aggregate, about 1 to about 5 parts by weight coarse aggregate, and about 0.35 to about 0.6 parts by weight water, wherein the cementitious materials comprise from about 10% to about 50% by weight fly ash and about 50% to about 90% by weight cement, wherein the fly ash has a fineness modulus of less than about 600, wherein the fineness modulus is calculated as the sum of the percent of fly ash retained on sieves of 0, 1, 1.5, 2, 3, 5, 10, 20, 45, 75, 150, and 300 microns. Preferably, the fly ash is wet bottom boiler fly ash having a fineness modulus of less than about 350 as calculated above.

In a further embodiment, the invention relates to a mortar comprising about 1 part by weight cementitious materials, about 1 to about 3 parts by weight fine aggregate, and about 0.35 to about 0.6 parts by weight water, wherein the cementitious materials comprise from about 10% to about 50% by weight fly ash and about 50% to about 90% by weight cement, wherein the fly ash has a fineness modulus of less than about 600, wherein the fineness modulus is calculated as the sum of the percent of fly ash retained on sieves of 0, 1, 1.5, 2, 3, 5, 10, 20, 45, 75, 150, and 300 microns. Preferably, the fly ash is a wet bottom boiler fly ash having a fineness modulus of less than about 350, as calculated above.

As can be appreciated from the foregoing, the present invention advantageously provides hardenable mixtures in which fly ash, a very inexpensive material, replaces cement in the cementitious materials, substantially decreasing the cost of the hardenable mixture without sacrificing performance characteristics. In a further aspect, the present invention provides hardenable mixtures with enhanced performance characteristics at a lower price.

The invention further advantageously provides concrete and mortar mixtures comprising fly ash that do not require an expensive superplasticizer. Prior art mixtures require superplasticizer permit a reduction in the amount of water in the mixture, thus compensating for the decrease in compressive strength of the mixture due to addition of the fly ash. Thus, the invention provides concrete or mortar substantially lacking a plasticizer.

According to the invention, the fine aggregate used in the cement or the mortar can comprise a sand and a fly ash, wherein a ratio by weight of sand to fly ash is from about 4:1 to about 1:1, and the fly ash has a fineness modulus of less than about 600, wherein the fineness modulus is calculated as the sum of the percent of fly ash retained on sieves of 0, 1, 1.5, 2, 3, 5, 10, 20, 45, 75, 150, and 300 microns.

In a further aspect, fly ash can be used as an additive in a hardenable mixture, wherein the ratio of additive fly ash to cement of ranges from about 1:10 to about 1:1, and wherein the ratio of the total amount of fly ash (whether included as a cementitious material, a fine aggregate substitute, or as an additive) ranges from about 1:5 to about 2:1. Preferably, the fly ash has a fineness modulus of less than about 600, wherein the fineness modulus is calculated as the sum of the percent of fly ash retained on sieves of 0, 1, 1.5, 2, 3, 5, 10, 20, 45, 75, 150, and 300 microns.

Thus, the invention provides for use of fractionated fly ash of a defined fineness to replace cement in the cementitious materials of a hardenable mixture, to replace sand or other fine aggregate of a hardenable mixture, or as an additive, which mixtures have predictable performance characteristics, demonstrate performance characteristics that meet or exceed the standards required for construction, and cost significantly less than equivalent compositions that lack fly ash. The invention further provides a method for predicting the compressive strength of such hardenable mixtures.

BRIEF DESCRIPTION OF THE DRAWINGS

FIG. 1 presents graphs showing the size distribution of fractionated fly ash particles and cement particles (inverted triangles, 98% of which have a diameter of 75µ or less). (A) Dry bottom boiler fly ash (solid square, in which 92% of the particles have a diameter of 75µ or less) and fractions 1C (solid triangle, 95% less than 150µ), 11F (solid diamond, 96% less than 30µ), 10F (open square, 94% less than 20µ), 6F (open diamond, 99% less than 15µ), 5F (X, 98% less than 10µ), and 3F (open triangle, 90% less than 5µ). (B) Wet bottom boiler fly ash (open square, 95% less than 75µ) and fractions 18C (open triangle, 90.2% less than 75µ), 18F (X, 100% less than 30µ), 16F (open diamond, 99% less than 20µ), 15F (99% less than 15µ), 14F (solid diamond, 100% less than 10µ) and 13F (solid square, 93% less than 5µ). Fly ash from dry or wet bottom boilers was collected and fractionated into six different size distribution fractions as described in the Examples, infra.

DETAILED DESCRIPTION OF THE INVENTION

Figure 2A:
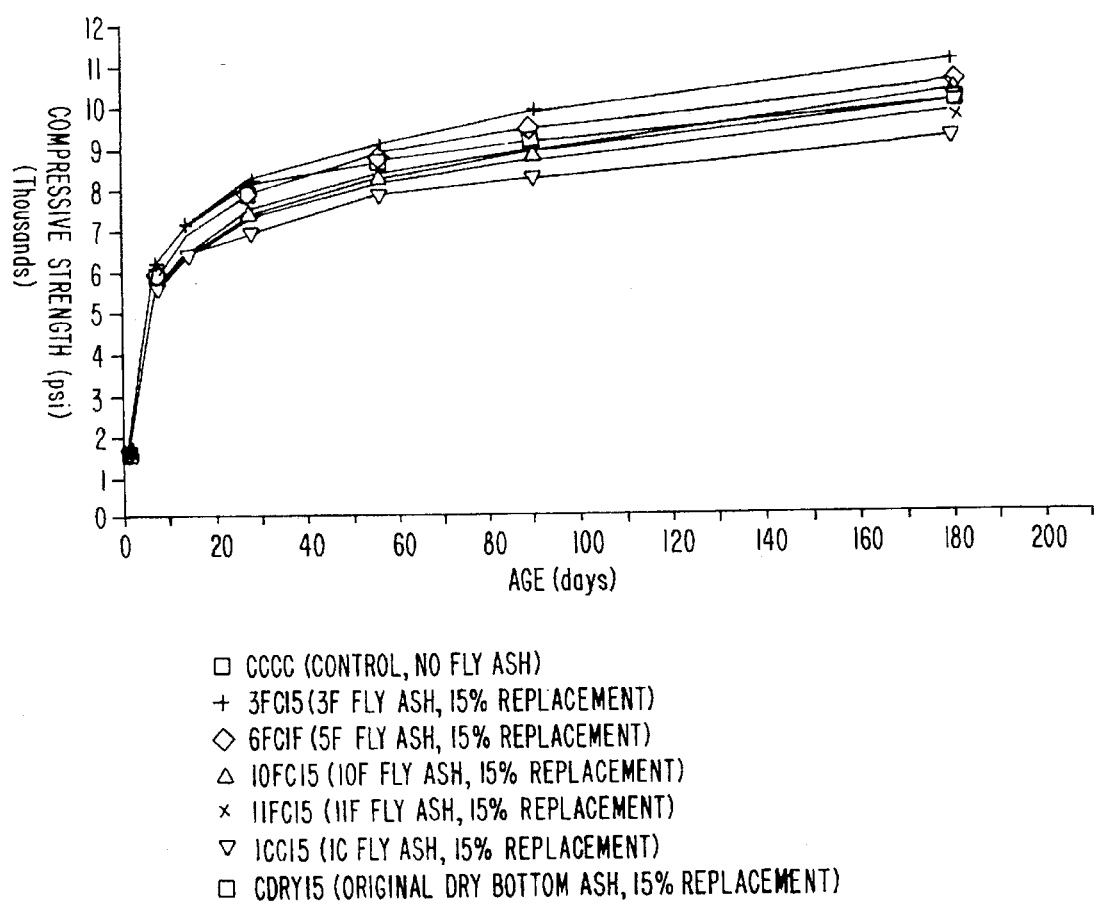
FIG. 2 is a graph showing the compressive strength of concrete with age. The concrete samples contain dry bottom boiler fly ash or fractionated dry bottom boiler fly ash as a replacement for 15% (A), 25% (B), 35% (C) and 50% (D) of the cement in the concrete, compared to a standard containing cement but no concrete (open squares). Samples contain the fractionated fly ash samples as described in FIG. 1 and the Examples: 3FCxx (plus-sign, 3F fly ash fraction, xx stands for the percentage of fly ash used to replace cement); 6FCxx (open diamond, 6F fly ash fraction); 10FCxx (open triangle, 10F fly ash fraction); 11FCxx (X, 11F fly ash fraction); 1CCxx (open inverted triangle, 1C fly ash fraction); and CDRYxx (open square [uniformly of lower compressive strength at each time point than the control sample], original dry bottom boiler fly ash feed).

As described above, the present invention relates to hardenable mixtures comprising fly ash of a defined fineness as a replacement for cement in cementitious materials, which hardenable mixtures achieve compressive strength that is about equal to or greater than the compressive strength of the same hardenable mixture without fly ash. The invention further provides for replacement of a portion of the fine aggregates in a hardenable mixture with fly ash of a defined fineness. The invention further relates to methods for predicting the compressive strength of a hardenable mixture comprising fly ash, based on the degree of fineness of the fly ash. In particular embodiments, the hardenable mixture can be concrete or mortar, as hereinafter defined.

Throughout this specification, where specific ratios, percentages, or proportions are mentioned, they are determined by weight and not by volume.

The present invention is based, in part, on the observation that regardless of the source and chemical composition of fly ash, the pozzolanic properties of the fly ash primarily depend on the degree of fineness of the fly ash. It has been surprisingly found that fractionation of fly ash into fractions of a defined fineness modulus as herein defined provides a high degree of quality control, regardless of the classification or combustion conditions of the fly ash.

As used herein, the term "fly ash" refers to a solid material having a chemical composition similar to or the same as the composition of the material that is produced during the combustion of powdered coal. In a specific aspect, the solid material is the material remaining after the combustion of powdered coal. ACI Committee 116 (1990, ACI 116–85, *ACI Manual of Concrete Practice Part I*, American Concrete Institute, Detroit) defines fly ash as "the finely divided residue resulting from the combustion of ground or powder coal which is transported form the firebox through the flue gases", and the term "fly ash" as used herein encompasses this definition. Generally, fly ash derived from various coals have differences in chemical composition, but the principal components of fly ash are $SiO_2$ (25% to 60%), $Al_2O_3$ (10% to 30%), and $Fe_2O_3$ (5% to 25%). The MgO content of fly ash is generally not greater than 5%. Thus, the term fly ash generally refers to solid powders comprising from about 25% to about 60% silica, from about 10% to about 30% $Al_2O_3$, from about 5% to about 25% $Fe_2O_3$, from about 0% to about 20% CaO, and from about 0% to about 5% MgO.

The term "fly ash" further contemplates synthetic fly ash, which may be prepared to have the same performance characteristics as fly ash as described herein.

Presently, fly ash is classified primarily in two groups: Class C and Class F, according to the ASTM C 618 (1990, supra). Class F is generally produced by burning anthracite or bituminous coal, and Class C results from sub-bituminous coal or lignite. Generally, the fly ash from the combustion of sub-bituminous coals contains more CaO and less $Fe_2O_3$ than fly ash from bituminous coal (Berry and Malhotra, 1980, ACI J. Proceedings 77:59–73). Thus, the CaO content of the Class C fly ash is usually higher than 10%, with the sum of the oxides of $SiO_2$, $Al_2O_3$ and $Fe_2O_3$ not less than 50%. For Class F fly ash the CaO content is normally less than 10% and the sum of the above mentioned oxides is not less than 70%.

The glassy phase of fly ash depends essentially on the combustion conditions and type of boiler. Non-fractionated fly ash obtained from different boilers, such as dry bottom boilers or wet bottom boilers, has been found to behave differently. Boilers that achieve higher temperature yield fly ash with a more developed or pronounced glassy phase. Alternatively, combustion in the presence of a fluxing agent, which reduces the fusion temperature of the fly ash, can also increase the glassy phase of fly ash produced by combustion for lower temperature boilers. Compressive strength of a hardenable mixture containing fly ash may depend in part on the glassy phase of the fly ash, so generally fly ash produced for higher temperature boilers, or produced in the presence of a fluxing agent, or both, may be preferred. However, as demonstrated herein, the fineness modulus is the most important paramter for compressive strength, and fractionated fly ash from any source, with a defined fineness modulus, can be used according to the invention.

Although fly ash generally comes in a dry and finely divided form, in many instances, due to weathering and transportation processes, fly ash becomes wet and often forms lumps. Such fly ash can be less reactive.

Pozzolan, as defined by ASTM C 593 (1990, ASTM C 593-89, Annual Book of ASTM Standards, Vol. 04.02), is "a siliceous or alumino-siliceous material that in itself possesses little or no cementitious value but that in finely divided form and in the presence of moisture will chemically react with alkali and alkaline earth hydroxides at ordinary temperatures to form or assist in forming compounds possessing cementitious properties."

The present invention relates to the determination of the fineness modulus of fractionated fly ash. As used herein, the term "fineness modulus" refers to a measure of the distribution of volumes of particles of fly ash or distribution of particle sizes of the fly ash. According to the present invention, the fineness modulus is a distribution analysis that is much more informative than an average or median partical diameter determination or total surface area determination. The value of fineness modulus corresponds to the fineness of a fraction of fly ash, or to non-fractionated fly ash. Thus, a fraction of fly ash containing a distribution of particles having smaller size, e.g., a median diameter that falls within a smaller range set, will have a fineness modulus value that is lower than a fraction of fly ash containing a distribution of particles having somewhat larger size, e.g., a median diameter that falls within a larger range set, or non-fractionated fly ash. According to the present invention, lower values of fineness modulus are preferred, since hardenable mixtures that contain fractions having a lower fineness modulus achieve compressive strength gains more rapidly. In another embodiment, larger values of fineness modulus may be preferred, where a slower rate of compressive strength gain may be desired.

Thus, the present invention is directed, in part, to use of fractionated fly ash, in which the fly ash particles in any given fraction have a more uniform distribution of volumes or sizes than non-fractionated fly ash.

Preferably, the fineness modulus is determined as the sum of the percentage of fly ash remaining on each of a series of different sized sieves. Accordingly, the term "fineness modulus" refers to a relative value, which can vary depending on the series of sieves chosen. Since, according to the instant invention, fly ash particles of smaller size or diameter are preferred for use in hardenable mixtures, more accurate determinations of fineness modulus are available if a series of smaller sieves are chosen. Preferably, the size of the sieves is predominantly below 10μ, e.g., the sieves may be 0.5, 1, 2, 3, 4, 5, 6, 7, 8 and 10 microns, with sieves ranging up to 300 microns being useful. The number of sieves sized 10 microns or less should be at least one more than the number of sieves sized greater than 10 microns. In a preferred embodiment, the number of sieves sized 10 microns or less in at least five. Although in a specific embodiment, dry seives are used to calculate a value for the fineness modulus, other methods, such as wet seiving, can also be used.

The greater the number of sieves sized 10 microns or less, the greater the absolute value of fineness modulus. Accordingly, where sieves of 0.5, 1, 2, 3, 4, 5, 6, 7, 8, and 10 microns are used, the fineness modulus will be a higher absolute number, reflective of the greater degree of accuracy of determination of this value for the smaller diameter or smaller size fly ash particles.

It has been found that other descriptions of fly ash, such as percent retention on a 45μ (No. 325) sieve, are too crude to provide an accurate and quantitative value for estimating compressive strength gain, or for preparing a hardenable mixture that has satisfactory compressive strength. Similarly, it has been found that a measure such as the Blaine fineness, which is actually a determination of the average surface area of fly ash particles somewhat proportional to, but not congruent to size or volume, is also not useful for predicting compressive strength gain, or for preparing a hardenable mixture that has satisfactory compressive strength. In a specific example, infra, compressive strength is independent of Blaine fineness at a Blaine fineness of greater than about 4000 $cm^2/g$, when fractionated fly ash is used to replace 35% of the cement, whereas compressive strength varies with median diameter over the entire range of diameters tested.

Although not intending to be bound by any particular theory or hypothesis, it is believed that dissolution of fly ash in a hardenable mixture, whereby the pozzolanic properties of the fly ash can contribute to compressive strength of the hardenable mixture, is acutely dependent on the size distribution of the fly ash to a certain minimum size. The data disclosed in the Examples, infra, support a conclusion that the fly ash contribution to compressive strength of a hardenable mixture depends on the distribution of particle volumes, or sizes. Above a minimum size, the contribution diminishes. Below this minimum size, strength of the concrete appears to be independent of size. Most surprising is the discovery that size, rather than surface area, e.g., as measured as Blaine fineness, is the more critical factor. This observation is surprising because the surface area hypothetically determines the reactivity of a particle, since surface functional groups are presumably more available for reaction.

The pozzolanic reaction of fly ash in a hardenable mixture comprising cement is the reaction between constituents of the fly ash and calcium hydroxide. It is generally assumed to take place on the surface of fly ash particles, between silicates and aluminates from the glass phase of the fly ash and hydroxide ion in the pore solution (Plowman, 1984, Proceedings, 2nd Int'l Conference on Ash Technology and Marketing, London, pp. 437–443). However, the result of the research leading to the present invention undicates that thte pozzolanic reactions of the ash are dependent on the folumen of the fly ash aprticles: the smaller the particle volumen, the more rapidly it completes its reaction with the cement to contribute to compressive strength. The rate of solubility and reactivity of these glassy phases in different types of fly ash depends on the glassy phase of fly ash, which in turn depends on the combustion temperature of the boiler that produced the fly ash. In addition to the effect of combustion conditions on the glassy phase of fly ash, different fly ashes from one class can behave differently, depending on the $SiO_2$, $Al_2O_3$ and $Fe_2O_3$ content, and other factors such as the particle size distribution and storage conditions of the ash (see Aitcin et al, 1986, supra; Liskowitz et al., 1983, supra).

During hydration, portland cement produces a surfeit of lime (CaO) that is released to the pore spaces. It is the presence of this lime that allows the reaction between the silica components in fly ash and calcium hydroxide to form additional calcium silicate hydrate [C—S—H]. He et al. (1984, Cement and Concrete Research 14:505–511) showed that the content of crystalline calcium hydroxide in the fly ash-portland cement pastes decreases as a result of the addition of fly ash, most likely resulting from a reaction of calcium with alumina and silica from fly ash to form addition C—S—H. This process stabilizes the concrete, reduces permeability and increases resistance to chemical attacks.

Fractionation of fly ash can be accomplished by any means known in the art. Preferably, fractionation proceeds with an air classifying system. In a specific embodiment, infra, a MICRO-SIZER air classifying system was used to fractionate fly ash in six different particle size ranges. In another embodiment, the fly ash can be fractionated by sieving. For example, a 45μ or smaller sieve can be used to select for particles of a defined maximum size. In a further embodiment, the fly ash can be ground to a desired size or fineness. However, this method is not preferred, as the grinding process yields non-uniform particles and may introduce metallic or other impurities from the grinder itself.

The term "cement" as used herein refers to a powder comprising alumina, silica, lime, iron oxide and magnesia burned together in a kiln and finely pulverized, which upon mixing with water binds or unites other materials present in the mixture in a hard mixture. Thus, the hardenable mixtures of the invention comprise cement. Generally, the term cement refers to hydraulic cements such as, but not limited to, portland cement, in particular portland type I, II, III, IV and V cements.

As used herein, the term "cementitious materials" refers to the portion of a hardenable mixture that provides for binding or uniting the other materials present in the mixture, and thus includes cement and pozzolanic fly ash. Fly ash can comprise from about 5% to about 50% of the cementitious materials in a hardenable mixture of the invention; preferably, fly ash comprises from about 10% to about 35% of cementitious materials. The balance of cementitious materials will generally be cement, in particular Portland cement. In a specific embodiment, infra, the hardenable mixtures of the invention comprise portland type I cement.

The term "concrete" refers to a hardenable mixture comprising cementitious materials; a fine aggregate, such as sand: a coarse aggregate, such as but not limited to crushed basalt coarse aggregate; and water. Concrete of the invention further comprises fly ash having defined fineness. In a specific embodiment, the fly ash makes up from about 10% to about 50% of the cementitious materials. In a further aspect, the fly ash is used as fine aggregate in a ratio of from about 4:1 to about 1:1 to sand. In yet a further embodiment, the fly ash is an additive in addition to a replacement of cement, or a replacement of cement and fine aggregate.

In specific embodiments, concrete of the invention comprises about 1 part by weight cementitious materials, about 1 to about 3 parts by weight fine aggregate, about 1 to about 5 parts by weight coarse aggregate, and about 0.35 to about 0.6 parts by weight water, such that the ratio of cementitious materials to water ranges from approximately 3:1 to 1.5:1; preferably, the ratio of cementitious materials to water is about 2:1. In a specific embodiment, the concrete comprises 1 part cementitious materials, 2 parts siliceous river sand or Ottawa sand, 3 parts ⅜" crushed basalt coarse aggregate, and 0.5 parts water.

The term "mortar" refers to a hardenable mixture comprising cementitious materials; a fine aggregate, such as sand; and water. Mortar of the invention further comprises fly ash having defined fineness. In a specific embodiment, the fly ash makes up from about 10% to about 50% of the cementitious materials. In a further aspect, the fly ash is used as fine aggregate in a ratio of from about 4:1 to about 1:1 to sand. In yet a further embodiment, the fly ash is an additive in addition to a replacement of cement, or a replacement of cement and fine aggregate.

In specific embodiments, mortar of the invention comprises about 1 part by weight cementitious materials, about 1 to about 3 parts by weight fine aggregate, and about 0.5 parts by weight water, such that the ratio of cementitious materials to water is approximately 2:1. In a specific embodiment, the mortar comprises 1 part cementitious materials, 2.75 parts Ottawa sand, and 0.5 parts water.

As noted above, fly ash can be used as a fine aggregate in concrete or mortar, in addition to having a role as a cementitious material. It has been found that substituting fly ash for a conventional fine aggregate, such as sand, provides the advantages of increased compressive strength of the concrete or mortar since the total amount of fly ash in the hardenable composition is the same, with a rapid rate of increase of compressive strength because the amount of cement in the cementitious materials is greater.

According to the present invention, the hardenable mixture can further comprise one or more of the following: kiln dust, e.g., the dust generated in the manufacture of cement; silica fume, which is a by-product from the silicon metal industry usually consisting of about 96%–98% reactive $SiO_2$, and which generally comes in very fine particle sizes of less than 1 micron; superplasticizer, such as Daracem-100

(W. R. Grace),an expensive but common additive for concrete used to decrease the water requirement for mixing the concrete; and a dispersing agent, such as sodium hexametaphosphate ($NaPO_3$). The use of a dispersing agent is particularly preferred when weathered fly ash is incorporated in the hardenable mixture.

Addition of silica fume can enhance the early rate of strength gain of a hardenable mixture, and therefore may be a desirable component of hardenable mixtures of the invention.

In a specific embodiment, a hardenable mixture of the invention may also contain glass fibers for reinforcement. The use of glass fibers in hardenable mixtures of the invention for reinforcement can be achieved because the fly ash, particularly finer fractions of fly ash, reacts more readily than glass fibers with reactive components of the cement, e.g., $Ca(OH)_2$, thus preventing long term reaction of the glass fibers with these reactive components, which would otherwise degrade the glass fibers. The most inert hardenable mixtures result are those that contain approximately equal amounts of fly ash, or fly ash and silica fume (as discussed below), and cement. The ability of fly ash to neutralize reactive agents in cement is discussed in greater detail in U.S. application Ser. No. 08/246,861, attorney docket No. 715-1-036, filed May 20, 1994, entitled "SULFATE AND ACID RESISTANT CONCRETE AND MORTAR" by the instant inventors.

In another specific embodiment, a hardenable mixture of the invention further comprises glass fibers, and silica fume. Silica fume reacts more readily with reactive components of cement than the glass fibers, and thus can provide early desirable protection of the glass fibers from degradation as well as early compressive strength gains. Subsequently, the fly ash will react with such reactive components, thus precluding early and late reactivity of glass fibers. As noted above, reaction of glass fibers with alkali and alkali earth compounds can lead to degradation of the glass fibers, and loss of tensile strength of the hardenable mixture.

Concrete beams of the invention with dimensions of 3"×6"×27" can be used to evaluate the bending strength of fly ash concrete, e.g., using simple beam with third-point loading. Preferably, such test procedures are in accordance with ASTM C 78 (1990, ASTM C 78–84, *Annual Book of ASTM Standards*, Vol 04.02).

The present invention will be better understood by reference to the following Examples, which are provided by way of exemplification and not by way of limitation.

EXAMPLES

Fly ashes used in this study were collected from a utility in the Northeastern section of the U.S. Fly ashes of different sources named DH, H, M, and P were used in this program. The last sample was obtained in both dry and weathered states as described earlier.

The standard ASTM 2"×2"×2" cube and 3"×6" cylinder specimens for studying the compressive strength of mortar and concrete, respectively, were used. The 3"×6"×27" beam specimens were selected for studying the bending or flexural strength of concrete. All tests were performed on a MTS closed-loop servo hydraulic testing machine.

Materials

Materials used in this study consisted of standard portland cement type I, Ottawa sand, siliceous sand (river sand), coarse aggregate, fly ash, kiln dust, silica fume, superplasticizer, dispersing agent, and water.

Two kinds of sand were used. Graded sand predominantly graded between the No. 300 (0.06 mm) sieve and the No. 100 (0.150 mm) sieve conforming to ASTM C-778 (1990, "Specification for Standard Sand," *Annual Book of ASTM Standards*, Vol. 04.08) was used as a standard sand. Another local siliceous sand (river sand) passing through sieve No. 4 (opening size 4.75 mm) was also used for casting mortar and concrete.

Crushed basalt coarse aggregate size of ⅜ was used for casting concrete.

Wet bottom boiler and dry bottom boiler fly ashes were selected for the study. These two type of fly ashes were further fractionated into different particle sizes for additional study.

Silica fume (produced in the manufacture of microelectronic chips) of very fine particle of size less than 1 micron and 96–98% reactive SiO2 was used in powder form. The addition of silica fume was intended to produce high strength concrete.

Superplasticizer (Daracem-100, W. R. Grace) was used according to standard procedures.

Sodium hexametaphosphate ($NaPO_3$) was normally used as a dispersing agent. The addition of dispersing agent in the fly ash concrete mix was to ensure the lumps of weathered fly ash were dispersed into fine particles and could as a result, be more reactive.

Tap water was used throughout.

The chemical composition of fly ashes and cement were determined by X-Ray Fluorescence (ASTM D-4326 1990, "Test Method for Major and Minor Elements in Coal and Coke Ash by X-Ray Fluorescence," *Annual Book of ASTM Standards*, Vol. 05.05).

Fly Ash Fineness

The fineness of fly ash was measured using two different standard methods; the Blaine air permeability and the fineness by the 45 microns (No. 325 sieve). Fineness was also determined as the fineness modulus, as described.

For the Blaine air permeability (Blaine fineness), the fineness was expressed in terms of the specific surface, expressed as total surface area in square centimeters per gram, or square meters per kilogram, of fly ash. The result obtained from the Blaine method was a measure of relative fineness rather than absolute fineness. The test procedure followed ASTM C 204 (1990, "Test Method for Fineness of Portland Cement," ASTM C 204-89, *Annual Book of ASTM Standards*, Vol. 04.01).

The fineness of fly ash retained on the sieve 45 microns (No. 325 sieve) was determined by the amount of fly ash retained when wet sieved on the No. 325 sieve in accordance with the ASTM C 430 (1990, "Test Method for Fineness of Hydraulic Cement by the 45-Micron (No. 325) Sieve," ASTM C 430-89, *Annual Book of ASTM Standards*, Vol. 04.01) test method for hydraulic cement.

Fineness modulus was determined by the summation of the percentage of fly ash that retained on the following sieve sizes: 0, 1, 1.5, 2, 3, 5, 10, 20, 45, 75, 150, and 300 microns.

The setting time of concrete or mortar mixtures was determined by Vicat needle and Gillmore needle tests. The test methods followed ASTM C-191 (1990, "Test Method for Setting Time of Hydraulic Cement by Vicat Needle," ASTM C 191-82, *Annual Book of ASTM Standards*, Vol. 04.01) for the Vicar test and ASTM C 266 (1990, "Test Method for Setting of Hydraulic Cement Paste by Gillmore Needles," ASTM C 266-89, *Annual Book of ASTM Standards*, Vol. 04.01) for the Gillmore test.

Fly Ash Mortar

DH, H, dry, and weathered fly ashes were mixed with cement and Ottawa sand. The replacement of a portion of portland cement by fly ash varied as 0%, 15%, 25% and 35% by weight of cementitious (cement+fly ash) materials. The specimens were mixed and cast in accordance with ASTM C 109 (1990, "Test Method for Compressive Strength of Hydraulic Cement Mortars . . . ," ASTM C 109-88, *Annual Book of ASTM Standards*, Vol. 04.01). All specimens were cured in saturated lime water and tested at the age of 1, 3, 7, 14, 28, 56, and 90 days.

Fly Ash as a Replacement

Fly ashes were used as replacement of cement. By keeping the water, river sand, and cementitious (cement+fly ash) materials as constants, cement was replaced by fly ash. The replacement of fly ash was varied from 15% to 50% by weight of cementitious materials. All the specimens were cured in saturated lime water until the time of testing. This was to ensure that moisture and lime are available to provide any potential reaction which may occur. The compressive strengths of 2"×2"×2" cube mortars were tested at 1, 3, 7, 14, 28, 56, 90 and 180 days.

Fly Ash as an Additive

Fly ashes were used as an additive in mortar. In some instances, 10% of sand was replaced by fly ash. By keeping the cement, river sand, and water as constants, fly ash was added directly in the mix. The addition of fly ash was varied from 15% to 50% by weight of cement. All the specimens were cured in saturated lime water and tested for their compressive strengths at 1, 3, 7, 14, 28, 56, 90 and 180 days.

Fractionated Fly Ash Concrete and Mortar

Dry and wet bottom boiler fly ashes were separated into different particle sizes by using the Micro-Sizer Air Classifying System. The fly ash was fractionated into six particle size distributions. The fractionated fly ashes and the original feed fly ashes were used to replace 15%, 25% 35% and 50% of cement by weight of cementitious materials. The compressive strengths of fractionated fly ash concrete were tested from 1 day to 180 days. The effect of particle size from 0–5, 0–10, 0–15, 0–20, 0–30, 0–44 microns, and the original feed fly ashes, were investigated and compared with the control concrete. The 3"×6" cylinder was used to determine the compressive strength of fractionated fly ash concrete. The standard size of 2"×2"×2" cube was used to determine the compressive strength of fractionated fly ash mortars. The mix proportion of fractionated fly ash mortar is shown in Table 1.

TABLE 1

Mix Proportion of Fractionated Fly Ash Mortar

| Ingredients | Fractionated Fly Ash (Dry and Wet Bottom Boiler) By Weight | | | |
|---|---|---|---|---|
| | 0 | 15% | 25% | 50% |
| Cement | 1.00 | 0.85 | 0.75 | 0.50 |
| Fly Ash | — | 0.15 | 0.25 | 0.50 |
| Sand | 2.75 | 2.75 | 2.75 | 2.75 |
| Water | 0.50 | 0.50 | 0.50 | 0.50 |
| Water/(Cem + FA) | 0.50 | 0.50 | 0.50 | 0.50 |

High Strength Fly Ash and Silica Fume Concrete

The very fine particle sizes of fly ashes, i.e., the particles smaller than 5 microns, were employed to produce higher strength fly ash concrete. Fifteen and twenty five percent of fly ash by weight of cementitious materials were used in the concrete as a replacement for cement. Silica fume in the powder form was also used in the same proportion as the fly ash. The compressive strength of the high strength fly ash concrete and silica fume concrete were determined and compared. The mix proportion of high strength fly ash and silica fume concrete is shown in Table 2.

TABLE 2

Mix Proportion of High Strength Fly Ash and Silica Fume Concrete

| Ingredient | CSF, Control (lb) | 15% Repl. (lb) | 25% Repl. (lb) |
|---|---|---|---|
| Cement | 10 | 8.5 | 7.5 |
| Fly Ash or Silica Fume | — | 1.5 | 2.5 |
| River Sand | 20 | 20 | 20 |
| Aggregate, Basalt ⅜" | 30 | 30 | 30 |
| Super P. | 100 ml | 100 ml | 100 ml |
| Water | 4.17 | 4.17 | 4.17 |
| Water/(Cementitious) | 0.417 | 0.417 | 0.417 |

Chemical Composition of Fractionated Fly Ashes

The chemical composition of fractionated fly ashes are shown in Table 3. Sample CEM is the cement sample used in this study. Samples DRY and WET are the fly ashes from the original feed of dry and wet bottom boiler ashes, respectively. 3F is the finest fly ash sample of the dry bottom boiler ash and 13F is the finest sample of the wet bottom boiler ash. The coarsest fly ashes samples of dry and wet bottom boiler ash are 1C and 18C, respectively.

Both wet and dry bottom boiler fly ashes used herein were classified as Class F fly ash according to ASTM C-618 (1990, supra). Most of the fractionated fly ashes varied slightly in the oxide composition with changes in particle size. It has been reported that separation of Class F (high calcium) fly ash into size fractions does not result in significant chemical, morphological or mineralogical specification between particles (Hemming and Berry, 1986, Symposium Proceedings, Fly Ash and Coal Conversion By-Products: Characterization, Utilization and Disposal II, Material Research Society 65:91–130). The $SiO_2$ content tends to be lower when the particle size is larger. Differences in chemical compositions of the two fly ashes were observed in the $SiO_2$, $Fe_2O_3$, and $CaO$ contents. Samples of the dry bottom boiler fly ash were about 10% richer in $SiO_2$ than the wet bottom boiler fly ash. The CaO content of the dry bottom boiler fly ash varied from 1.90% to 2.99%, while for wet bottom boiler fly ash, the CaO varied from 6.55% to 7.38%. $Fe_2O_3$ content of wet bottom boiler fly ash was about twice as high in wet bottom boiler than dry bottom boiler fly ash. The highest concentration of $Fe_2O_3$ of each type of fly ashes was observed in the coarsest particle sizes, i.e., 1C and 18C. Chemical composition of the fly ashes is shown in Table 3.

TABLE 3

Chemical Composition of Fractionated Fly Ashes and Cement

| Sam | LOI | $SO_3$ | $SiO_2$ | $Al_2O_3$ | $Fe_2O_3$ | CaO | $K_2O$ | MgO | $Na_2O$ |
|---|---|---|---|---|---|---|---|---|---|
| CEM | 0.73 | 2.53 | 20.07 | 8.84 | 1.41 | 60.14 | 0.86 | 2.49 | 0.28 |
| 3F0 | 4.97 | 1.69 | 49.89 | 26.94 | 5.43 | 2.99 | 1.76 | 0.99 | 0.33 |
| 5F | 4.10 | 1.53 | 50.27 | 26.74 | 5.30 | 2.95 | 1.74 | 0.93 | 0.33 |
| 6F | 3.12 | 1.09 | 51.40 | 26.54 | 4.91 | 2.72 | 1.71 | 0.74 | 0.31 |
| 10F | 2.52 | 0.72 | 51.98 | 26.23 | 4.44 | 2.28 | 1.60 | 0.54 | 0.29 |
| 11F | 2.04 | 0.53 | 51.27 | 26.28 | 4.42 | 2.02 | 1.55 | 0.49 | 0.26 |
| 1C | 1.46 | 0.39 | 53.01 | 26.50 | 5.66 | 1.90 | 1.61 | 0.56 | 0.24 |
| DRY | 2.75 | 0.98 | 52.25 | 26.72 | 5.43 | 2.41 | 1.67 | 0.69 | 0.28 |
| 13F | 2.67 | 3.81 | 38.93 | 24.91 | 12.89 | 6.85 | 2.10 | 1.55 | 1.31 |
| 14F | 1.94 | 3.47 | 39.72 | 25.08 | 13.02 | 6.71 | 2.11 | 1.50 | 1.31 |
| 15F | 1.88 | 3.33 | 40.25 | 25.02 | 13.12 | 6.60 | 2.11 | 1.47 | 1.30 |
| 16F | 2.06 | 3.05 | 40.65 | 24.92 | 13.26 | 6.55 | 2.09 | 1.41 | 1.26 |
| 18F | 1.94 | 2.94 | 41.56 | 24.47 | 14.21 | 6.58 | 2.01 | 1.40 | 1.17 |
| 18C | 2.55 | 2.40 | 43.25 | 23.31 | 17.19 | 7.38 | 2.00 | 1.30 | 0.88 |
| WET | 2.05 | 3.13 | 41.54 | 24.74 | 14.83 | 6.89 | 2.07 | 1.43 | 1.17 |

It is interesting to note that after fly ash was fractionated into different sizes, loss of ignition (LOI) of the finest particle was higher than for larger particles. In other words, the LOI content gradually decreased as the particle size increased. Ravina (1980, Cement and Concrete Research 10:573–80) also reported that the finest particle of fly ashes has the highest LOI values. Ukita et al. (1989, Fly Ash, Silica Fume, Slag, and Natural Pozzolans In Concrete, SP-114, American Concrete Institute, Detroit, pp. 219–40) also showed that although chemical composition did not change when the median diameter of fly ash decreased from 17.6 microns to 3.3 microns, LOI increased from 2.78 to 4.37.

Our observations and these prior reports conflict with the report of ACI Committee 226 (1987, "Use of Fly Ash In Concrete," ACI 226.3R-87, ACI J. Proceedings 84:381–409) and of Sheu et al. (1990, Symposium Proceedings, Fly Ash and Coal Conversion By-Products: Characterization, Utilization and Disposal VI, Materials Research Society 178:159–166), which state that the coarse fraction of fly ash usually has a higher LOI than the fine fraction.

Particle Size Analysis of Fractionated Fly Ashes

The particle size distributions of Fractionated fly ashes from the dry and wet bottom boilers are shown in FIGS. 1A and 1B, respectively. The curves for the original feed fly ashes are not as steep as others since the non-fractionated original feed ash includes the entire range of sizes, and thus a wider range of size distributions than fractionated samples.

The percentage of fly ash in each fraction having a size less than a particular size is indicated in parentheses in each curve. For example, in case of the 3F fly ash, the finest of dry bottom boiler fly ash, 3F (90%-5 µm) means that 90% of the fly ash particles are smaller than 5 microns.

From the original feed, each type of fly ash was fractionated into six ranges. As shown in FIGS. 1A and 1B, the particle size of fly ash varied from 0–5.5 micron to 0–600 microns. The median diameter of the particles in each fraction was determined from the curves in FIGS. 1A and 1B by extrapolating from the 50% percent finer value. The median diameters of 3F and 13F were 2.11 and 1.84 microns, respectively, while the median diameters of the coarsest particle size, 1C and 18C, were 39.45 and 29.23 microns, respectively. For wet bottom boiler fly ash, 13F was the finest fraction and 18C was the coarsest.

The original feed of wet bottom boiler fly ash was found to be finer than the original feed of dry bottom boiler fly ash. The particle sizes of original feed of dry bottom boiler fly ash varied from about 1 micron to 600 microns, with a median particle size of 13.73 microns. The original feed of wet bottom boiler fly ash included particles up to 300 microns with a median diameter of 6.41 microns. Particles from the smaller size fractions tend to have a more spherical shapes (Hemming and Berry, 1986, supra).

Fineness of Fractionated Fly Ash

Traditional values of fineness of fly ashes were determined both by wet sieve analysis and by the Blaine fineness together with the specific gravity of fly ashes, which are shown in Table 4. Median diameter, the diameter of which 50 percent of particles are larger than this size, is also presented in this table. According to ASTM C-618 (1990, supra), specifications, fractionated 1C fly ash is unacceptable for use in concrete since the percentage of the fly ash retained on sieve No. 325 is higher than 34%.

TABLE 4

Fineness of Cement and Fractionated Fly Ashes

| Sample No. | Specific Gravity (g/cm³) | Fineness: Retained 45 µm (%) | Fineness: Blaine (cm²/g) | Median Diameter (µm) |
|---|---|---|---|---|
| CEM | 3.12 | — | 3815 | — |
| 3F | 2.54 | 0 | 7844 | 2.11 |
| 5F | 2.53 | 0 | 6919 | 2.66 |
| 6F | 2.49 | 0 | 4478 | 5.66 |
| 10F | 2.42 | 0 | 2028 | 12.12 |
| 11F | 2.40 | 1.0 | 1744 | 15.69 |
| 1C | 2.28 | 42.0 | 1079 | 39.45 |
| DRY | 2.34 | 20.0 | 3235 | 13.73 |
| 13F | 2.75 | 0 | 11241 | 1.84 |
| 14F | 2.73 | 0 | 9106 | 2.50 |
| 15F | 2.64 | 0 | 7471 | 3.09 |
| 16F | 2.61 | 0 | 5171 | 5.54 |
| 18F | 2.51 | 0 | 3216 | 9.84 |
| 18C | 2.42 | 29.0 | 1760 | 29.25 |
| WET | 2.50 | 10.0 | 5017 | 6.41 |
| DRY FA | 2.25 | 22.0 | 3380 | 11.51 |
| WEATHERED | 2.20 | 18.0 | 2252 | 13.22 |
| H | 2.30 | 15.0 | 2748 | 13.15 |
| DH | 2.24 | 26.0 | 2555 | 18.30 |

Two methods were used to measure the fineness of fractionated fly ashes. The first method involved determining the residue on a 45 micron (No. 325) sieve. Using the sieve No. 325 method, the fractionated fly ash samples 3F, 5F, 6F, 10F, 13F, 14F, 15F, 16F and 18F had the same fineness; all of them have zero retention.

The second method was the surface area measurement by air permeability test.

Opinions differ as to whether sieve residue or surface area are better indicator of fly ash fineness (Cabrera, et al., 1986, Fly Ash, Silica Fume, Slag and Natural Pozzolans in Concrete, SP-91, American Concrete Institute, Detroit, pp. 115–144). In the United States, the fineness of fly ash is specified by the residue on the 45 micron sieve only. Ravina (1980, Cement and Concrete Research 10:573–580) found that pozzolanic activity correlates more closely with specific surface area measurements. In contrast, Lane and Best (1982, Concrete Int'l: Design & Construction 4:81–92) urges that the residue on a 45 micron sieve is a more consistent indicator of pozzolanic activity. White and Roy (1986, Symposium Proceedings, Fly Ash and Coal Conversion By-Products: Characterization, Utilization and Disposal II, Material Research Society 65:243–253) also concluded that the fineness parameter given in the Blaine fineness is not as important as the fly ash size fraction less than 45 microns.

The results of the present work rebut the conclusions advanced in the White and Roy article, especially in the case of fractionated fly ashes, since the results disclosed herein demonstrate that the preferred active particle size of fly ash is significantly smaller than 45 microns.

It can be noted from Table 5 that the finer the particle size of fractionated fly ashes was, the higher the specific gravity and the Blaine fineness. In general, fly ash of greater fineness had greater specific gravity, in agreement with previous investigation (Hansson, 1989, Symposium Proceedings, Fly Ash and Coal Conversion By-Products: Characterization, Utilization and Disposal V, Material Research Society 136:175–183).

Density of fly ash from different electric generating plants varies from 1.97 to 2.89 g/cm$^3$ but normally ranges between about 2.2 to 2.7 g/cm$^3$ (Lane and Best, 1982, supra). Work done by McLaren and Digiolin (1990, Coal Combustion and By-Product Utilization Seminar, Pittsburgh, p. 15) reported that Class F fly ash had a mean specific gravity value of 2.40.

The specific gravity of fractionated fly ashes varies from 2.28 for the coarsest fly ash to 2.54 for the finest fly ash for dry bottom boiler fly ash, and from 2.22 for the coarsest to 2.75 for the finest wet bottom boiler fly ash.

The differences in density between dry bottom boiler and wet bottom boiler fly ashes suggest that the very fine particles of wet bottom boiler fly ash are thick-walled, void free, or composed of more dense glasses and crystalline components than dry bottom boiler fly ash (Hemming and Berry, 1986, Symposium Proceedings, Fly Ash and Coal Conversion By-Products: Characterization, Utilization and Disposal II, Material Research Society 65:91–103).

The Examples presented herein disclose results of incorporation of fly ash of defined particle size distributions in concrete and mortar. The fractionated fly ashes each have a smaller size range than the original feed fly ash, that is, fly ash as received from a storage silo. Due to its narrower range of particle size distribution of fractionated fly ash compared to the wider range of particle size distributions of the original ash, each fractionated fly ash has a more defined pozzolanic activity than the original feed fly ash.

In the Examples, Sample CCCC is generally the control sample, i.e., sample without any fly ash. CDRY and CWET are the samples for concrete mixed with the original feed of dry and wet bottom boiler fly ashes, respectively. The fractionated fly ashes used in the sample are designated by the number(s) followed by the character. The last two digits indicate the proportion by weight of fly ash as cementitious materials in the mix. For example, sample "3FC15" means that the concrete sample consists of 3F fly ash present at 15% by weight of cementitious materials. Similarly, sample "3FC25" stands for the concrete sample using 25% of 3F fly ash by weight of cementitious materials.

Example 1

Effect of Fractionated Dry Bottom Boiler Fly Ash on the Strength of Concrete

The relationship between compressive strength of the fractionated dry bottom boiler fly ash concrete and its corresponding age is shown in FIG. 2A, 2B, 2C, and 2D.

The compressive strength of the fractionated dry bottom boiler fly ash concrete, in which fly ash replaces 15% of cement, relative to control (shown as a percentage) is summarized in Table 5 and FIG. 2A.

TABLE 5

Percentage Compressive Strength of the Fractionated of Dry Bottom boiler Fly Ash Concrete Over Time (15% Replacement)

| Sample No. | Percentage Compressive Strength of Control | | | | | | |
|---|---|---|---|---|---|---|---|
| | 1-d | 7-d | 14-d | 28-d | 56-d | 90-d | 180-d |
| CCCC* | 2157 | 6237 | 7141 | 8157 | 8707 | 9195 | 10161 |
| 3FC15 | 79.8 | 95.3 | 100.7 | 102.0 | 104.8 | 107.5 | 109.2 |
| 6FC15 | 79.6 | 92.1 | 96.4 | 97.4 | 102.8 | 103.1 | 104.4 |
| 10FC15 | 77.6 | 90.9 | 90.7 | 92.4 | 96.6 | 98.0 | 101.8 |
| 11FC15 | 77.3 | 89.0 | 90.0 | 90.1 | 93.5 | 94.9 | 96.9 |
| 1CC15 | 74.1 | 86.8 | 89.8 | 85.5 | 90.6 | 89.8 | 91.2 |
| CDRY15 | 75.2 | 88.6 | 90.7 | 91.2 | 95.3 | 97.3 | 99.2 |

*Values for control are the actual compressive strength in psi. These are the 100% values at each time point.

The strength of fractionated fly ash concrete was always lower than the control mix at day 1. Replacement of a portion of cement with Class F fly ash generally produces lower strength because fly ash acts as a relatively inert component during the early period of hydration (Carette and Malhortra, 1983, Fly Ash, Silica Fume, Slag, and Other Mineral By-Products in Concrete, SP-79, American Concrete Institute, Detroit, pp. 765–784). This result has also been reported by Plowman (1984, Proceedings, 2nd Int'l Conference on Ash Technology and Marketing, London, pp. 437–443) and Langley et al. (1989, ACI J. Proceedings 86:507–514).

With 15% replacement of cement by fractionated fly ashes, the compressive strength at 1 day was reduced about 20% to 25% compared to the control (sample CCCC). Variation of the strength correlates with the different particle sizes of fly ash. The finer particle fly ash mediates a better packing effect than the coarser one, so the rate of strength gain is greater.

After 14 days of curing, 3FC15 concrete (15% replacement of 3F fly ash) had a compressive strength essentially equal to the control. This means that the pozzolanic activity 10FC15 and CDRY15 (15% replacement of the original feed of dry bottom boiler fly ash) achieved the same strength as the control.

With the coarsest particle size of fly ash in concrete, 1CC15, the compressive strength varied from 1598 psi at 1 day to 9269 psi at 180 days, or from 74.1% to 91.2% relative to the control concrete. The compressive strength of sample 3FC15 varies from 1721 psi at 1 day to 11100 psi at 180 days, or from 79.8% to 109.2% compared with the control strength. Since all the chemical composition of these fractionated fly ashes are almost the same, the particle size of fly ash is the major factor affecting the compressive strength of fly ash concrete.

Figure 2B:
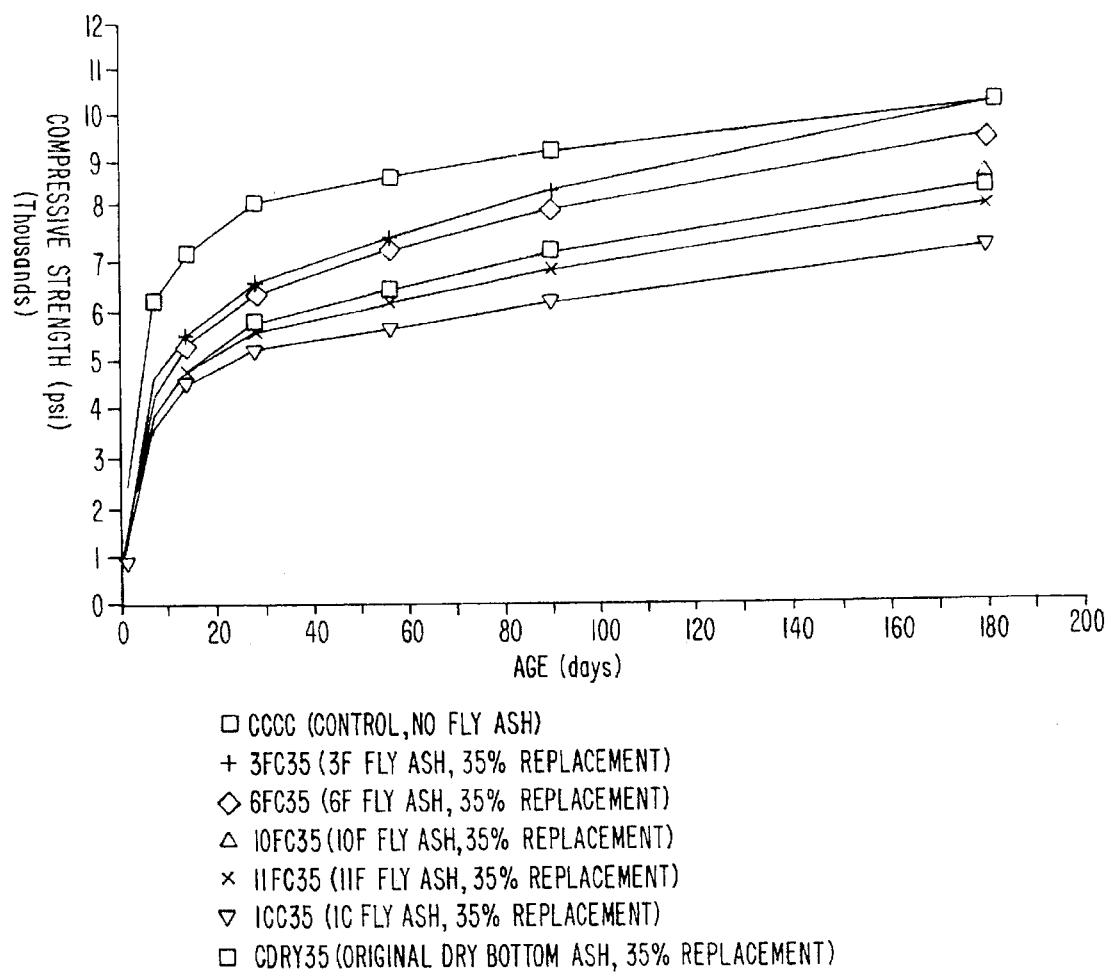

The results of compressive strength gain of concrete in which 25% of cement in cementitious materials is replaced with fractionated dry bottom boiler fly ash is shown in Table 6 and FIG. 2B.

TABLE 6

Percentage Compressive Strength of the Fractionated of Dry Bottom boiler Fly Ash Concrete Over Time (25% Replacement)

| Sample No. | Percentage Compressive Strength (%) | | | | | | |
|---|---|---|---|---|---|---|---|
| | 1-d | 7-d | 14-d | 28-d | 56-d | 90-d | 180-d |
| CCCC | 2157 | 6237 | 7141 | 8157 | 8707 | 9195 | 10161 |
| 3FC25 | 70.0 | 84.7 | 90.9 | 94.2 | 98.4 | 103.3 | 105.6 |
| 6FC25 | 68.8 | 77.2 | 81.8 | 86.5 | 93.3 | 95.5 | 98.2 |
| 10FC25 | 67.1 | 75.9 | 78.7 | 82.0 | 88.7 | 91.0 | 91.7 |
| 11FC25 | 64.4 | 74.3 | 77.9 | 80.7 | 84.9 | 88.2 | 89.6 |
| 1CC25 | 63.5 | 72.8 | 75.6 | 78.0 | 80.4 | 81.8 | 82.2 |
| CDRY25 | 64.4 | 73.6 | 76.9 | 80.9 | 84.9 | 87.5 | 89.3 |

*Values for control are actual compressive strength in psi, which constitute 100% at each time point.

of the finest particle size fly ash produced greater strength than that achieved by the hydration of cement alone. This increased rate of strength gain result continued, resulting in larger differences between the 3FC15 fly ash concrete and the control concrete with time.

With time, larger size fractions also achieved strengths comparable to or greater than control. For example, sample 6FC15 gained the same strength as the control before the age of 56 days. After about 180 days of curing, the samples When 25% of cement is replaced with the fractionated dry bottom boiler fly ash, early strengths of the concrete are lower than with a 15% replacement with the same fly ash fraction. The results indicate that the finer fly ash particles yield greater strength gains than the coarser particles.

The results of compressive strength gain of concrete in which 35% of cement in cementitious materials is replaced with fractionated dry bottom boiler fly ash is shown in Table 7 and FIG. 2C.

TABLE 7

Percentage Compressive Strength of the Fractionated of Dry Bottom Boiler Fly Ash Concrete Over Time (35% Replacement)

| Sample No. | Percentage Compressive Strength (%) | | | | | | |
|---|---|---|---|---|---|---|---|
| | 1-d | 7-d | 14-d | 28-d | 56-d | 90-d | 180-d |
| CCCC* | 2157 | 6237 | 7141 | 8157 | 8707 | 9195 | 10161 |
| 3FC35 | 52.7 | 73.8 | 77.5 | 80.9 | 85.9 | 91.4 | 99.2 |
| 6FC35 | 45.8 | 67.7 | 74.6 | 78.2 | 83.2 | 87.0 | 93.0 |
| 10FC35 | 41.2 | 62.7 | 67.7 | 70.7 | 74.3 | 77.6 | 82.7 |
| 11FC35 | 40.9 | 59.9 | 66.8 | 68.8 | 71.4 | 74.6 | 79.0 |
| 1CC35 | 39.9 | 57.2 | 63.0 | 64.2 | 65.4 | 67.4 | 71.3 |

TABLE 7-continued

Percentage Compressive Strength of the
Fractionated of Dry Bottom Boiler Fly Ash Concrete Over Time
(35% Replacement)

| Sample No. | Percentage Compressive Strength (%) | | | | | | |
|---|---|---|---|---|---|---|---|
| | 1-d | 7-d | 14-d | 28-d | 56-d | 90-d | 180-d |
| CDRY35 | 42.0 | 62.4 | 65.8 | 71.1 | 74.0 | 78.2 | 82.6 |

*Values for control are actual compressive strength in psi, which constitute 100% at each time point.

With the replacement of fly ash up to 35% by weight of cementitious materials, the compressive strength for fractionated fly ash concrete at 1 day varied from 39.9% to 52.7% of the control strength, depending on the fineness of the fly ash. In general, the compressive strength of the finer particle mixes was higher than that for the coarser ones.

After 180 days of curing, the compressive strength of fly ash concrete made with 35% original feed of dry bottom boiler fly ash was 8389 psi, or 82.6% of the control concrete. With the finest particle size of fly ash, 3F, it took about 180 days for the fly ash concrete to have the same strength as the control. The compressive strength of 3FC35 varies from 1136 psi at 1 day to 10080 psi at 180 days. That is an increase of about 8.8 times from 1 day to 180 days. The strength of the coarsest sample, 1C35, at 180 days is only 71.3% of the control strength.

FIG. 2C is a graph showing the relationship of compressive strength to age of concrete samples in which 35% of cementitious materials are fractionated or non-fractionated fly ash, as well as control (no fly ash). A number of points are made by this graph. The first is that initial rate of strength gain depends critically on the particle size range of the fly ash. After this period, which ranges up to about 14 to about 28 days, the slopes of compressive strength over time (rate of strength gain) become parallel, i.e., independent of particle size. At these points, rate of strength gain appears to be a diffusion-controlled pozzolanic effect. Nevertheless, in order to achieve acceptable compressive strength at early time points, which is important in building construction, clearly small particle fly ash fractions are preferable.

With 50% fly ash of the cementitious materials, all strengths of fractionated fly ash concrete are lower than the control strength (FIG. 2D). The compressive strength at 1 day varies from 407 psi to 567 psi (from the coarse to the fine particle size of fly ash) or 18.9% to 26.3% of the control strength. This strength is much lower than the control strength which is 2157 psi. Of note even with the 50% replacement sample, the compressive strength of fly ash concrete gradually increases with time due to the pozzolanic activity of fly ash. The strength of 3FC50 varies from 567 psi at 1 day to 8639 psi at 180 days, or 26.3% to 85.0% relative to the control.

Also, after 28 days the slope of compressive strength over time of 3FC50 concrete is higher than the slope of the control. This means that after 28 days the pozzolanic activity of the fly ash contributes more strength than the strength produced by the hydration of cement.

Example 2

Compressive Strength of Fractionated Wet Bottom Boiler Fly Ash Concrete

The relationship between compressive strength of the fractionated wet bottom boiler fly ash concrete and its corresponding age is shown in FIG. 3A, 3B, 3C and 3D.

The compressive strength of the original feed of wet bottom boiler fly ash was higher than that from the dry bottom boiler fly ash at the same age and for the same mix proportions. This was probably due to the finer particle size of the wet bottom boiler fly ash.

With 15% replacement of cement by fly ash (FIG. 3A), all the early strengths of fractionated fly ash concrete were lower than the control. At 14 days, the compressive strength of 13FC15 was a little higher than the control strength. After 56 days, sample 15FC15 gave the same strength as the control concrete. Samples 16FC15 and 18FC15 achieved the same strength as the control concrete after 90 days. After 180 days, all of the fractionated fly ash concretes had higher strength than the control concrete except sample 18CC15, which had 95.3% of the control strength.

Sample 18CC15 was made up with 18CC ash, which has the residue retained on sieve No. 325 (45 microns) of 29%. This value is lower than the limit set by ASTM C 618 (1990, supra) of 34%. The 29% retention value indicates that the active particle size of fly ash in the 18CC fraction is smaller than the 45 micron of sieve opening.

It took 180 days for the original feed of wet bottom boiler fly ash concrete to gain strength of the same order as the control concrete. These data are summarized in Table 8.

TABLE 8

Percentage Compressive Strength of the
Fractionated Dry Bottom Boiler Fly Ash Concrete Over Time
(15% Replacement)

| Sample No. | Percentage Compressive Strength (%) | | | | | | |
|---|---|---|---|---|---|---|---|
| | 1-d | 7-d | 14-d | 28-d | 56-d | 90-d | 180-d |
| CCCC | 2157 | 6237 | 7141 | 8157 | 8707 | 9195 | 10161 |
| 13FC15 | 92.6 | 96.4 | 101.1 | 102.1 | 106.0 | 107.3 | 110.2 |
| 15FC15 | 91.7 | 94.7 | 97.2 | 97.1 | 101.1 | 102.6 | 106.4 |
| 16FC15 | 88.0 | 92.0 | 93.0 | 93.8 | 98.9 | 101.4 | 105.5 |

TABLE 8-continued

Percentage Compressive Strength of the
Fractionated Dry Bottom Boiler Fly Ash Concrete Over Time
(15% Replacement)

| Sample | Percentage Compressive Strength (%) | | | | | | |
|---|---|---|---|---|---|---|---|
| No. | 1-d | 7-d | 14-d | 28-d | 56-d | 90-d | 180-d |
| 18FC15 | 85.7 | 92.0 | 92.1 | 92.0 | 94.2 | 99.3 | 103.4 |
| 18CC15 | 84.4 | 87.6 | 88.0 | 88.6 | 89.9 | 91.2 | 95.3 |
| CWET15 | 85.5 | 87.7 | 88.9 | 90.0 | 93.1 | 96.7 | 100.0 |

Figure 3B:
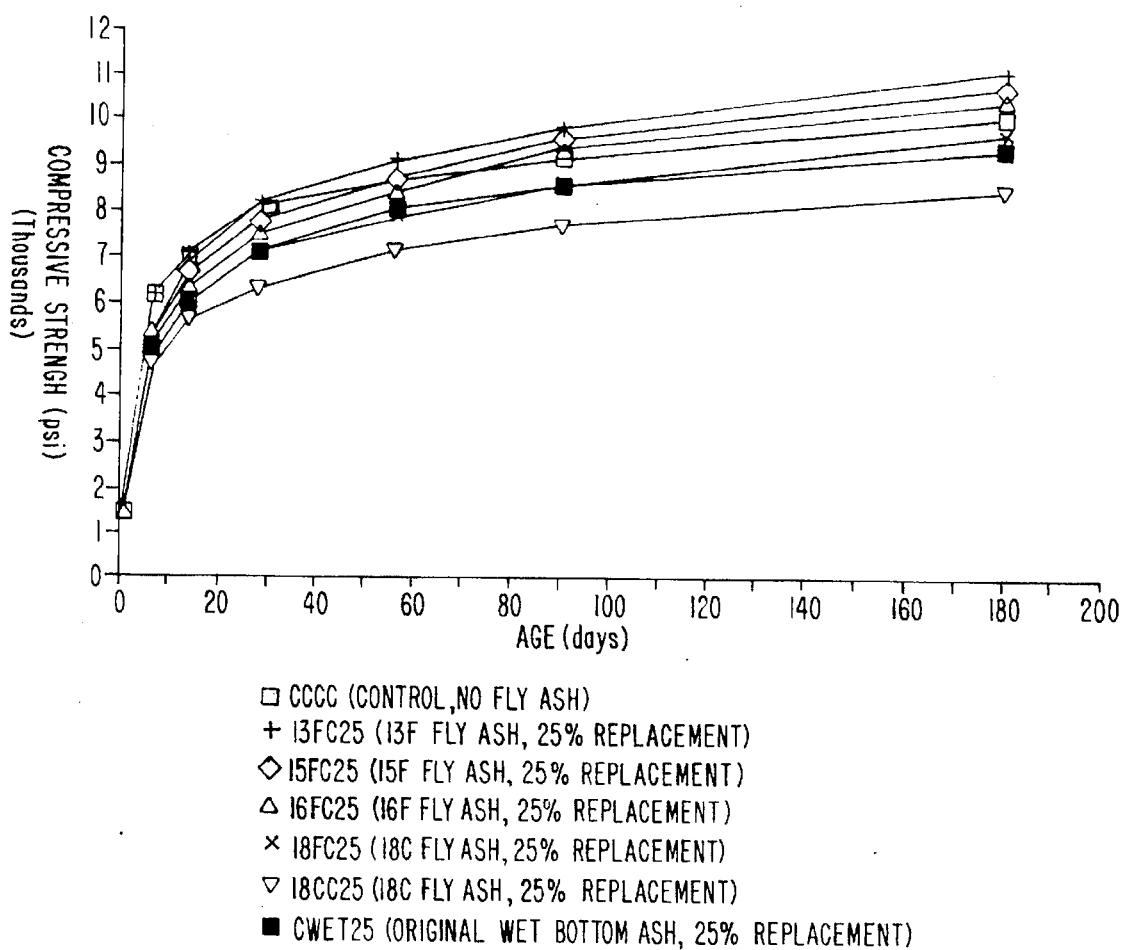
FIG. 3 presents graphs showing the compressive strength of concrete with age. The concrete contains wet bottom boiler fly ash or fractionated wet bottom boiler fly ash as a replacement for 15% (A), 25% (B), 35% (C), and 50% (D) of cement in the concrete. The fractionated fly ashes are as described in FIG. 1 and the Examples: CCCC (open squares, control containing no fly ash); 13FCxx (plus signs, 13F fly ash fraction, xx stands for the percentage of fly ash used to replace cement); 15FCxx (open diamonds, 15F fly ash fraction); 16FCxx (open triangles, 16F fly ash fraction); 18FCxx (X, 18F fly ash fraction); 18CCxx (inverted open triangle, 18C fly ash fraction); and CWETxx (open square [uniformly of lower compressive strength at each time point than the control sample], original wet bottom boiler fly ash feed).

The results with 25% replacement were close to those observed with 15% replacement with the fractionated wet bottom boiler fly ash concrete, except that the compressive strengths were uniformly lower (FIG. 3B). Early strengths of fractionated fly ash concrete were lower than control concrete up to 14 days. At 28 days and longer, sample 13FC25 demonstrated higher strength than control strength. At 180 days, the compressive strength of 13FC25 was 11162 psi, or 109.9% of the control value. Sample 15FC25 reached the same strength as the control concrete before 56 days. Before 90 days of curing, sample 16FC25 also achieved the same strength as the control. The strength of concrete using the coarsest particle, 18CC25, was only 84.4% of the control concrete at 180 days. These results which are summarized in Table 9, again show that the strength of fractionated fly ash concrete depends on the particle size and their distribution within the fractionated fly ash. Fly ash fractions containing smaller size particles demonstrated higher rates of compressive strength gain.

Figure 3C:
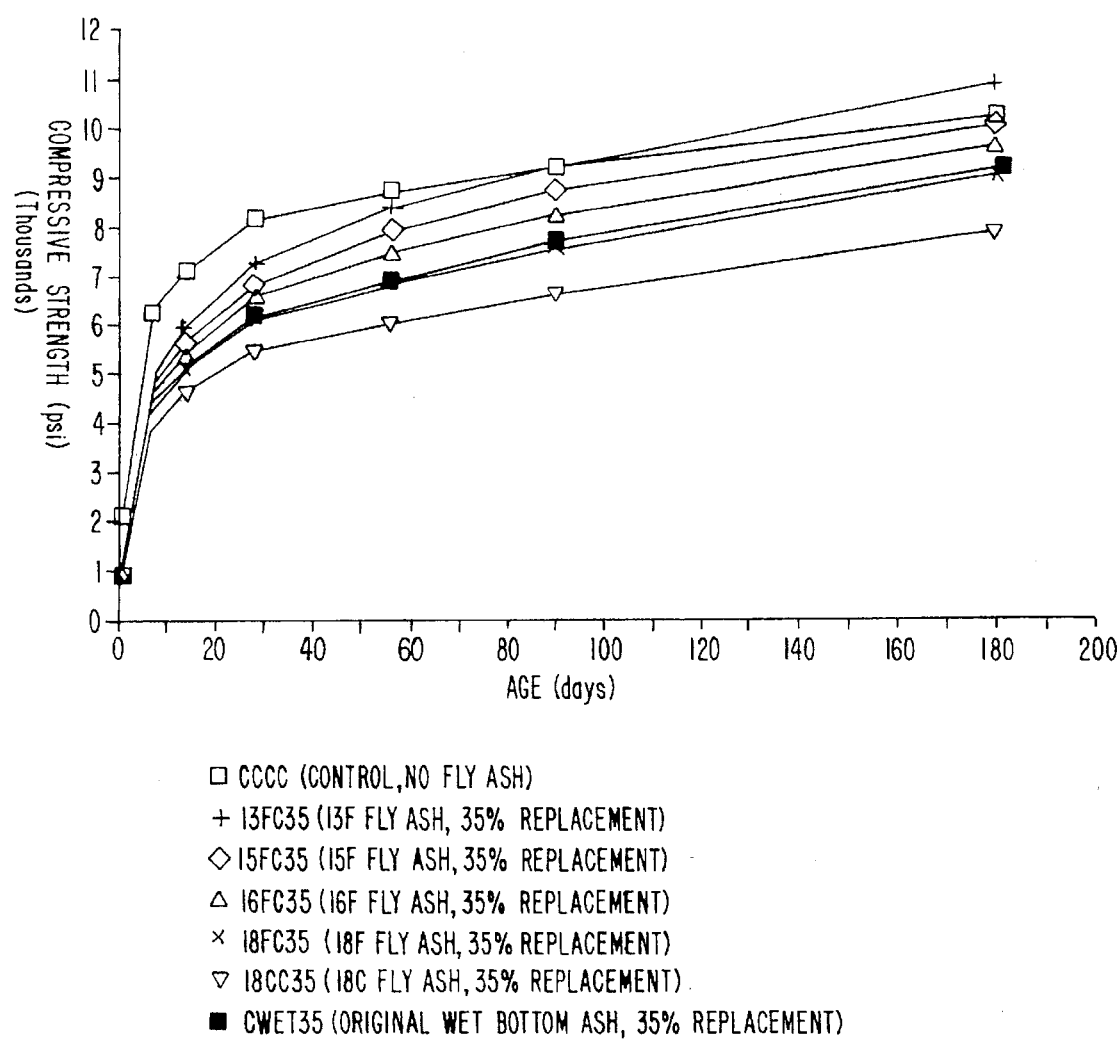
Figure 3D:
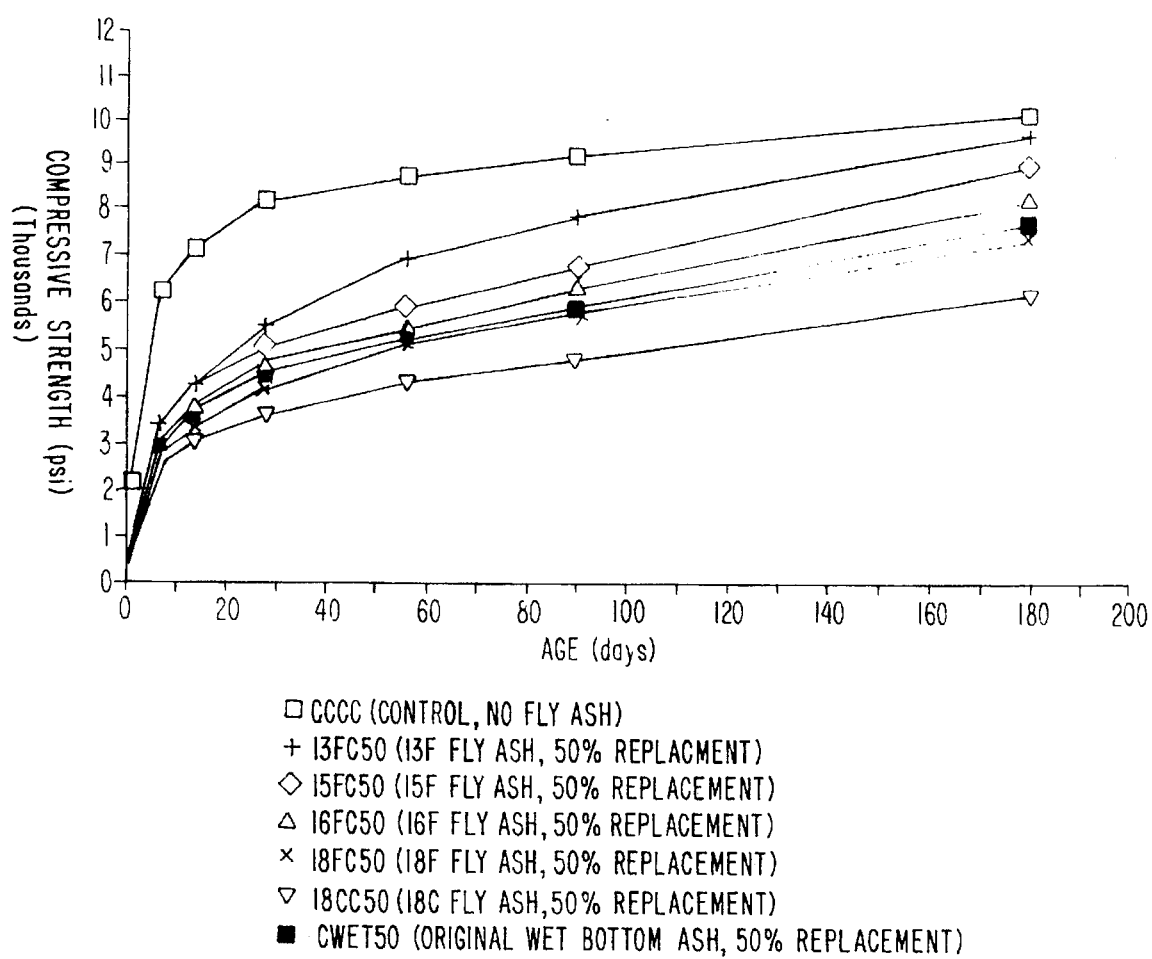

Replacement of 50% of cement with wet bottom boiler fly ash yielded concrete of much lower compressive strength (FIG. 3D). The replacement of cement with fly ash to 50% by weight of cementitious materials gave very low strength at 1 day. The compressive strength at 1 day varied from 484 psi to 733 psi, or from 22.4% to 34.0% of the control strength. After 180 days of curing, all of the fractionated fly ash concrete samples were of lower compressive strength than the control.

Although the amount cement in each fly ash concrete was only half of the control sample, some of fly ash concretes still gave a reasonable strength result. Sample 13FC50 has compressive strength of 9672 psi, or 95.2% of the control, at 180 days. The strengths of samples 15FC50 and 16FC50 were 88.2% and 80.8% of the control concrete, respectively.

Example 3

Workability of Fractionated Fly Ash Concrete

Slump test results were obtained for fractionated fly ash concrete. The slump was usually higher when fly ash was used, in agreement with Ukita et al. (1989, Fly Ash, Silica

TABLE 9

Percentage Compressive Strength of the
Fractionated Dry Bottom boiler Fly Ash Concrete Over Time
(25% Replacement)

| Sample | Percentage Compressive Strength (%) | | | | | | |
|---|---|---|---|---|---|---|---|
| No. | 1-d | 7-d | 14-d | 28-d | 56-d | 90-d | 180-d |
| CCCC | 2157 | 6237 | 7141 | 8157 | 8707 | 9195 | 10161 |
| 13FC25 | 74.2 | 88.0 | 96.6 | 101.3 | 104.8 | 107.2 | 109.9 |
| 15FC25 | 71.8 | 86.1 | 93.4 | 96.3 | 100.9 | 104.9 | 106.2 |
| 16FC25 | 68.6 | 82.8 | 88.8 | 92.2 | 97.5 | 102.6 | 103.6 |
| 18FC25 | 64.4 | 78.2 | 84.4 | 87.5 | 90.8 | 93.8 | 96.2 |
| 18CC25 | 63.4 | 74.4 | 79.4 | 77.8 | 82.9 | 84.4 | 84.4 |
| CWET25 | 65.1 | 78.9 | 84.3 | 88.4 | 93.2 | 93.5 | 93.2 |

With 35% replacement of cement by fly ash in concrete, the compressive strengths were lower than those for 15% and 25% replacement, especially at the early ages (FIG. 3C). The compressive strength of fractionated fly ash concrete at 1 day varied from 851 psi to 1460 psi, moving from coarse to fine particle size ranges. Most strengths of fractionated fly ash concrete were lower than the control concrete at all ages. The notable exception was the sample with the finest particle size range of fly ash, 13FC35. The strength of sample 13FC35 varied from 1460 psi at 1 day to 10788 psi at 180 days, or from 67.6% to 106.2% of the control. The strength of fly ash concrete with 35% replacement was as high as the control strength by 90 days with the 13F fly ash fraction. With the original feed of wet bottom boiler fly ash, CWET35, had a compressive strength at 180 days about 90% of the control strength.

Fume, Slag, and Natural Pozzolans in Concrete, SP-114, American Concrete Institute, Detroit, pp. 219–240). Incorporation of fly ash in concrete often improves workability, which in turn reduces the amount of water required compared to conventional concretes (Lane and Best, 1982, supra; ACI 226 1987, "Use of Fly Ash in Concrete," ACI 226-3R-87, ACI J. Proceedings 84:381–409; Yamato and Sugita, 1983, Fly Ash, Silica Fume, Slag, and Other Mineral By-Products in Concrete, SP-79, American Concrete Institute, Detroit, pp. 87–102).

The results of this experiment show that only the finest fly ash reduced the workability of fresh concrete, especially when high quantities of fly ash were used. The other sizes of fly ash increased slump. These observations are explainable by the fact that, since the weight of fly ash was kept constant, the finer particle fly ash with greater surface area required more water to maintain the same workability as coarser sizes of fly ash.

With 50% fly ash of the finest particle size in the cementitious materials, the fly ash concrete samples of dry and wet bottom boiler fly ashes, 3FC50 and 13FC50, were less workable than those of the control concrete, which had a slump of about 5 cm. The slump of fly ash concrete from the original feed fly ashes was slightly higher than the control. For the original feed fly ashes, samples from the dry bottom boiler fly ash, CDRY, were found to be more workable than those from the wet bottom boiler fly ash, CWET. This may be because the particle sizes of the dry bottom boiler fly ash were larger than those of the wet bottom boiler fly ash. With the same amount of fly ash in the mix, the coarsest particle sizes, 1CC and 18CC, had a little lower slump than the original feed fly ash concrete.

Example 4

Setting Time of Fractionated Fly Ash-Cement Paste

The setting times of fly ash-cement paste increased with the increased the amount of fly ash in the paste. The same results were also reported by Ravina (1984, Concrete Int'l: Design and Construction 6:35-39), Meinlinger (1982, Concrete Int'l: Design and Construction 11:591-603), and Lane and Best (1982, supra). The initial and final setting times were slightly changed with the 15% replacement of the fractionated dry and wet bottom boiler fly ashes. The initial setting time of fractionated fly ash-cement paste was about 2 h and 55 min, while the setting time of the cement paste was 2 h 40 min. The final setting times of fly ash-cement paste with 15% replacement (dry or wet bottom boiler fly ash) were about 25 minutes longer than the final setting time of the cement paste.

With 25% replacement, the initial setting times increased 20 to 35 minutes from the initial setting time of cement paste, depending on the particle size of fly ash. The fine particle size fly ash fraction cement paste seemed to set taster than the paste using coarse fly ash fractions. For the dry bottom boiler fly ash, the initial and final setting times of sample 3F were 3 h and 6 h, respectively while the initial and final sets of the sample 1C were 3 h, 10 min and 6 h, 10 min, respectively. The setting time of the sample using the original teed of wet bottom boiler fly ash was slightly shorter than that of the dry one.

When the replacement of fly ash increased to 35% by weight of cementitious materials, the setting times increased compared to samples with 15% and 25% replacement. The initial setting times of fractionated fly ash-cement paste were usually about 3 h, 20 min. The final setting times of samples from the fractionated dry bottom boiler fly ashes were longer than those for the fractionated wet bottom boiler fly ashes by about 20 to 30 minutes. With 35% replacement with the fractionated dry bottom boiler fly ashes, the final setting times were about 1 hour longer than the final setting time of the control cement paste. With the same replacement of the fractionated wet bottom boiler fly ashes, the final setting times were about 40 minutes longer than for the cement paste.

With 50% of fly ash in the fly ash-cement paste, the initial setting times of the fractionated dry bottom boiler fly ashes were about 1 hour longer than the setting time of the cement paste control. In general, the initial and final setting times of the fractionated wet bottom boiler fly ash samples were shorter than those of the dry bottom boiler fly ash samples. This may have been due to the fact that the fractionated wet bottom boiler fly ashes have higher CaO content than the dry bottom boiler fly ashes. The CaO content of the originated of wet and dry bottom boiler fly ashes was 6.89% and 2.41%, respectively. Since CaO can react with water and set like cement, extra CaO may have resulted in setting of the fractionated wet bottom boiler fly ash pastes set faster than the dry bottom boiler fly ash paste.

Example 5

Compressive Strength of Concrete Containing Fractionated Fly Ash and Silica Fume Concrete mixtures containing the finest fraction of both dry bottom boiler and wet bottom boiler fly ash (fractions 3F and 13F, respectively) or silica fume were prepared to compare the independent effects of each of these components on the rate of compressive strength gain for concrete. These agents were used as a 15% or a 25% replacement for cement in the cementitious materials of the concrete.

Superplasticizer (Daracem-100) was added to reduce the amount of water required for the mixture. In the mixture containing 25% fly ash or silica fume as a replacement for cement, 10 ml per pound of cementitious materials (cement and silica fume or fly ash) of superplasticizer was used.

A control sample (labeled CSF) was prepared, which contained neither fly ash nor silica fume. The labels CSF15 and CSF25 refer to concrete containing 15% and 25%, respectively, silica fume for cement. The labels C3F15, C3F25, C13F15, and C13F25 refer to samples 3F and 13F, respectively, containing 15% or 25% fly ash for cement, respectively.

Figure 4A:
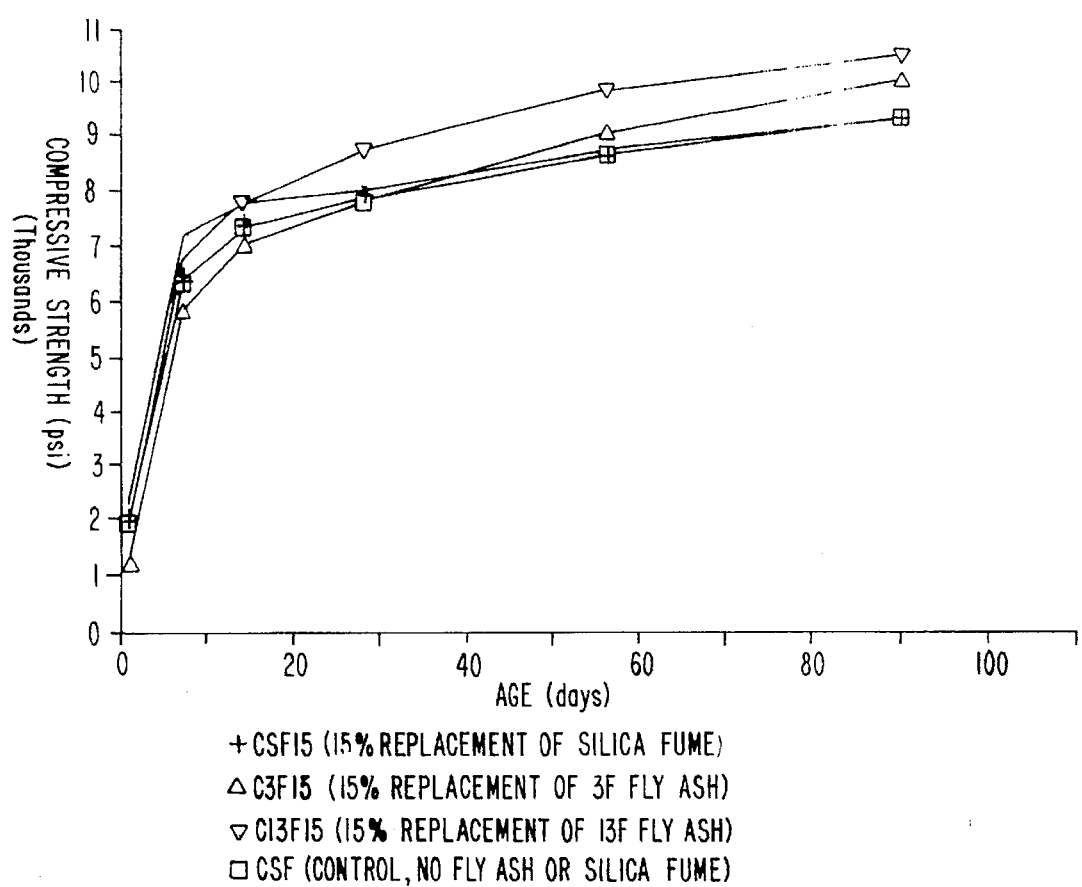
FIG. 4 presents graphs showing the compressive strength gain over time of concrete samples in which cement is replaced with 15% (A) or 25% (B) with either silica fume or the finest fraction of fractionated dry bottom boiler or wet bottom boiler fly ash. (A) CSF15 (plus sign, replacement with silica fume); C3F15 (open triangle, replacement with dry bottom boiler fraction 3F); C13F15 (inverted open triangle, replacement with wet bottom boiler fraction 13F); and CSF (open square, control containing neither fly ash nor silica fume). (B) CSF25 (open diamond, replacement with silica fume); C3F25 (X, replacement with dry bottom boiler fraction 3F); C13F25 (closed square, replacement with wet bottom boiler fraction 13F); and CSF (open square, control containing neither fly ash nor silica fume).

Table 10 and FIG. 4A shows the compressive strength over time of compositions in which fly ash or silica fume replace 15% or 25% of the cement.

TABLE 10

Compressive Strength of the Fractionated Fly Ash and Silica Fume Concrete (15% and 25% Replacement)

| Sample No. | Percentage Compressive Strength (%) | | | | | | Slump (cm) |
|---|---|---|---|---|---|---|---|
| | 1-d | 7-d | 14-d | 28-d | 56-d | 90-d | |
| CSF* | 1912 | 6352 | 7346 | 7881 | 8645 | 9322 | 23 |
| CSF15 | 122.1 | 113.0 | 105.7 | 101.6 | 109.9 | 99.6 | 1 |
| CSF25 | 139.9 | 104.9 | 101.8 | 101.9 | 98.4 | 97.9 | 0 |
| C3F15 | 63.6 | 92.2 | 96.1 | 99.2 | 104.5 | 107.5 | 21 |
| C3F25 | 63.4 | 94.0 | 98.7 | 109.7 | 113.1 | 112.9 | 20 |
| C13F15 | 101.7 | 106.8 | 106.2 | 110.9 | 114.0 | 112.5 | 16 |

TABLE 10-continued

Compressive Strength of the Fractionated Fly Ash
and Silica Fume Concrete
(15% and 25% Replacement)

| Sample No. | Percentage Compressive Strength (%) | | | | | | Slump (cm) |
|---|---|---|---|---|---|---|---|
| | 1-d | 7-d | 14-d | 28-d | 56-d | 90-d | |
| C13F25 | 93.2 | 95.9 | 98.6 | 108.6 | 113.6 | 115.3 | 12 |

*The values for the control are the compressive strength in psi; all other values are the percentage of control compressive strength at that time.

In these mixtures, cementitious materials, sand, course aggregate, water, and superplasticizer are held constant. Therefore, the consistency and compressive strength of the concrete depends on the components of the cementitious materials, i.e., the fly ash or silica fume and cement.

The data show that concrete containing 25% silica fume had no slump, while control concrete had a 23 cm slump. Since silica fume is very fine particle material, it has more surface area than cement on a per weight basis. In general, when the mix proportion of concrete is maintained constant, the mix with silica fume (powder) requires additional water to achieve a satisfactory slump.

Concrete containing fly ash also demonstrates a lower slump than control. Although fly ash concrete usually has more slump than control, the finest fractions of fly ash demonstrate the opposite behavior. Thus, the presence of these fractions in the concrete reduces the workability of the material. However, it is clear that fly ash does not serve to eliminate slum at the desired content in concrete, in contrast to silica fume.

The compressive strength of the control concrete varied from 1912 psi at day 1 to 9322 psi at day 180. Within 7 days, the compressive strength of CSF was 6352, which is considered a high strength concrete (ACI Committee 363, 1990, ACI *Manual of Concrete Practice Part I*, American Concrete Institute, Detroit).

The compressive strength of CSF15 and CSF25 (which contain silica fume) after 1 day were 2335 and 2675 psi, respectively, or 22.1% and 39.9% stronger than control. Concrete containing silica fume achieved early compressive strength gains. This behavior can be attributed to both packing and pozzolanic effects. Because the particle sizes of silica fume are very small, they fill the voids of the concrete matrix and make concrete denser and more compact after casting. During the curing period, the pozzolanic reaction by silica fume takes place at a faster rate than observed for fly ash probably because it is much finer. After 28 days, however, the rate of strength gain of silica fume concrete slows, and its absolute strength falls below that of the control. The percentage of control strength of high strength silica fume concrete with 25.5% replacement goes from 139.9% on day 1 to 97.9% on day 90.

High strength concrete made from the finest fractions of fly ash behaves differently. Early strength gains by fly ash concrete occur much more slowly than with control. With 15% replacement of 3F fly ash, the compressive strength of fly ash concrete varies from 1216 psi at day 1 to 10023 psi at day 90, a shift form 63.4% of control strength to 107.5% of control strength. This trend was observed with other fly ash concretes tested as well. The strength variation of high strength fly ash concrete with 25% replacement of 13F fly ash varies from 1782 psi at day 1 to 10748 psi at day 90. The values for the 25% fly ash concrete were lower during the first 14 days than the corresponding compressive strength values of the 15% replacement concrete. However, after 90 days, the concrete with a greater percentage of fly ash is stronger.

The expected compressive strength of the C3F15 sample at day 1 is 80% of control. The lower value actually observed (63.4%) may be due to the high dose of superplasticizer used, which was about three times higher than the manufacturer's recommendation. A high dose of superplasticizer tends to retard the setting of cement, resulting in lower compressive strength early on. This effect was not pronounced with the fraction of wet bottom boiler fly ash, 13F.

After 7 days of curing, the rate of compressive strength gain of the fly ash concrete samples returned to the expected level. The fly ash concrete was considered to be high strength after seven days of curing, since at this time the compressive strength of the samples is over 6000 psi.

Before day 7, the highest strength is found in the samples containing silica fume. After 14 days, samples CSF15 and C13F15 have comparable strengths, at about 7800 psi. At day 28 of curing, high strength concretes using fly ash as a replacement produced stronger concrete than for either the control or the silica fume concrete. The strength of samples C13F15, C13F25, and C3F25 were 8740 psi, 8561 psi, and 8648 psi, respectively. As the concrete ages, the fly ash continues to contribute to values for compressive strength that are higher than control values. At about 90 days, the compressive strengths of fly ash concrete are much higher than control.

It is interesting to note that the compressive strength of concrete made with silica fume (containing either 15% or 25%) have almost the same strength as the control strength at 90 days. These values range from 9100 psi to 9300 psi. The results of this experiment clearly show that while the silica fume contributes to a more rapid initial gain in compressive strength, after about a week the rate becomes much slower. The data suggest that a mixture containing silica fume, for rapid strength gain, and fly ash, for long term compressive strength gain, may be particularly advantageous.

Example 6

Effect of Fractionated Fly Ashes on the Strength of Mortar

In addition to the study of fractionated fly ash concrete, mortar was also tested. The fractionated fly ashes from the dry and wet bottom boilers were used as a replacement for cement in the mortar at 15%, 25%, and 50% by weight of cementitious (cement+fly ash) materials. The water to cementitious materials ratio was kept constant at 0.5. Control mortar without any fly ash replacement, using the same mix proportion and the same water to cementitious materials ratio, was also mixed and cast. The mix proportion is shown in Table 1. After casting 24 hours, the 2"×2"×2" cube samples were removed from the mold and cured in saturated lime water prior to testing. The compressive strength of samples were tested after 1, 3, 7, 14, 28, 56, 90, and 180 days of aging.

CF is the control sample. Samples "DRY" and "WET" were the mortars with the original feed of dry and wet bottom boiler fly ashes, respectively. The numbers "15", "25", and "50" stand for the percentage of cement replaced by fly ash in the mortar. Fractionated fly ash samples are described above (see Table 3). For example, the 3F15 sample is fly ash mortar using 3F fly ash as a substitute for cement to 15 percent by weight of cementitious materials. Likewise, 6F15 is the fly ash mortar using 6F fly ash as a replacement for cement 15 percent by weight of cementitious materials.

Figure 5A:
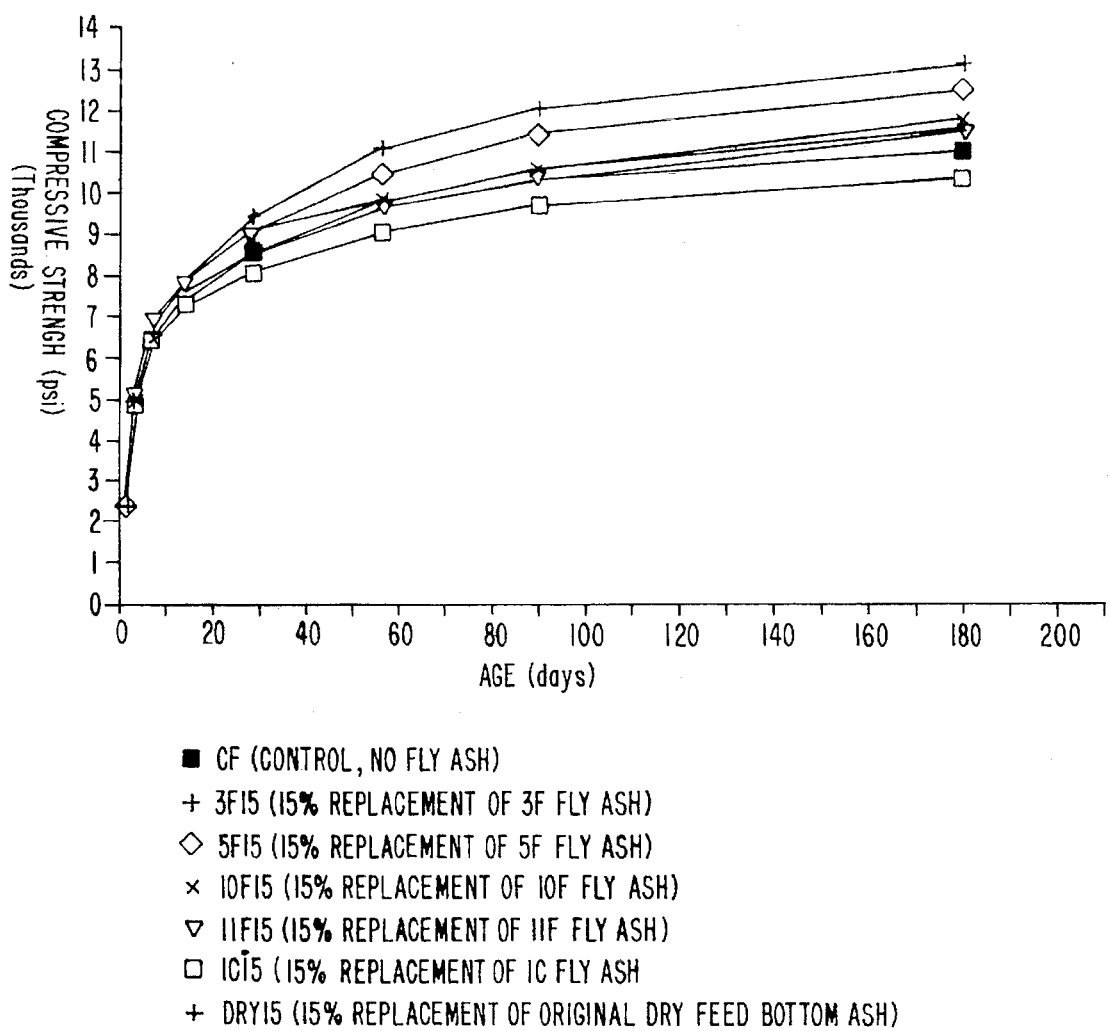
FIG. 5 presents graphs showing the compressive strength of mortar samples containing 15% fly ash as a replacement for cement with age. (A) Feed and fractionated dry bottom boiler fly ash as described in FIG. 1 and the Examples: CF (open squares, control containing no fly ash); 3Fxx (plus sign, 3F fly ash fraction, in which xx stands for the percent replacement of cement with fly ash); 5Fxx (open diamond, 5F fly ash fraction); 10Fxx (X, 10F fly ash fraction); 11Fxx (open inverted triangle, 11F fly ash fraction); 1Cxx (open squares [of much lower compressive strength than control], 1C fly ash fraction; and DRYxx (plus signs [of lower compressive strength than the 3F-containing samples], feed dry bottom boiler fly ash). (B) Feed and fractionated wet bottom boiler fly ash as described in FIG. 1 and the Examples: CF (open squares, control containing no fly ash); 13Fxx (plus sign, 13F fly ash fraction, in which xx stands for the percent replacement of cement with fly ash); 14Fxx (open diamond, 14F fly ash fraction); 15Fxx (X, 15F fly ash fraction); 18Fxx (open inverted triangle, 18F fly ash fraction); 18Cxx (open squares [of much lower compressive strength than control], 18C fly ash fraction; and WETxx (plus signs [of lower compressive strength than the 13F-containing samples], feed wet bottom boiler fly ash).
Figure 5B:
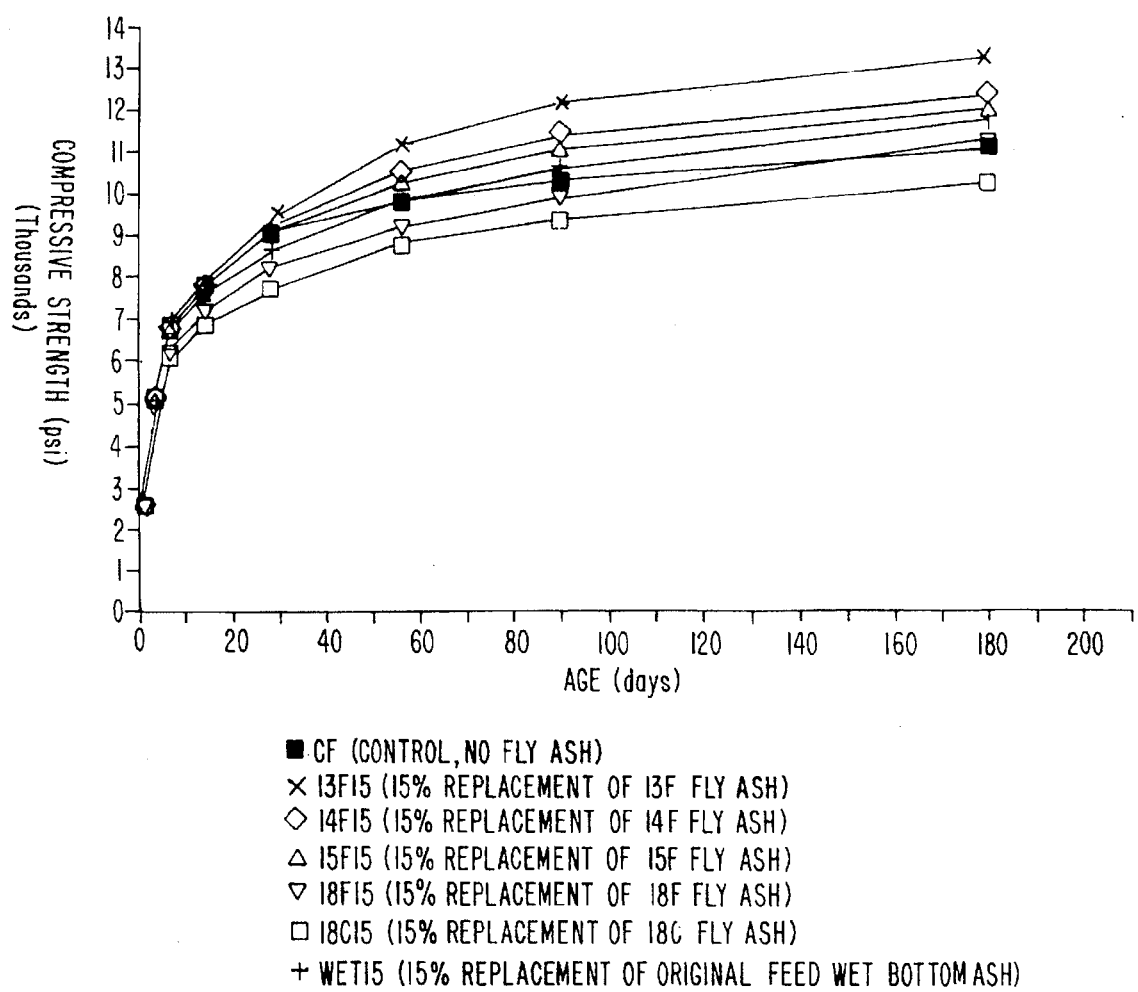

The relationship between the compressive strength of fractionated fly ash mortar and age is shown in FIG. 5A (dry bottom boiler fly ash) and FIG. 5B (wet bottom boiler fly ash).

As expected, and as observed in the tests with concrete mixtures, the early age strengths of fly ash mortar were lower than the control mortar. With 15% replacement with fractionated fly ash, the compressive strength was no more than 80% of the control mortar strength at 1 day. The compressive strengths of fractionated fly ash mortars gradually increased with age, depending on the average and range of volumes of fly ash particles. As observed with concrete, the strength of fly ash mortar increased with the decrease in the particle size range of fractionated fly ash. Compressive strength varied from 2290 psi for coarse particles to 2666 psi for fine particles. At all curing ages, the lowest compressive strength was found in samples containing coarse particles of fly ash (1C15 and 18C15).

Up to 14 days, the compressive strengths of all fly ash mortars were lower than the control, except for the samples containing the finest fly ash fractions (3F15 and 13F15). The compressive strengths of samples 3F15 and 13F15 at 14 days were 7968 psi and 7925 psi, respectively. These strengths represent 101.1% and 100.5% of the control strength. After 180 days of curing, all samples of fractionated fly ash mortar demonstrated greater strength than the control sample, except samples 1C15 and 18C15, which were made up of the coarsest particles of each type of fly ash. The compressive strengths of 1C15 and 18C15 were 93.6% and 92.7%, respectively, of the control at 180 days.

In summary, these results show that at the same age and for the same type of fly ash, the finer the particle size of fly ash in the mortar, the higher the compressive strength of the mortar will be.

It was noted that the strength of the mortar made from the non-fractionated wet bottom boiler fly ash (WET15) was slightly higher than that from the non-fractionated dry bottom boiler fly ash. Although the non-fractionated wet bottom boiler fly ash could be expected to have a greater glassy phase than non-fractionated dry bottom boiler fly ash, preliminary state-of-the-art X-ray diffraction results could not distinguish a significant difference in the glassy phase. This observation suggests that both fly ashes have about the same degree of glassy phase. As will be show below the difference in compressive strength between these non-fractionated samples correlates with the fineness modulus of the samples.

Figure 6A:
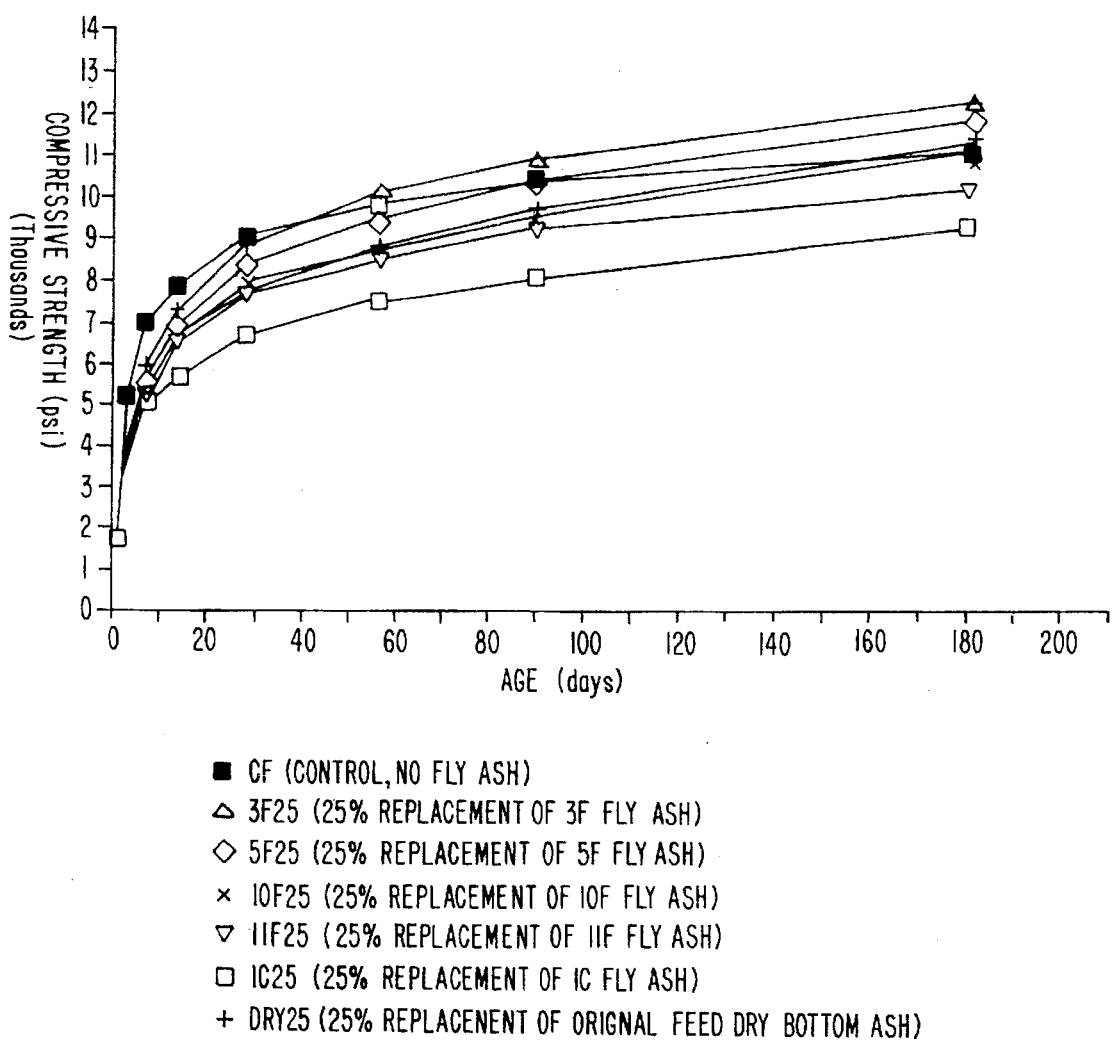
FIG. 6 presents graphs similar to FIG. 5 showing the compressive strength of mortar samples containing 25% fractionated or non-fractionated dry bottom boiler fly ash (A) or wet bottom boiler fly ash (B) as a replacement for cement, with age. The symbols are the same as for FIG. 5.
Figure 6B:
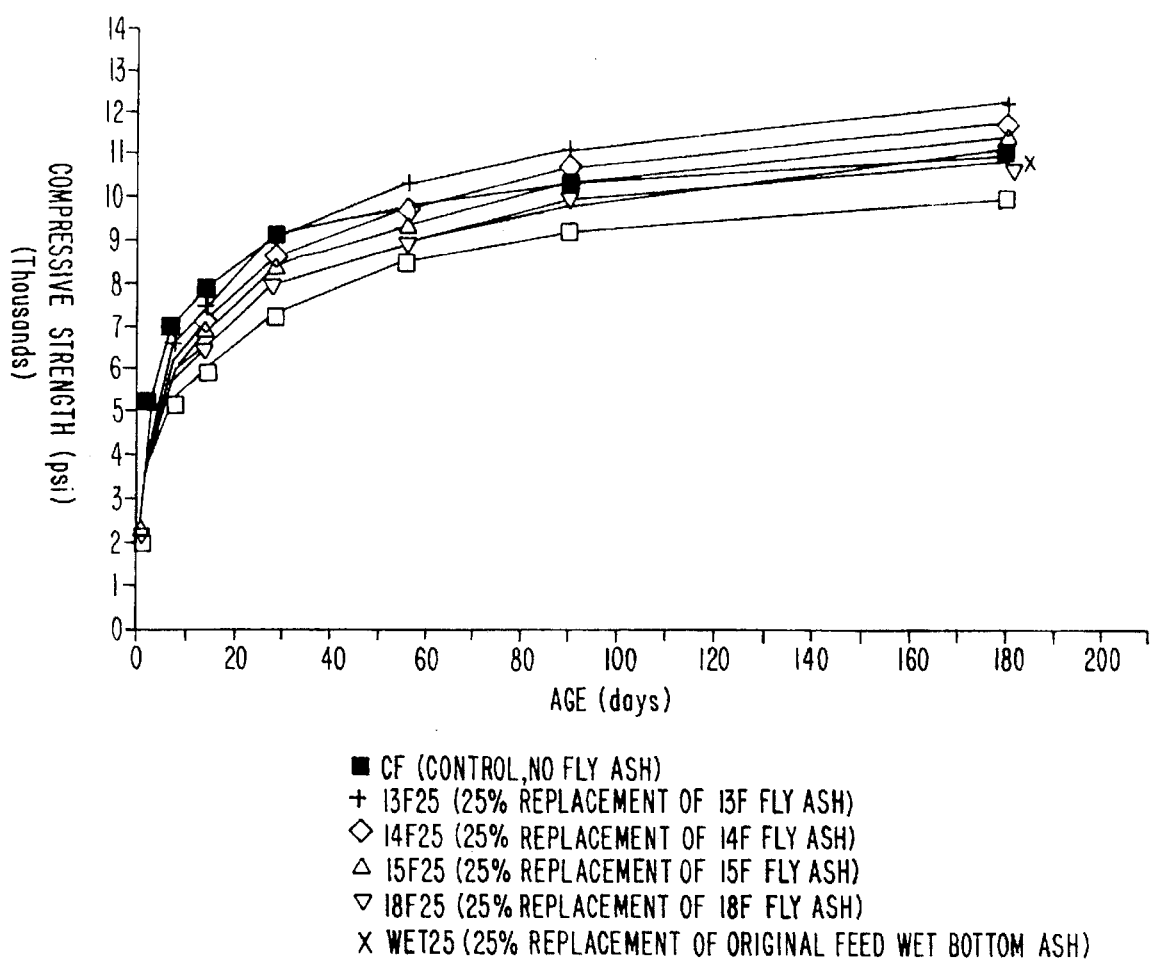

The compressive strength of fractionated fly ash mortar with 25% replacement was somewhat lower than that with 15% replacement (FIGS. 6A and B), although the trend was the same. All of the early strengths of the fractionated of dry bottom boiler fly ash mortars were lower than the control mortar for up to 28 days. With 25% replacement, the strength of mortar from the original feed (dry or wet bottom boiler fly ash) was only about 30% of the control strength at 1 day. For replacement with the fractionated wet bottom boiler fly ashes, most of fly ash mortar samples demonstrated lower compressive strength than the control strength at the age of 28 days, except for sample 13F25. The compressive strength of 13F25 was 9112 psi, or 100.2% of the control, at 28 days. Replacement with the original feed of dry and wet bottom boiler fly ashes yield compressive strengths of 7821 psi and 8031 psi, respectively, or 86% and 88.3%, respectively, of the control mortar at 28 days. As noted above, the compressive strength of mortar from the original feed of wet bottom boiler fly ash was slightly higher than the mortar made from the original feed of dry bottom boiler fly ash. The compressive strength of fly ash mortar containing 25% coarse fly ashes, i.e. 1C25 and 18C25 were 83.4% and 91.1% of control, respectively at the age of 180 days.

Thus, for both types of fly ash, the compressive strength of fractionated fly ash mortar increased with the decrease of fly ash particle size. After the age of 180 days, most of fly ash mortars achieved the same or higher compressive strength than the control, except for mortar made with the coarsest particle size distributions (11F, 1C, and 18C) of fly ash. The original feed of fly ash required 180 days of curing to gain the same compressive strength as the control. The results further demonstrate that the use of fine fractionated fly ash increases the rate of pozzolanic activity. The finer the particle sizes in the fly ash fraction, the greater the rate of the strength development.

Figure 7A:
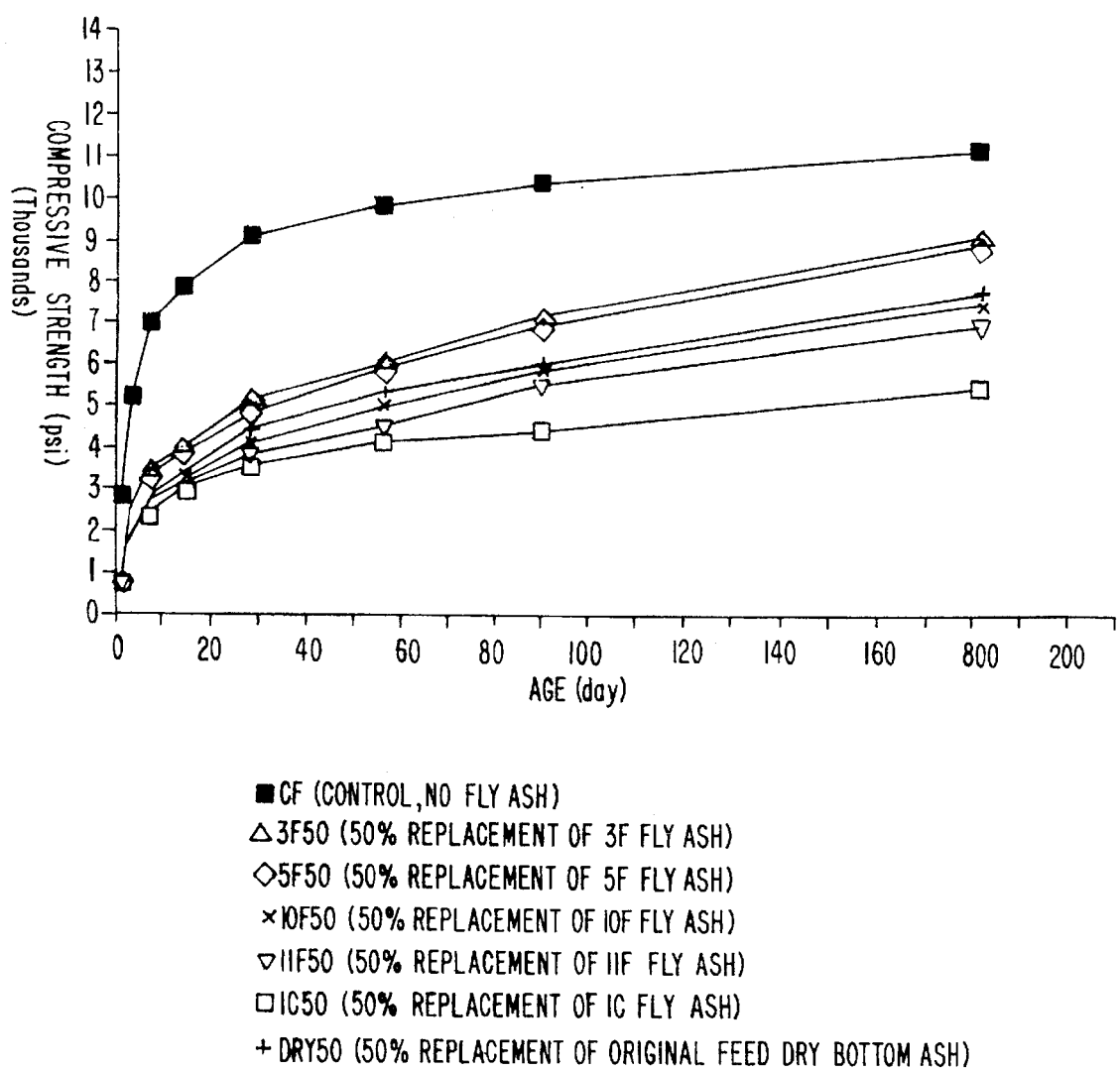
FIG. 7 presents graphs similar to FIGS. 5 and 6 showing the compressive strength of mortar samples containing 50% fractionated or non-fractionated dry bottom boiler fly ash (A) or wet bottom boiler fly ash (B) as a replacement for cement, with age. The symbols are the same as for FIG. 5.
Figure 7B:
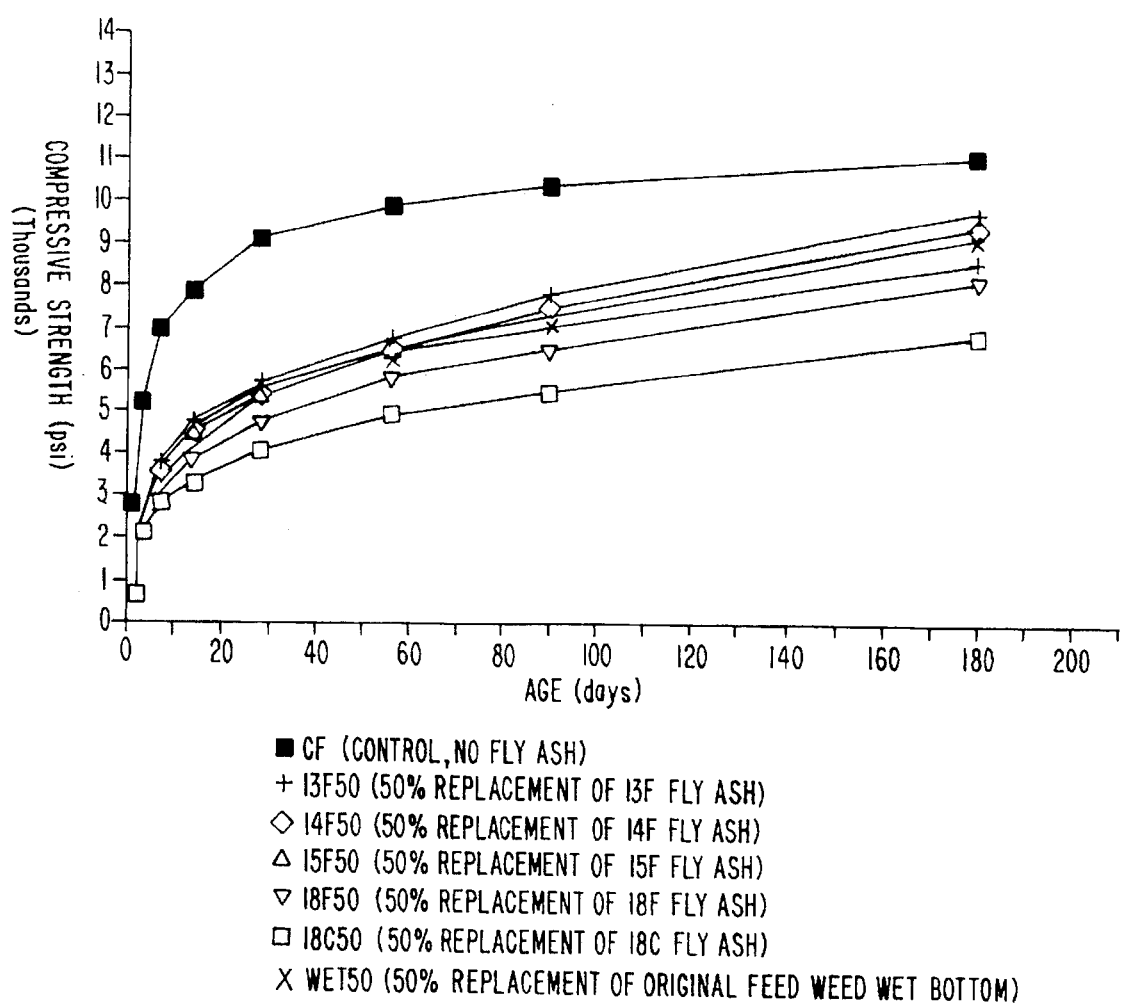
Figure 8A:
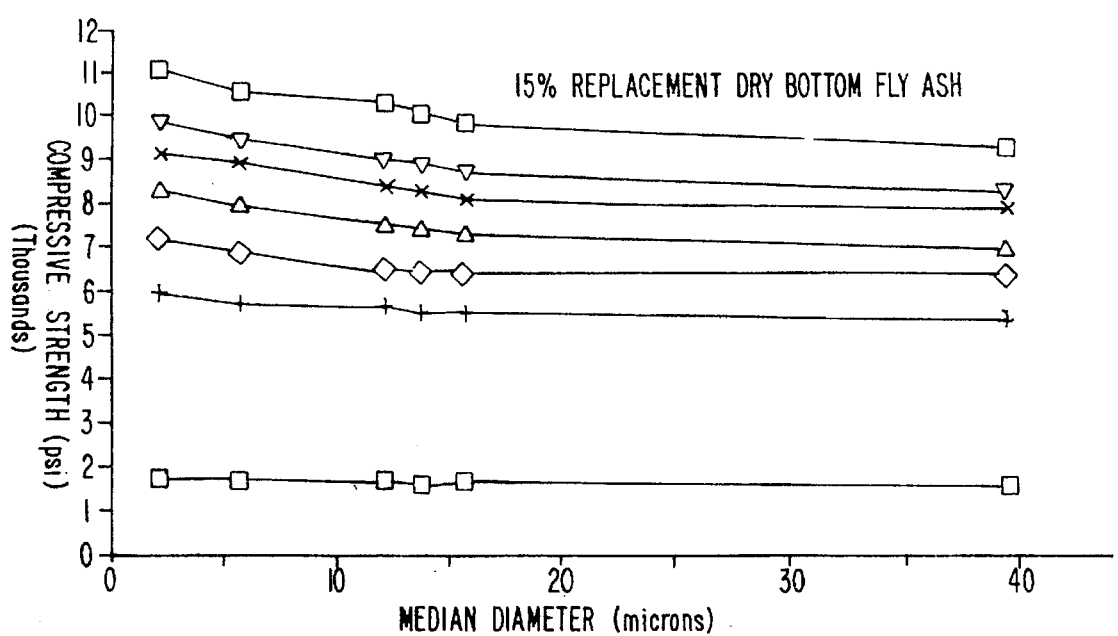
FIG. 8 presents graphs showing the relationship between compressive strength and median fly ash diameter for fractionated dry bottom boiler fly ash concrete. The concrete samples contain 15% (A), 25% (B), 35% (C), and 50% (D) fly ash as a replacement for cement. Compressive strength was determined at day 1 (open square), day 7 (plus sign), day 14 (open diamond), day 28 (open triangle), day 56 (X), day 90 (inverted open triangle) and day 180 (open square, with much high compressive strength values than the values at day 1).
Figure 8B:
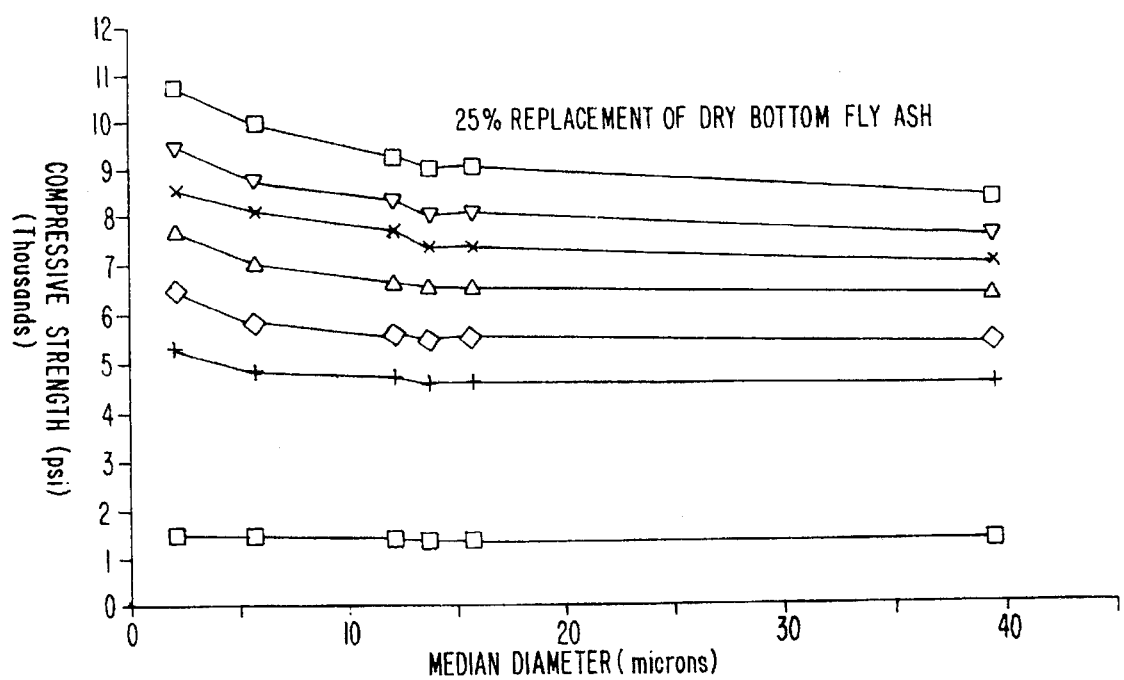
Figure 8C:
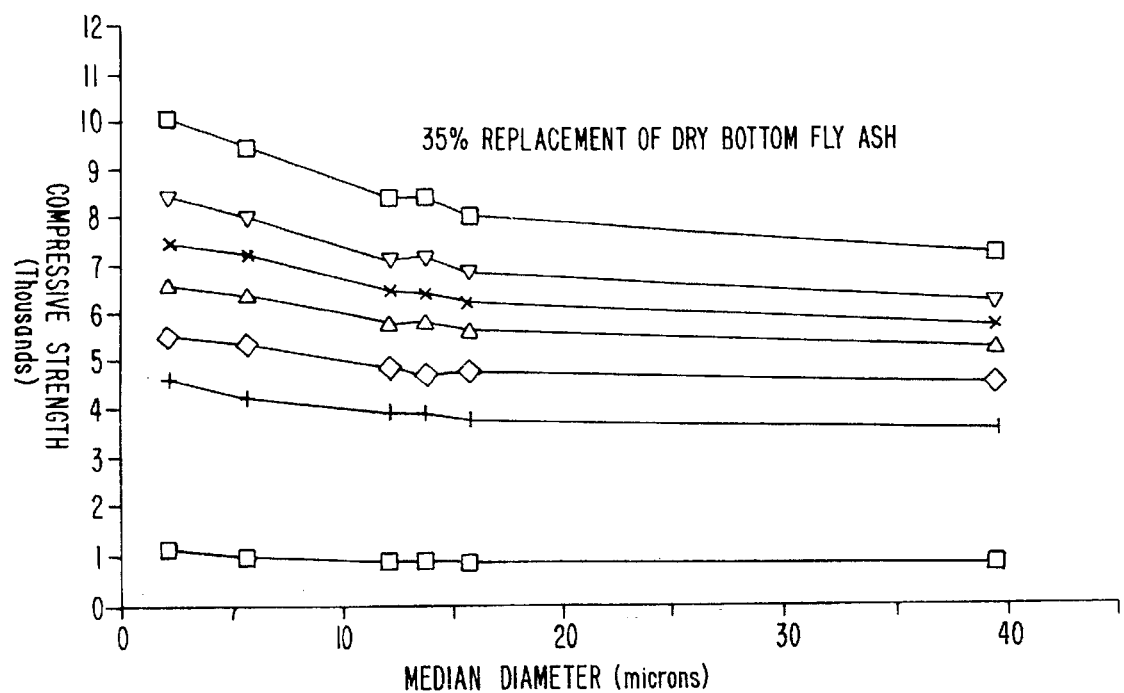
Figure 8D:
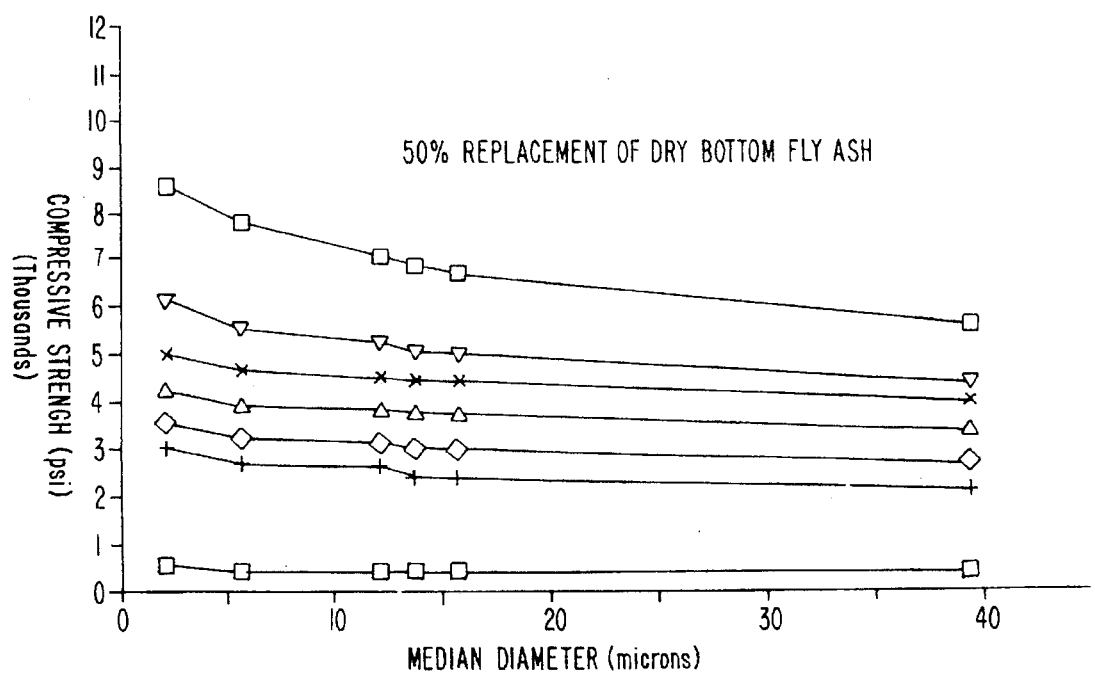
Figure 9A:
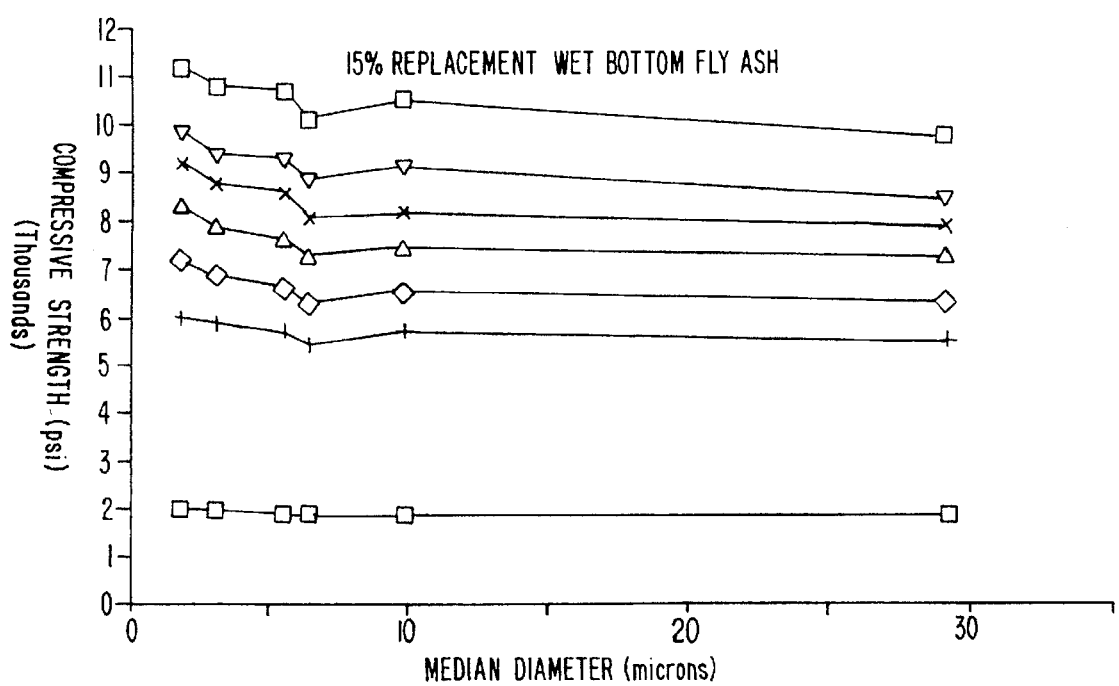
FIG. 9 presents graphs showing the relationship between compressive strength and median fly ash diameter for fractionated wet bottom boiler fly ash concrete. The concrete samples contain 15% (A), 25% (B), 35% (C), and 50% (D) fly ash as a replacement for cement. The symbols are the same as for FIG. 8.
Figure 9B:
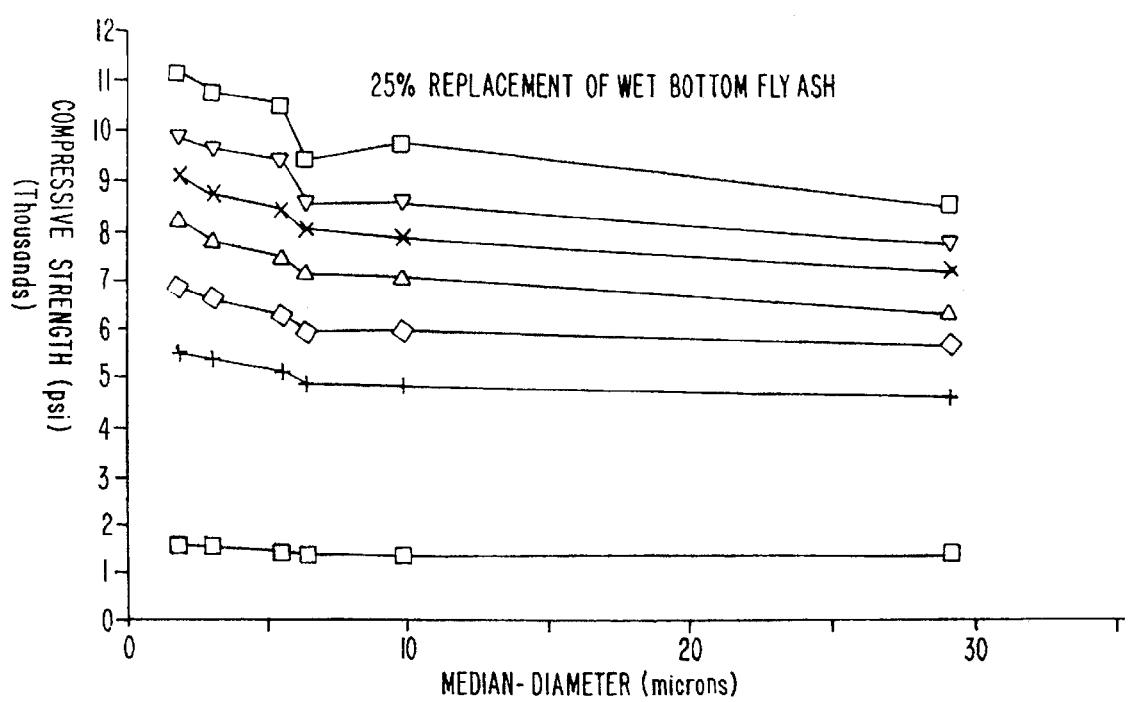
Figure 9C:
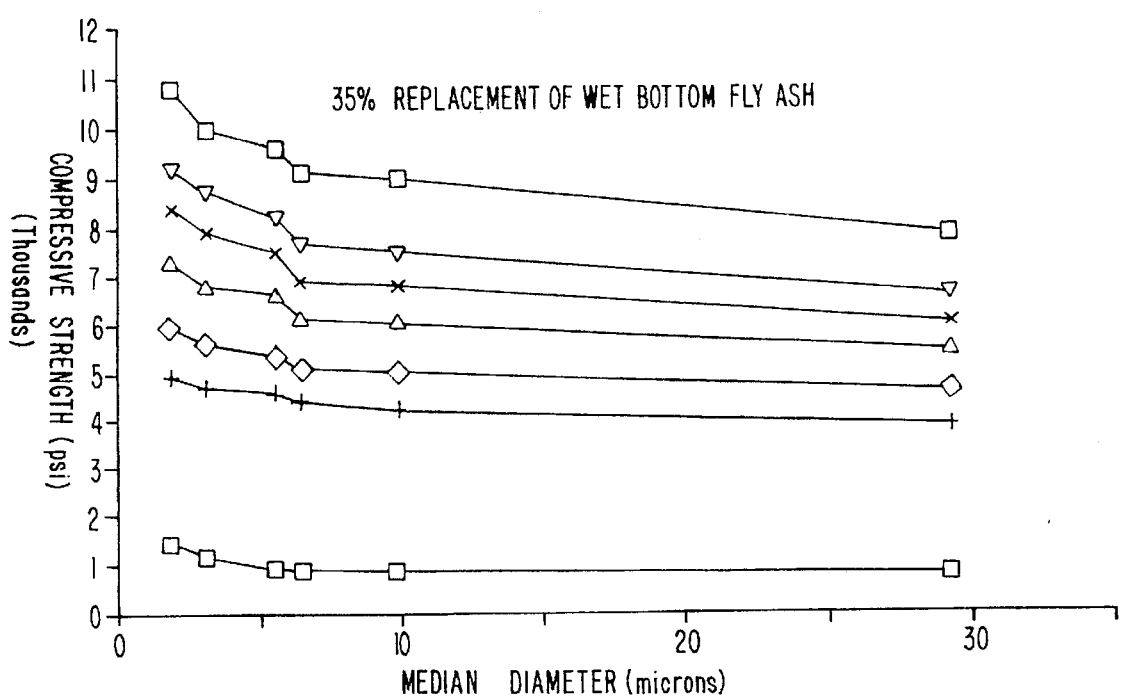
Figure 9D:
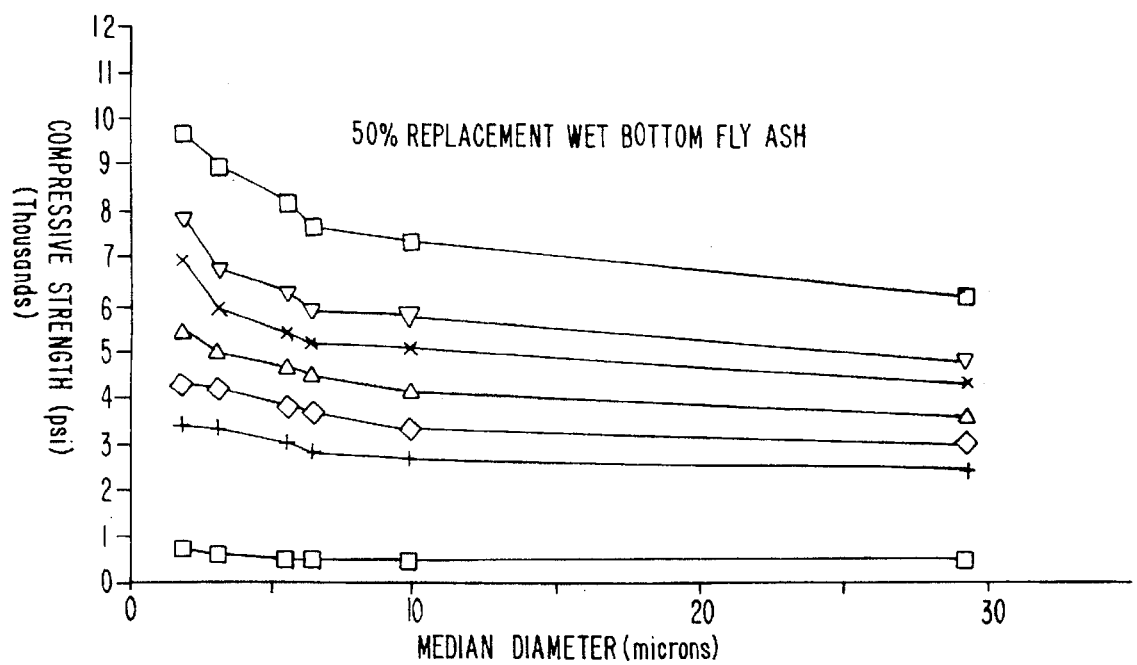

With 50% replacement of fly ash in the mix, the early strengths of fly ash mortar were very low (FIGS. 7A and 7B). All strengths of fractionated fly ash mortars at 1 day were less than 50% of the control. The compressive strengths of fractionated fly ash mortars at 1 day varied from 711 psi to 1322 psi, depending on the particle size range of the fly ash fraction. The percentage compressive strength of sample 3F50 varied from 46.4% at 1 day to 81.6% at 180 days. The respective compressive strengths of the original feed dry and wet bottom boiler fly ash mortar samples were 26.2% and 30.2% of the control mortar. For the original feed of dry bottom boiler fly ash sample, DRY50, the compressive strength was 747 psi at 1 day, and increased to 7642 psi at 180 days. In general, as was noted above, the compressive strength of the original feed of wet bottom boiler fly ash was higher than that of dry bottom boiler fly ash. After 180 days, all of the fractionated fly ash mortar samples demonstrated lower compressive strength than the control. The graphs of FIGS. 10A and 10B suggest that the mortar samples made with fine fly ashes, i.e., 3F50, 6F50, 14F50, and 15F50, continued to gain strength after 180 days. According to Hensen (1990, Cement and Concrete Research 19: 194–202), the pozzolanic activity of fly ash continues for up to 3 years after casting concrete or mortar.

Example 7

Compressive Strength Is Independent of Median Particle Diameter and Total Surface Area The relationship between compressive strength and median diameter of the fractionated dry bottom boiler fly ash is shown in FIG. 8A–8D. It may be observed that there is little difference in compressive strength exhibited by the fractionated fly ash samples 11F (15.69 microns) and 1C (39.45 microns) when the median diameter is above 15 microns, with curing times up to 56 days. However, as the median diameter of the fractionated fly ash becomes less than 15 microns, differences are observed in the compressive strengths exhibited by the concrete samples prepared with these different fractionated fly ashes. These are observed alter seven days of curing. At one day of curing, the compressive strength exhibited by the concrete appears to be independent of the median particle diameter.

Similar results are observed with the concrete samples prepared with the fractionated and non-fractionated wet bottom boiler fly ash, as shown in FIG. 9A–9D. The compressive strength of the fractionated fly ash concrete 18F and 18C, with the largest particle sizes, containing different amounts of fly ash replacement of cement with fly ash remain essentially constant with curing time up to 56 days. Below the 10 micron limit, the compressive strength again increases with a decrease in the median particle diameter after seven days of curing.

However, when one examines the relationship between compressive strength exhibited by the non-fractionated dry and wet bottom boiler fly ashes and their median particle diameter, there is deviation of the compressive strength point for the non-fractionated fly ash sample from the points obtained with the fractionated fly ash samples. This deviation is not as significant for the non-fractionated dry bottom boiler fly ash (median diameter 13.73 microns) as it is for the non-fractionated wet bottom boiler fly ash (median diameter 6.41 microns). When a broad distribution of sizes of non-fractionated fly ash is used in the concrete, the relationship between the compressive strength and the median particle diameter is different than that obtained when fractionated fly ash, with a narrow particle size distribution, is used.

The relationship between the compressive strength of the non-fractionated dry bottom boiler and wet bottom boiler fly ash and their total surface areas as measured by Blaine fineness also deviates from that obtained with the fractionated fly ashes. In a comparison of the compressive strengths exhibited by the non-fractionated dry bottom boiler fly ash (Blaine 3235 $cm^2/g$, median diameter 13.73 microns) and the 10F fraction (Blaine 2028 $cm^2/g$, median diameter 12.12 microns) (see FIG. 8A–8D), the 10F concrete sample in general exhibits a greater compressive strength than the non-fractionated dry bottom boiler concrete sample, even though its total surface area is significantly less than the total surface area of the non-fractionated fly ash concrete as measured by Blaine fineness.

The difference in compressive strength is more significant when the compressive strength of the non-fractionated wet bottom boiler fly ash concrete (Blaine 5017 $cm^2/g$, median diameter 6.41 microns) is compared with the 16F fraction concrete sample (Blaine 5171 $cm^2/g$, median diameter 5.5 microns). Here the Blaine fineness is comparable and median diameter is not significantly different (see FIG. 9A–9D) to the non-fractionated wet bottom boiler fly ash sample.

These results indicate that both the size of the fly ash particles and the distribution of the particle sizes must be considered in defining compressive strength, especially when the predominant particle sizes in the fly ash is below the 10 micron to 15 micron range.

The compressive strength development resulting from the reaction between the cement and fly ash appears to be primarily particle volume dependent and not surface area dependent. After seven days of curing the concrete, the smaller particles in the fractionated fly ashes with the smallest particle sizes have probably reacted completely. Thus, the compressive strengths of these fractionated fly ash-concrete samples are measured to be greater than those containing the larger particle sizes.

If the compressive strength development was primarily surface are dependent, compressive strength differences would be observed even after one day of curing. An examination of Table 5 shows the large variation in surface area, as represented by the Blaine fineness, exhibited by the fractionated fly ashes. Yet, the concrete samples containing these fractionated fly ashes show virtually no differences in the compressive strength after one day. In fact, the dry bottom boiler and wet bottom boiler fractionated fly ash concrete 11F and 1c, and 18F and 18C, respectively, containing the largest particle sizes, show no compressive strength difference even after 56 days of curing. In contrast, the influence of particle sizes on compressive strength is readily observed for the fractionated fly ashes with smaller particle sizes.

Example 8

Fly Ash Concrete Strength Model

Based on the observations disclosed above, a fly ash concrete strength model is proposed. This model considers the contribution to compressive strength of cement and fly ash in concrete or mortar at any given time point. Although the specific model and equation are derived for concrete compositions, the important variables and relationships of the variable described in the equation broadly apply to any hardenable mixture, whether concrete or mortar, that contains fly ash.

Two factors determine strength at time O: the amount of cement that is present, and any packing effect mediated by fly ash. With time, pozzolanic activity of fly ash with CaO created by the cement leads to a greater increase in compressive strength. Thus, the model includes the contribution of fly ash pozzolanic activity over time as well as packing effects mediated by the fly ash.

To simplify the calculation, the present example maintained the cementitious materials (cement and fly ash) in a constant ratio to water, sand (fire aggregate), coarse aggregate, etc. Compressive strength of fly ash concrete was thus predicted as a percentage of control strength.

The compressive strength of control concrete was obtained empirically from the concrete that has the same mix proportions, and setting conditions such as the fly ash concrete, i.e., the water to cementitious materials ratio, curing condition, type of aggregates, and other variable were kept constant. The difference between the control and fly ash concrete mix was that all of the cementitious materials in the control concrete were cement.

Most importantly, the critical measure of the contribution of fly ash to strength gain is a parameter termed the fineness modulus of fly ash.

The variables of the equation to predict compressive strength of fly ash concrete are thus fineness modulus of the fly ash, age of concrete, the ratio of cement to fly ash, and the strength of the control concrete.

Fineness Modulus of Fly Ash (FM)

Fineness modulus of fly ash (FM) in this Example is defined as the summation of the percentage of fly ash that retained on the following sieve sizes: 0, 1, 1.5, 2, 3, 5 10, 20, 45, 75, 150, and 300 microns. In general, very little fly ash retained on the sieve with the opening size larger than 600 microns. The fineness modulus of fly ash was used without units. The value of fineness modulus is a measure of how the distribution of particle sizes s of fly ash from one sample compare to other fly ash samples.

The fineness modulus of fractionated dry bottom boiler and wet bottom boiler fly ashes are presented in Tables 10 and 11, respectively. The fineness modulus of fractionated fly ashes was between 300 to 900. Fly ash 13F has the lowest fineness modulus (the finest fly ash), and 1C has the highest fineness modulus (the coarsest fly ash).

TABLE 11

Fineness Modulus of the Fractionated Dry Bottom boiler Fly Ashes

| Sieve Opening (Micron) | Percent Retained (%) | | | | | |
|---|---|---|---|---|---|---|
| | 3F | 6F | 10F | 11F | 1C | DRY |
| 300 | 0 | 0 | 0 | 0 | 1 | 0 |
| 150 | 0 | 0 | 0 | 0 | 4 | 1 |
| 75 | 0 | 0 | 0 | 0 | 17 | 8 |
| 45 | 0 | 0 | 0 | 1 | 44 | 20 |
| 20 | 0 | 0 | 5 | 20 | 80 | 40 |
| 10 | 0 | 5 | 60 | 82 | 99 | 55 |
| 5 | 10 | 53 | 94 | 96 | 100 | 70 |
| 3 | 35 | 78 | 96 | 97 | 100 | 80 |
| 2 | 55 | 83 | 97 | 98 | 100 | 87 |
| 1.5 | 75 | 90 | 97 | 100 | 100 | 92 |
| 1 | 93 | 94 | 98 | 100 | 100 | 95 |
| 0 | 100 | 100 | 100 | 100 | 100 | 100 |
| FM | 368 | 503 | 647 | 694 | 845 | 648 |

TABLE 12

Fineness Modulus of the Fractionated Wet Bottom boiler Fly Ashes

| Opening (Micron) | Percent Retained (%) | | | | | |
|---|---|---|---|---|---|---|
| | 13F | 15F | 16F | 18F | 18C | WET |
| 300 | 0 | 0 | 0 | 0 | 0 | 0 |
| 150 | 0 | 0 | 0 | 0 | 3 | 2 |
| 75 | 0 | 0 | 0 | 0 | 10 | 5 |
| 45 | 0 | 0 | 0 | 0 | 30 | 10 |
| 20 | 0 | 0 | 0 | 6 | 70 | 20 |
| 10 | 0 | 3 | 10 | 39 | 96 | 35 |
| 5 | 6 | 30 | 49 | 80 | 100 | 55 |
| 3 | 35 | 56 | 73 | 86 | 100 | 70 |
| 2 | 49 | 69 | 82 | 89 | 100 | 80 |
| 1.5 | 68 | 82 | 88 | 93 | 100 | 88 |
| 1 | 82 | 90 | 92 | 94 | 100 | 97 |
| 0 | 100 | 100 | 100 | 100 | 100 | 100 |
| FM | 340 | 430 | 494 | 587 | 809 | 562 |

The results disclosed above demonstrate that when fly ash is used to replace an equal amount by weight of cement in concrete or mortar, compressive strength of the concrete or mortar is inversely proportional to the fineness modulus of fly ash.

Fineness modulus of fly ash provides a more predictive measure of the compressive strength of concrete than other measures of fineness, such as the Blaine fineness and the residue on sieve No. 325. Concrete made up with 10F fly ash (Blaine 2028 cm$^2$/g) gave higher strength than concrete containing an equal amount of the original feed of dry bottom boiler fly ash (Blaine 3235 cm$^2$/g), which is the opposite of the expected result based solely on the observations described above (that finer fly ash particles give greater compressive strength results) and the values of Blaine fineness (greater surface area per gram of material is indicative of greater fineness).

Similarly, the 45 micron sieve test lacks predictive value. Fly ashes 3F, 6F, and 10F, which have zero value retained on sieve on sieve No. 325, yield remarkable differences in compressive strength when used in concrete or mortar.

Thus, neither method is suitable to provide an indication of the effect on compressive strength of fractionated fly ash. In contrast, using the fineness modulus of fly ash provides reliable information concerning the compressive strength of fly ash concrete and mortar.

The irrelevance of Blaine fineness, as well as the correlation to median diameter, to compressive strength of concrete is evident in the experimental data. For example, when fractionated wet bottom boiler fly ash replaced 35% of cement in cementitious materials in concrete, there was a clear relationship between median diameter and compressive strength at all time points, whereas compressive strength was independent of Blaine fineness at a value greater than about 4000–5000 cm$^2$/g. Similar data were observed for concrete in which dry bottom boiler fly ash was used for 35% of cementitious materials. In the latter case, compressive strength became independent of Blaine fineness above about 2000 cm$^2$/g.

Fly Ash Concrete Strength Predictive Formula

A specific formula for predicting fly ash concrete strength is in the form of:

$$\sigma(\%) = \sigma_c + \sigma_{FA} \quad (1)$$

in which $\sigma(\%)$ is the percentage compressive strength of fly ash concrete compared to control concrete;

$\sigma_c$ is the percentage compressive strength of concrete contributed by cement in the concrete mix, which is equal to:

$$\sigma_c = 0.010 C^2 \quad (2)$$

where C is the percentage of cement in the cementitious materials;

$\sigma_{FA}$ is the contribution to strength by the pozzolanic reaction between fly ash and cement at any age, and can be given as:

$$\sigma_{FA} = A + (B/FM) \ln(T) \quad (3)$$

where A is a constant for the packing effect contribution of fineness of fly ash to the strength of concrete. For dry and wet bottom boiler fly ashes, this constant can be expressed as:

$$A = 6.74 - 0.00528 FM \quad (4)$$

in which FM is the fineness modulus of fly ash.

B in formula (3) above is the value for the pozzolanic activity between fly ash and cement for any mix proportion or ratio. B depends on the fly ash content in the mix. With higher fly ash content, this constant is higher; it decreases as the percentage of fly ash in the mixture decreases. For fly ash content between 10% to 50% by weight of cementitious materials, the constant B can be expressed by the formula:

$$B = [1685 + 126C - 1.324 C^2] \quad (5)$$

Figure 10:
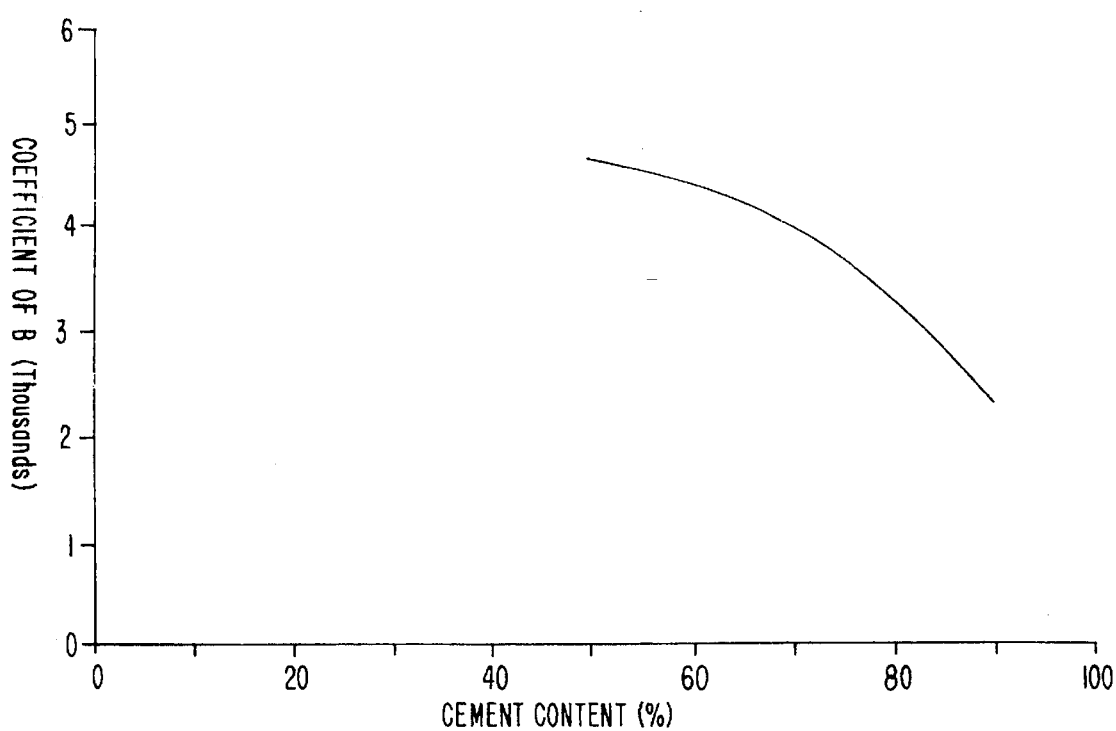
FIG. 10 is a graph showing the relationship between the a variable B (coefficient of B) in formulae 3, 5 and 6 and cement content of a concrete mixture. The cement content is expressed as a percentage, by weight, of cementitious materials in the mixture.

The value of T in equation (3) is the age of concrete in days. FIG. 10 graphically depicts equation B for 10% to 50% replacement of cement with fly ash.

Thus, the final form of the formula for predicting fly ash concrete strength is:

$$\sigma(\%) = 0.010 C^2 + [6.74 - 0.00528 FM] + \{B/FM[\ln(T)]\} \quad (6)$$

When the fly ash content in a concrete mix is between 10% to 50%, equation (6) can also be expressed as:

$$\sigma(\%) = 0.010C^2 + [6.74 - 0.00528FM] + \{(1685 + 126C - 1.324C^2)/(FM)[ln(T)]\} \quad (7)$$

After the compressive strength of fly ash concrete is determined as a percentage of compressive strength of control concrete without fly ash, the actual compressive strength of fly ash concrete can be determined by multiplying the strength at same control age with the percent compressive strength of fly ash concrete. The age of the concrete, T, is varied from 1 day to 1000 days. After 1100 days (3 years), the strength of fly ash concrete does not increase significantly (Hensen, 1990, supra).

Example 9

Prediction of Compressive Strength of Fractionated Fly Ash Concrete

Figure 11B:
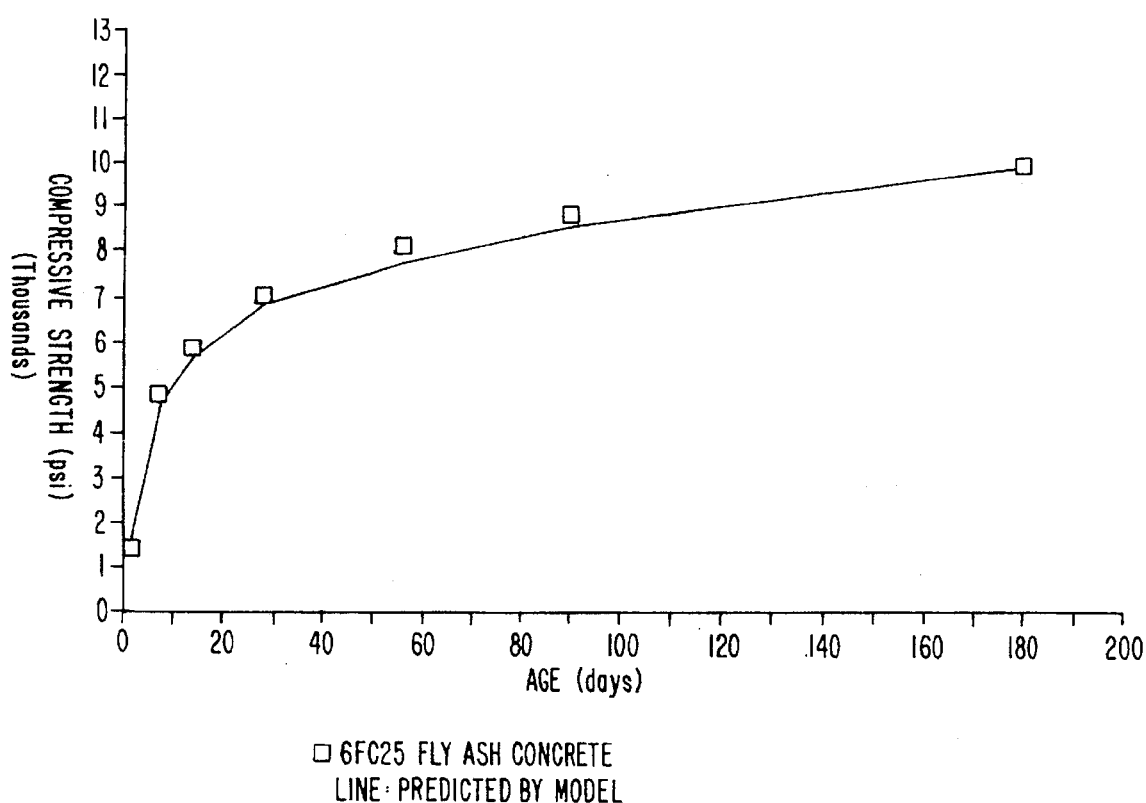
FIG. 11 presents graphs showing the predicted (solid line curve) and measured (open squares) compressive strength of concrete containing the 6F fly ash (dry bottom boiler fly ash) fraction as a replacement for 15% (A), 25% (B), 35% (C), and 50% (D) of cement in the concrete.
Figure 11D:
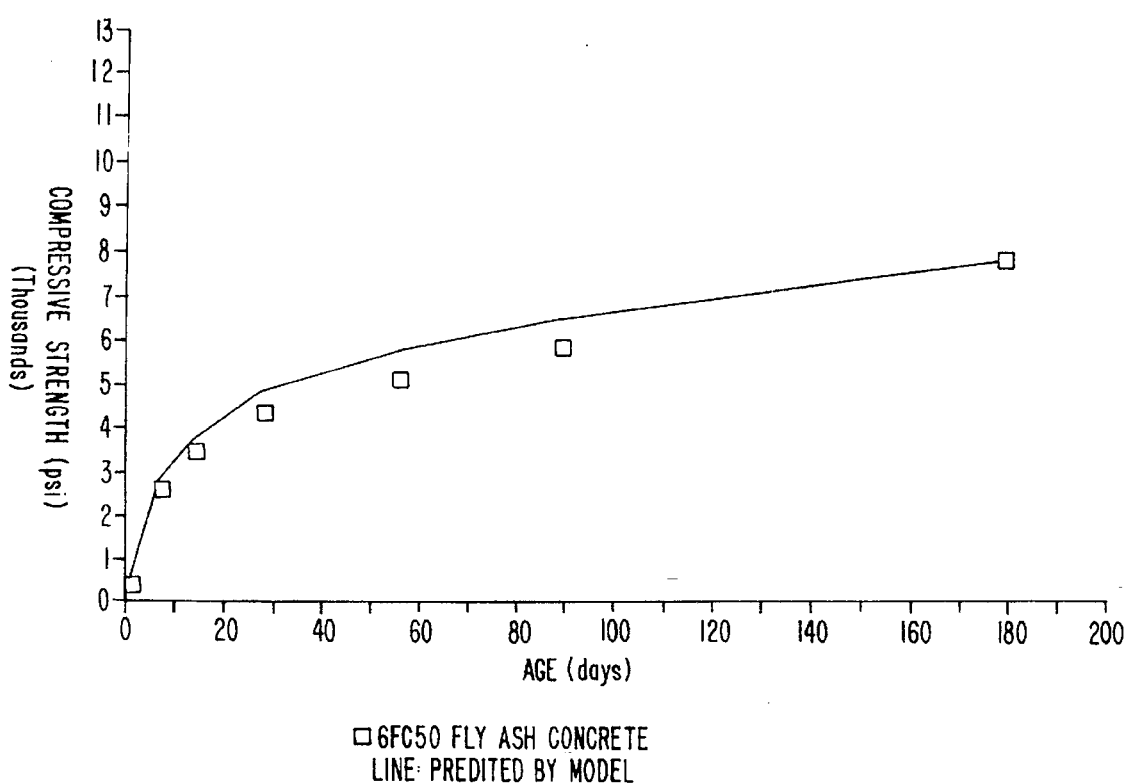
Figure 12A:
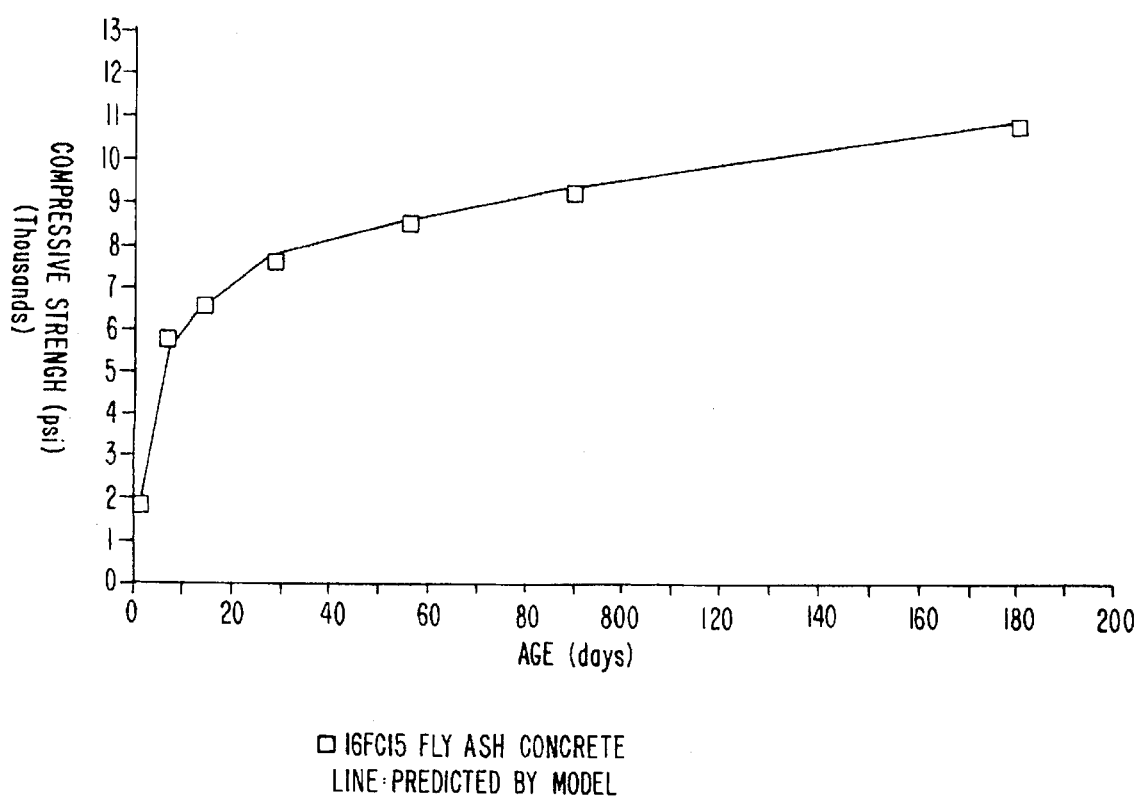
FIG. 12 presents graphs showing the predicted (solid line curve) and measured (open squares) compressive strength of concrete containing the 16F fly ash (wet bottom boiler fly ash) fraction as a replacement for 15% (A), 25% (B), 35% (C), and 50% (D) of cement in the concrete.
Figure 12B:
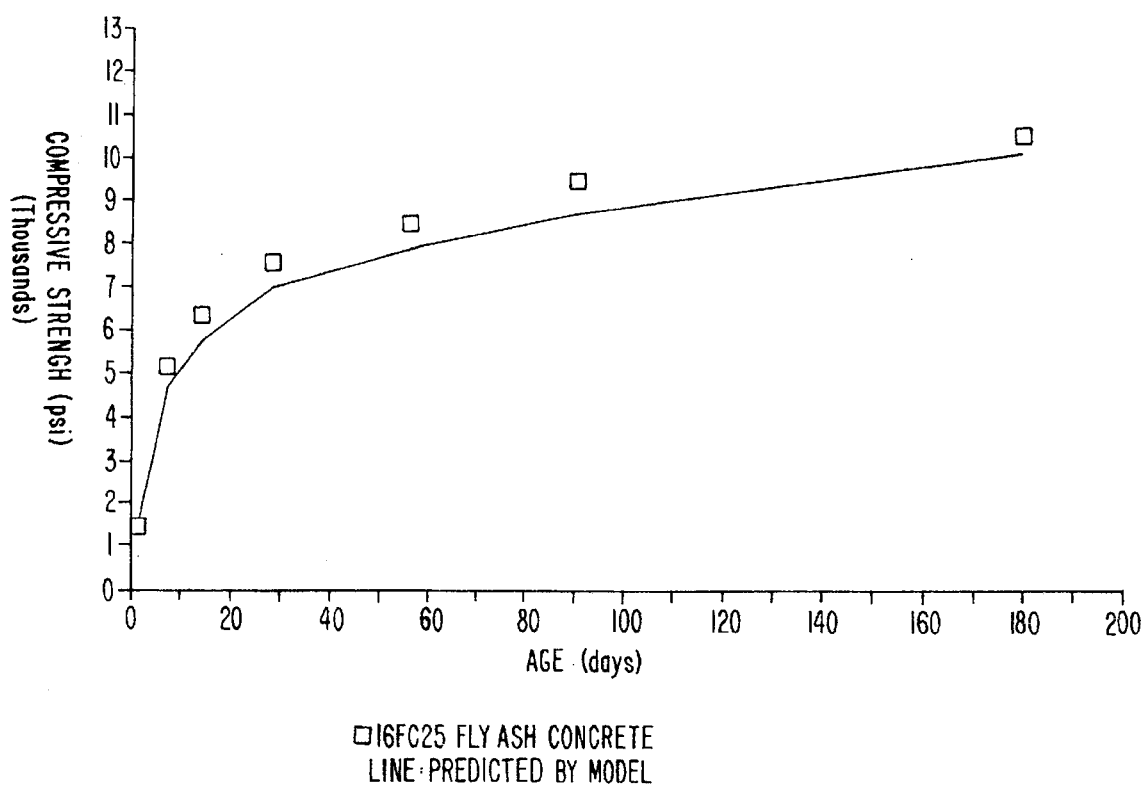
Figure 12C:
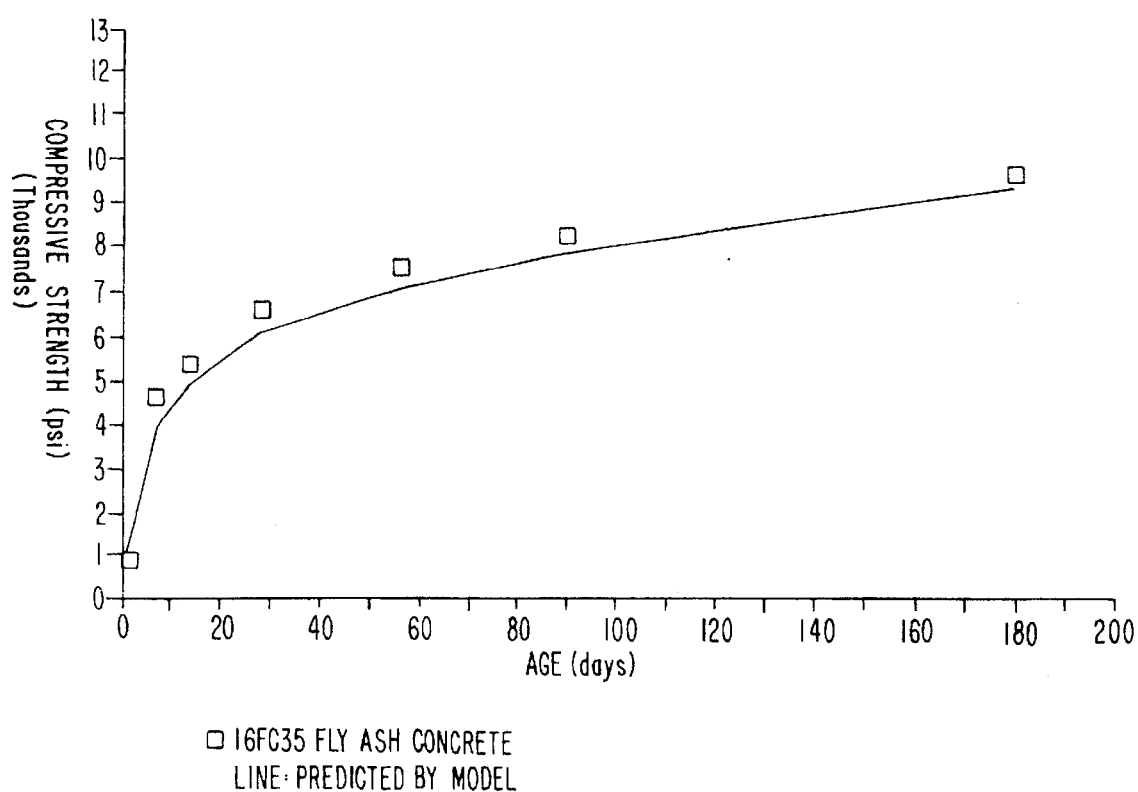
Figure 12D:
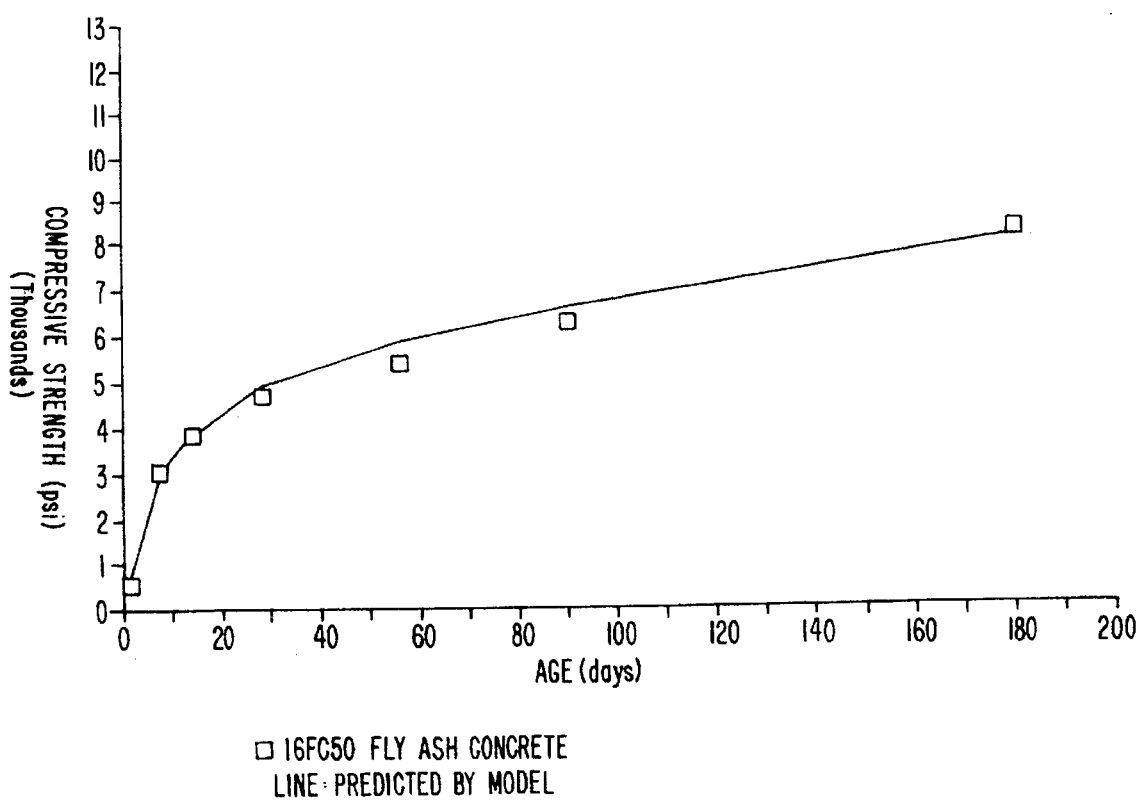

Regardless of the type of boiler use for burning coal to produce fly ash, equation (7) gives a very close prediction of compressive strength of feed and fractionated dry bottom boiler and wet bottom boiler fly ash concrete. FIGS. 11 A–D show the correlation between experimental observation (data points) and prediction with the model (line) for compressive strength over time of concrete containing 15%, 25%, 35% and 50% 6F dry bottom boiler fly ash. The predictions of compressive strengths of the fractionated 16F fly ash concrete using the equation are shown in FIGS. 12A–D. Equation (7) accurately predicted compressive strength for a given amount of fly ash for all of the fractions described above.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A high early strength concrete consisting essentially of about 1 part by weight cementitious materials, about 1 to about 3 parts by weight fine aggregate, about 1 to about 5 parts by weight coarse aggregate, and about 0.35 to about 0.6 parts by weight water, wherein the cementitious materials comprise from about 10% to about 35% by weight fly ash and about 65% to about 90% by weight cement, wherein the fly ash comprises at least 99% of particles having a particle size of less than 20 microns and having a fineness modulus of less than about 503, wherein the fineness modulus is calculated as a sum of the percent of fly ash particles having a size greater than 0, 1, 1.5, 2, 3, 5, 10, 20, 45, 75, 150, and 300 microns.

2. The concrete of claim 1 wherein the fly ash has a fineness modulus of less than about 350.

3. The concrete of claim 1 wherein the fine aggregate comprises sand.

4. The concrete of claim 1 wherein the fine aggregate comprises sand and fly ash, wherein a ratio by weight of sand to fly ash is from about 4:1 to about 1:1, and the fly ash has a fineness modulus of less than about 600, wherein the fineness modulus is calculated as the sum of the percent of fly ash retained on sieves of 0, 1, 1.5, 2, 3, 5, 10, 20, 45, 75, 150, and 300 microns.

5. The concrete of claim 1 further comprising silica fume.

6. The concrete of claim 1 further comprising glass fibers.

7. A high early strength mortar consisting essentially of about 1 part by weight cementitious materials, about 1 to about 3 parts by weight fine aggregate, and about 0.35 to about 0.6 parts by weight water, wherein the cementitious materials comprise from about 10% to about 35% by weight fly ash and about 65% to about 90% by weight cement, and wherein the fly ash comprises at least 99% of particles having a particle size of less than 20 microns and having a fineness modulus of less than about 503, wherein the fineness modulus is calculated as the sum of the percent of fly ash particles having a size greater than 0, 1, 1.5, 2, 3, 5, 10, 20, 45, 75, 150, and 300 microns.

8. The mortar of claim 7 wherein the fly ash is wet bottom boiler fly ash having a fineness modulus of less than about 350.

9. The mortar of claim 7 wherein the fine aggregate comprises sand.

10. The mortar of claim 7 wherein the fine aggregate comprises sand and fly ash, wherein ratio by weight of sand to fly ash is from about 4:1 to about 1:1, and the fly ash has a fineness modulus of less than about 600, wherein the fineness modulus is calculated as the sum of the percent of fly ash retained on sieves of 0, 1, 1.5, 2, 3, 5, 10, 20, 45, 75, 150, and 300 microns.

11. The mortar of claim 7 further comprising silica fume.

12. The mortar of claim 7 further comprising glass fibers.

* * * * *